US009676860B2

(12) United States Patent
Hartman et al.

(10) Patent No.: US 9,676,860 B2
(45) Date of Patent: Jun. 13, 2017

(54) DAC HYP COMPOSITIONS AND METHODS

(71) Applicant: AbbVie Biotherapeutics Inc., Redwood City, CA (US)

(72) Inventors: Taymar E. Hartman, Redwood City, CA (US); Paul W. Sauer, Fremont, CA (US); John E. Burky, Newark, CA (US); Mark C. Wesson, San Ramon, CA (US); Ping Y. Huang, Fremont, CA (US); Thomas J. Robinson, San Mateo, CA (US); Braeden D. Partridge, Sunnyvale, CA (US); J. Yun Tso, Menlo Park, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 166 days.

(21) Appl. No.: 14/601,909

(22) Filed: Jan. 21, 2015

(65) Prior Publication Data

US 2015/0203583 A1 Jul. 23, 2015

Related U.S. Application Data

(62) Division of application No. 13/481,081, filed on May 25, 2012, now abandoned.

(60) Provisional application No. 61/490,998, filed on May 27, 2011.

(51) Int. Cl.

| | |
|---|---|
| ***A61K 39/395*** | (2006.01) |
| ***C07K 16/24*** | (2006.01) |
| ***C07K 16/28*** | (2006.01) |
| ***A61K 38/21*** | (2006.01) |
| ***A61L 2/18*** | (2006.01) |
| *A61K 39/00* | (2006.01) |

(52) U.S. Cl.

CPC ........ *C07K 16/2866* (2013.01); *A61K 38/215* (2013.01); *A61K 39/3955* (2013.01); *A61L 2/18* (2013.01); *A61K 2039/505* (2013.01); *C07K 2317/14* (2013.01); *C07K 2317/24* (2013.01); *C07K 2317/41* (2013.01); *C07K 2317/56* (2013.01); *C07K 2317/73* (2013.01); *C07K 2317/732* (2013.01); *C07K 2317/76* (2013.01); *C07K 2317/92* (2013.01); *C07K 2317/94* (2013.01); *C12N 2500/95* (2013.01); *C12N 2510/02* (2013.01); *C12N 2510/04* (2013.01); *C12N 2511/00* (2013.01)

(58) Field of Classification Search

None

See application file for complete search history.

(56) References Cited

U.S. PATENT DOCUMENTS

| | | | |
|---|---|---|---|
| 8,993,524 | B2 | 3/2015 | Bedi et al. |
| 2005/0276799 | A1 | 12/2005 | Hinton et al. |
| 2007/0190057 | A1 | 8/2007 | Wu et al. |
| 2010/0173323 | A1 | 7/2010 | Strome et al. |
| 2011/0053223 | A1 | 3/2011 | Bayer et al. |
| 2012/0329709 | A1 | 12/2012 | Collins et al. |

FOREIGN PATENT DOCUMENTS

| | | | |
|---|---|---|---|
| EP | 1614693 | A1 | 1/2006 |
| EP | 2527429 | A2 | 11/2012 |
| GB | 1430566 | | 3/1976 |
| WO | WO 2007/146847 | A2 | 12/2007 |
| WO | WO-2008/004931 | A1 | 1/2008 |
| WO | WO-2009/017491 | A1 | 2/2009 |
| WO | WO-2010/025321 | A2 | 3/2010 |
| WO | WO 2010/141855 | A1 | 12/2010 |
| WO | WO-2011/017514 | A1 | 2/2011 |

OTHER PUBLICATIONS

Burky et al., 2007 "Protein-Free Fed-Batch Culture of Non-GS NS0 Cell Lines for Production of Recombinant Antibodies," *Biotechnology and Bioengineering* 96(2):281-293.

Cole et al., 1997 "Human IgG2 Variants of Chimeric Anti-CD3 Are Nonmitogenic to T Cells," *J Immunology* 159(7):3613-3621.

Hahn et al., 2006 "Comparison of protein A affinity sorbents III. Life time study," *J Chromatogr. A* 1102:224-231.

Hartman et al., 2007 "Derivation and Characterization of Cholesterol-Independent Non-GS NS0 Cell Lines for Production of Recombinant Antibodies," *Biotechnology and Bioengineering* 96(2):294-306.

Ishihara et al., 2007 "Accelerated purification process development of monoclonal antibodies for shortening time to clinic Design and case study of chromatography processes," *J Chromatogr. A* 1176:149-156.

Jimenez et al., 2010 "Towards the Implementation of Quality by Design to the Production of Therapeutic Monoclonal Antibodies with Desired Glycosylation Patterns," *American Institute of Chemical Engineers* 26(6):1505-1527.

Kostelny et al., 2001 "Humanization and Characterization of the Anti-HLA-DR Antibody 1D10," *Int. J Cancer* 93:556-565.

Lydersen et al., 1994 "Acid Precipitation of Mammalian Cell Fermentation Broth," *Annals of NY Academy of Sciences* 745: 222-231.

Peram et al., 2010 "Monoclonal Antibody Purification Using Cationic Polyelectrolytes: An Alternative to Column Chromatography," *Biotech Progress* 26(5):1322-1331.

Qian et al., 2007 "Structural characterization of N-linked oligosaccharides on monoclonal antibody cetuximab by the combination of orthogonal matrix-assisted laser desorption/ionization hybrid quadrupole-quadrupole time-of-flight tandem mass spectrometry and sequential enzymatic digestion" *Analytical Biochemistry* 364(1):8-18.

Rose et al., 2004 "Treatment of Multiple Sclerosis with an Anti-Interleukin-2 Receptor Monoclonal Antibody," Annals of Neurology 56(6):864-867.

(Continued)

*Primary Examiner* — Eric Olson

(74) *Attorney, Agent, or Firm* — Dechert LLP

(57) ABSTRACT

The present disclosure relates to compositions of daclizumab suitable for subcutaneous administration and methods of manufacturing thereof.

8 Claims, 30 Drawing Sheets

(56) References Cited

OTHER PUBLICATIONS

Satoh et al., 2006 "Non-fucosylated therapeutic antibodies as next-generation therapeutic antibodies," *Expert Opinion on Biological Therapy* 6(11):1161-1173.
Stadlmann et al., 2008 "Analysis of immunoglobulin glycosylation by LC-ESI-MS of glycopeptides and oligosaccharides" *Proteomics* 8(14):2858-2871.
Tejeda-Mansir et al., 1997 "Modelling regeneration effects on protein A affinity chromatography," *Bioprocess Engineering* 17:39-44.
Zhao et al., 2009 "Metabolic characteristics of GS-NS0 Myeloma cells producing anti-CD25 monoclonal antibody in serum-free culture," *Chin J Biotech* 25(7):1069-1076.
Zhu et al., 2008 "NS0 Cell Damage by High Gas Velocity Sparging in Protein-Free and Cholesterol-Free Cultures," *Biotechnology and Bioengineering* 101(4):751-760.
EP Partial Search Report from EP 12169595.1, dated Jul. 4, 2013.
EP Completed Search Report from EP 12169595.1, dated Oct. 1, 2013.
Office Action corresponding to related Chinese Patent Application No. 201210247261.4, dated Jan. 14, 2015.
Lim et al., 2010 "Current and future disease-modifying therapies in multiple sclerosis," *Int J Clin Pract* 64(5):637-650.
Butler, 2006 "Optimisation of the cellular metabolism of glycosylation for recombinant proteins produced by mammalian cell systems," *Cytotechnology* 50:57-76.
Gramer et al., 2011 Modulation of Antibody Galactosylation Through Feeding of Uridine, Manganese Chloride, and Galactose, *Biotechnol. & Bioeng.* 108:1591-1602.
Pacis et al., 2011 "Effects of Cell Culture Conditions on Antibody N-Linked Glycosylation—What Affects High Mannose 5 Glycoform," *Biotechnol. & Bioeng.* 108:2348-58.

$V_L$ DNA/Protein

```
  1  ATGGAGACCGATACCCTCCTGCTATGGGTCCTCCTGCTATGGGTCCCAGGATCAACCGGA
      M  E  T  D  T  L  L  L  W  V  L  L  L  W  V  P  G  S  T  G
 61  GATATTCAGATGACCCAGTCTCCATCTACCCTCTCTGCTAGCGTCGGGGATAGGGTCACC
      D  I  Q  M  T  Q  S  P  S  T  L  S  A  S  V  G  D  R  V  T
121  ATAACCTGCTCTGCCAGCTCAAGTATAAGTTACATGCACTGGTACCAGCAGAAGCCAGGC
      I  T  C  S  A  S  S  S  I  S  Y  M  H  W  Y  Q  Q  K  P  G
181  AAAGCTCCCAAGCTTCTAATTTATACCACATCCAACCTGGCTTCTGGAGTCCCTGCTCGC
      K  A  P  K  L  L  I  Y  T  T  S  N  L  A  S  G  V  P  A  R
241  TTCAGTGGCAGTGGATCTGGGACCGAGTTCACCCTCACAATCAGCTCTCTGCAGCCAGAT
      F  S  G  S  G  S  G  T  E  F  T  L  T  I  S  S  L  Q  P  D
301  GATTTCGCCACTTATTACTGCCATCAAAGGAGTACTTACCCACTCACGTTCGGTCAGGGG
      D  F  A  T  Y  Y  C  H  Q  R  S  T  Y  P  L  T  F  G  Q  G
361  ACCAAGGTGGAGGTCAAACGAACTGTGGCTGCACCATCTGTCTTCATCTTCCCGCCATCT
      T  K  V  E  V  K  R  T  V  A  A  P  S  V  F  I  F  P  P  S
421  GATGAGCAGTTGAAATCTGGAACTGCCTCTGTTGTGTGCCTGCTGAATAACTTCTATCCC
      D  E  Q  L  K  S  G  T  A  S  V  V  C  L  L  N  N  F  Y  P
481  AGAGAGGCCAAAGTACAGTGGAAGGTGGATAACGCCCTCCAATCGGGTAACTCCCAGGAG
      R  E  A  K  V  Q  W  K  V  D  N  A  L  Q  S  G  N  S  Q  E
541  AGTGTCACAGAGCAGGACAGCAAGGACAGCACCTACAGCCTCAGCAGCACCCTGACGCTG
      S  V  T  E  Q  D  S  K  D  S  T  Y  S  L  S  S  T  L  T  L
601  AGCAAAGCAGACTACGAGAAACACAAAGTCTACGCCTGCGAAGTCACCCATCAGGGCCTG
      S  K  A  D  Y  E  K  H  K  V  Y  A  C  E  V  T  H  Q  G  L
661  AGCTCGCCCGTCACAAAGAGCTTCAACAGGGGAGAGTGTTAG
      S  S  P  V  T  K  S  F  N  R  G  E  C  ·
```

FIG. 1

$V_H$ DNA/Protein

```
   1 ATGGGATGGAGCTGGATCTTTCTCTTCCTCCTGTCAGGTACCGCGGGCGTGCACTCTCAG
      M  G  W  S  W  I  F  L  F  L  L  S  G  T  A  G  V  H  S  Q
  61 GTCCAGCTTGTCCAGTCTGGGGCTGAAGTCAAGAAACCTGGCTCGAGCGTGAAGGTCTCC
      V  Q  L  V  Q  S  G  A  E  V  K  K  P  G  S  S  V  K  V  S
 121 TGCAAGGCTTCTGGCTACACCTTTACTAGCTACAGGATGCACTGGGTAAGGCAGGCCCCT
      C  K  A  S  G  Y  T  F  T  S  Y  R  M  H  W  V  R  Q  A  P
 181 GGACAGGGTCTGGAATGGATTGGATATATTAATCCGTCGACTGGGTATACTGAATACAAT
      G  Q  G  L  E  W  I  G  Y  I  N  P  S  T  G  Y  T  E  Y  N
 241 CAGAAGTTCAAGGACAAGGCAACAATTACTGCAGACGAATCCACCAATACAGCCTACATG
      Q  K  F  K  D  K  A  T  I  T  A  D  E  S  T  N  T  A  Y  M
 301 GAACTGAGCAGCCTGAGATCTGAGGACACCGCAGTCTATTACTGTGCAAGAGGGGGGGGG
      E  L  S  S  L  R  S  E  D  T  A  V  Y  Y  C  A  R  G  G  G
 361 GTCTTTGACTACTGGGGCCAAGGAACCCTGGTCACAGTCTCCTCAGCCTCCACCAAGGGC
      V  F  D  Y  W  G  Q  G  T  L  V  T  V  S  S  A  S  T  K  G
 421 CCATCGGTCTTCCCCCTGGCACCCTCCTCCAAGAGCACCTCTGGGGGCACAGCGGCCCTG
      P  S  V  F  P  L  A  P  S  S  K  S  T  S  G  G  T  A  A  L
 481 GGCTGCCTGGTCAAGGACTACTTCCCCGAACCGGTGACGGTGTCGTGGAACTCAGGCGCC
      G  C  L  V  K  D  Y  F  P  E  P  V  T  V  S  W  N  S  G  A
 541 CTGACCAGCGGCGTGCACACCTTCCCGGCTGTCCTACAGTCCTCAGGACTCTACTCCCTC
      L  T  S  G  V  H  T  F  P  A  V  L  Q  S  S  G  L  Y  S  L
 601 AGCAGCGTGGTGACCGTGCCCTCCAGCAGCTTGGGCACCCAGACCTACATCTGCAACGTG
      S  S  V  V  T  V  P  S  S  S  L  G  T  Q  T  Y  I  C  N  V
 661 AATCACAAGCCCAGCAACACCAAGGTGGACAAGAAAGTTGAGCCCAAATCTTGTGACAAA
      N  H  K  P  S  N  T  K  V  D  K  K  V  E  P  K  S  C  D  K
 721 ACTCACACATGCCCACCGTGCCCAGCACCTGAACTCCTGGGGGGACCGTCAGTCTTCCTC
      T  H  T  C  P  P  C  P  A  P  E  L  L  G  G  P  S  V  F  L
 781 TTCCCCCCAAAACCCAAGGACACCCTCATGATCTCCCGGACCCCTGAGGTCACATGCGTG
      F  P  P  K  P  K  D  T  L  M  I  S  R  T  P  E  V  T  C  V
 841 GTGGTGGACGTGAGCCACGAAGACCCTGAGGTCAAGTTCAACTGGTACGTGGACGGCGTG
      V  V  D  V  S  H  E  D  P  E  V  K  F  N  W  Y  V  D  G  V
 901 GAGGTGCATAATGCCAAGACAAAGCCGCGGGAGGAGCAGTACAACAGCACGTACCGTGTG
      E  V  H  N  A  K  T  K  P  R  E  E  Q  Y  N  S  T  Y  R  V
 961 GTCAGCGTCCTCACCGTCCTGCACCAGGACTGGCTGAATGGCAAGGAGTACAAGTGCAAG
      V  S  V  L  T  V  L  H  Q  D  W  L  N  G  K  E  Y  K  C  K
1021 GTCTCCAACAAAGCCCTCCCAGCCCCCATCGAGAAAACCATCTCCAAAGCCAAAGGGCAG
      V  S  N  K  A  L  P  A  P  I  E  K  T  I  S  K  A  K  G  Q
1081 CCCCGAGAACCACAGGTGTACACCCTGCCCCCATCCCGGGATGAGCTGACCAAGAACCAG
      P  R  E  P  Q  V  Y  T  L  P  P  S  R  D  E  L  T  K  N  Q
1141 GTCAGCCTGACCTGCCTGGTCAAAGGCTTCTATCCCAGCGACATCGCCGTGGAGTGGGAG
      V  S  L  T  C  L  V  K  G  F  Y  P  S  D  I  A  V  E  W  E
1201 AGCAATGGGCAGCCGGAGAACAACTACAAGACCACGCCTCCCGTGCTGGACTCCGACGGC
      S  N  G  Q  P  E  N  N  Y  K  T  T  P  P  V  L  D  S  D  G
1261 TCCTTCTTCCTCTACAGCAAGCTCACCGTGGACAAGAGCAGGTGGCAGCAGGGGAACGTC
      S  F  F  L  Y  S  K  L  T  V  D  K  S  R  W  Q  Q  G  N  V
1321 TTCTCATGCTCCGTGATGCATGAGGCTCTGCACAACCACTACACGCAGAAGAGCCTCTCC
      F  S  C  S  V  M  H  E  A  L  H  N  H  Y  T  Q  K  S  L  S
1381 CTGTCTCCGGGTAAATGA
      L  S  P  G  K  ·
```

FIG. 2

```
   1 GAATTCTCGAGCGCGTTACATAACTTACGGTAAATGGCCCGCCTGGCTGACCGCCCAACGACCCCCGCCCATTGACGTCAATAATGACGTATGT
  95 TCCCATAGTAACGCCAATAGGGACTTTCCATTGACGTCAATGGGTGGAGTATTTACGGTAAACTGCCCACTTGGCAGTACATCAAGTGTATCAT
 189 ATGCCAAGTACGCCCCCTATTGACGTCAATGACGGTAAATGGCCCGCCTGGCATTATGCCCAGTACATGACCTTATGGGACTTTCCTACTTGGC
 283 AGTACATCTACGTATTAGTCATCGCTATTACCATGGTGATGCGGTTTTGGCAGTACATCAATGGGCGTGGATAGCGGTTTGACTCACGGGGATT
 377 TCCAAGTCTCCACCCCATTGACGTCAATGGGAGTTTGTTTTGGCACCAAAATCAACGGGACTTTCCAAAATGTCGTAACAACTCCGCCCCATTG
 471 ACGCAAATGGGCGGTAGGCGTGTACGGTGGGAGGTCTATATAAGCAGAGCTCGTTTAGTGAACCGTCAGATCGCCTGGAGACGCCATCCACGCT
 565 GTTTTGACCTCCATAGAAGACACCGGGACCGATCCAGCCTCCGCCTCGATCGAGACGCGTCTAGACCACCATGGGATGGAGCTGGATCTTTCTC
 659 TTCCTCCTGTCAGGTACCGCGGGCGTGCACTCTCAGGTCCAGCTTGTCCAGTCTGGGGCTGAAGTCAAGAAACCTGGCTCGAGCGTGAAGGTCT
 753 CCTGCAAGGCTTCTGGCTACACCTTTACTAGCTACAGGATGCACTGGGTAAGGCAGGCCCCTGGACAGGGTCTGGAATGGATTGGATATATTAA
 847 TCCGTCGACTGGGTATACTGAATACAATCAGAAGTTCAAGGACAAGGCAACAATTACTGCAGACGAATCCACCAATACAGCCTACATGGAACTG
 941 AGCAGCCTGAGATCTGAGGACACCGCAGTCTATTACTGTGCAAGAGGGGGGGGGGTCTTTGACTACTGGGGCCAAGGAACCCTGGTCACAGTCT
1035 CCTCAGGTGAGTCCTTAAAACCTCTAGAGCTTTCTGGGGCAGGCCAGGCCTGACCTTGGCTTTGGGGCAGGGAGGGGGCTAAGGTGAGGCAGGT
1129 GGCGCCAGCCAGGTGCACACCCAATGCCCATGAGCCCAGACACTGGACGCTGAACCTCGCGGACAGTTAAGAACCCAGGGGCCTCTGCGCCCTG
1223 GGCCCAGCTCTGTCCCACACCGCGGTCACATGGCACCACCTCTCTTGCAGCCTCCACCAAGGGCCCATCGGTCTTCCCCCTGGCACCCTCCTCC
1317 AAGAGCACCTCTGGGGGCACAGCGGCCCTGGGCTGCCTGGTCAAGGACTACTTCCCCGAACCGGTGACGGTGTCGTGGAACTCAGGCGCCCTGA
1411 CCAGCGGCGTGCACACCTTCCCGGCTGTCCTACAGTCCTCAGGACTCTACTCCCTCAGCAGCGTGGTGACCGTGCCCTCCAGCAGCTTGGGCAC
1505 CCAGACCTACATCTGCAACGTGAATCACAAGCCCAGCAACACCAAGGTGGACAAGAAAGTTGGTGAGAGGCCAGCACAGGGAGGGAGGGTGTCT
1599 GCTGGAAGCCAGGCTCAGCGCTCCTGCCTGGACGCATCCCGGCTATGCAGCCCCAGTCCAGGGCAGCAAGGCAGGCCCCGTCTGCCTCTTCACC
1693 CGGAGGCCTCTGCCCGCCCCACTCATGCTCAGGGAGAGGGTCTTCTGGCTTTTTCCCCAGGCTCTGGGCAGGCACAGGCTAGGTGCCCCTAACC
1787 CAGGCCCTGCACACAAAGGGGCAGGTGCTGGGCTCAGACCTGCCAAGAGCCATATCCGGGAGGACCCTGCCCCTGACCTAAGCCCACCCCAAAG
1881 GCCAAACTCTCCACTCCCTCAGCTCGGACACCTTCTCTCCTCCCAGATTCCAGTAACTCCCAATCTTCTCTCTGCAGAGCCCAAATCTTGTGAC
1975 AAAACTCACACATGCCCACCGTGCCCAGGTAAGCCAGCCCAGGCCTCGCCCTCCAGCTCAAGGCGGGACAGGTGCCCTAGAGTAGCCTGCATCC
2069 AGGGACAGGCCCCAGCCGGGTGCTGACACGTCCACCTCCATCTCTTCCTCAGCACCTGAACTCCTGGGGGGACCGTCAGTCTTCCTCTTCCCCC
2163 CAAAACCCAAGGACACCCTCATGATCTCCCGGACCCCTGAGGTCACATGCGTGGTGGTGGACGTGAGCCACGAAGACCCTGAGGTCAAGTTCAA
2257 CTGGTACGTGGACGGCGTGGAGGTGCATAATGCCAAGACAAAGCCGCGGGAGGAGCAGTACAACAGCACGTACCGTGTGGTCAGCGTCCTCACC
2351 GTCCTGCACCAGGACTGGCTGAATGGCAAGGAGTACAAGTGCAAGGTCTCCAACAAAGCCCTCCCAGCCCCCATCGAGAAAACCATCTCCAAAG
2445 CCAAAGGTGGGACCCGTGGGGTGCGAGGGCCACATGGACAGAGGCCGGCTCGGCCCACCCTCTGCCCTGAGAGTGACCGCTGTACCAACCTCTG
2539 TCCCTACAGGGCAGCCCCGAGAACCACAGGTGTACACCCTGCCCCCATCCCGGGATGAGCTGACCAAGAACCAGGTCAGCCTGACCTGCCTGGT
2633 CAAAGGCTTCTATCCCAGCGACATCGCCGTGGAGTGGGAGAGCAATGGGCAGCCGGAGAACAACTACAAGACCACGCCTCCCGTGCTGGACTCC
2727 GACGGCTCCTTCTTCCTCTACAGCAAGCTCACCGTGGACAAGAGCAGGTGGCAGCAGGGGAACGTCTTCTCATGCTCCGTGATGCATGAGGCTC
2821 TGCACAACCACTACACGCAGAAGAGCCTCTCCCTGTCTCCGGGTAAATGAGTGCGACGGCCGGCAAGCCCCCGCTCCCCGGGCTCTCGCGGTCG
2915 CACGAGGATGCTTGGCACGTACCCCCTGTACATACTTCCCGGGCGCCCAGCATGGAAATAAAGCACCCAGCGCTGCCCTGGGCCCCTGCGAGAC
3009 TGTGATGGTTCTTTCCACGGGTCAGGCCGAGTCTGAGGCCTGAGTGGCATGAGGGAGGCAGAGCGGGTCCCACTGTCCCCACACTGGCCCAGGC
3103 TGTGCAGGTGTGCCTGGGCCGCCTAGGGTGGGGCTCAGCCAGGGGCTGCCCTCGGCAGGGTGGGGGATTTGCCAGCGTGGCCCTCCCTCCAGCA
```

FIG. 3A

```
3197 GCACCTGCCCTGGGCTGGGCCACGGGAAGCCCTAGGAGCCCCTGGGGACAGACACACAGCCCCTGCCTCTGTAGGAGACTGTCCTGTTCTGTGA
3291 GCGCCCTGTCCTCCGACCTCCATGCCCACTCGGGGGCATGCCTAGTCCATGTGCGTAGGGACAGGCCCTCCCTCACCCATCTACCCCCACGGCA
3385 CTAACCCCTGGCTGCCCTGCCCAGCCTCGCACCCGCATGGGGACACAACCGACTCCGGGGACATGCACTCTCGGGCCCTGTGGAGGGACTGGTG
3479 CAGATGCCCACACACACACTCAGCCCAGACCCGTTCAACAAACCCCGCACTGAGGTTGGCCGGCCACACGGCCACCACACACACACGTGCACGC
3573 CTCACACACGGAGCCTCACCCGGGCGAACTGCACAGCACCCAGACCAGAGCAAGGTCCTCGCACACGTGAACACTCCTCGGACACAGGCCCCCA
3667 CGAGCCCCACGCGGCACCTCAAGGCCCACGAGCCTCTCGGCAGCTTCTCCACATGCTGACCTGCTCAGACAAACCCAGCCCTCCTCTCACAAGG
3761 GTGCCCCTGCAGCCGCCACACACACACAGGGGATCACACACCACGTCACGTCCCTGGCCCTGGCCCACTTCCCAGTGCCGCCCTTCCCTGCAGG
3855 ATCCTGGCCTTGGGGGAGGGGGAGGCCAGAATGACTCCAAGAGCTACAGGAGGCAGGTCAGAGACCCCACTGGACAAACAGTGGCTGGACTCTG
3949 CACCATAACACACAATCACAGGGGAGTGAGCTGGAATTCTCGAGCGCGTTACATAACTTACGGTAAATGGCCCGCCTGGCTGACCGCCCAACGA
4043 CCCCCGCCCATTGACGTCAATAATGACGTATGTTCCCATAGTAACGCCAATAGGGACTTTCCATTGACGTCAATGGGTGGAGTATTTACGGTAA
4137 ACTGCCCACTTGGCAGTACATCAAGTGTATCATATGCCAAGTACGCCCCCTATTGACGTCAATGACGGTAAATGGCCCGCCTGGCATTATGCCC
4231 AGTACATGACCTTATGGGACTTTCCTACTTGGCAGTACATCTACGTATTAGTCATCGCTATTACCATGGTGATGCGGTTTTGGCAGTACATCAA
4325 TGGGCGTGGATAGCGGTTTGACTCACGGGGATTTCCAAGTCTCCACCCCATTGACGTCAATGGGAGTTTGTTTTGGCACCAAAATCAACGGGAC
4419 TTTCCAAAATGTCGTAACAACTCCGCCCCATTGACGCAAATGGGCGGTAGGCGTGTACGGTGGGAGGTCTATATAAGCAGAGCTCGTTTAGTGA
4513 ACCGTCAGATCGCCTGGAGACGCCATCCACGCTGTTTTGACCTCCATAGAAGACACCGGGACCGATCCAGCCTCCGCCTCGATCGAGACGCGTC
4607 TAGATGGAGACCGATACCCTCCTGCTATGGGTCCTCCTGCTATGGGTCCCAGGATCAACCGGAGATATTCAGATGACCCAGTCTCCATCTACCC
4701 TCTCTGCTAGCGTCGGGGATAGGGTCACCATAACCTGCTCTGCCAGCTCAAGTATAAGTTACATGCACTGGTACCAGCAGAAGCCAGGCAAAGC
4795 TCCCAAGCTTCTAATTTATACCACATCCAACCTGGCTTCTGGAGTCCCTGCTCGCTTCAGTGGCAGTGGATCTGGGACCGAGTTCACCCTCACA
4889 ATCAGCTCTCTGCAGCCAGATGATTTCGCCACTTATTACTGCCATCAAAGGAGTACTTACCCACTCACGTTCGGTCAGGGGACCAAGGTGGAGG
4983 TCAAACGTAAGTACACTTTTCTAGAAATTCTAAACTCTGAGGGGGTCGGATGACGTGGCCATTCTTTGCCTAAAGCATTGAGTTTACTGCAAGG
5077 TCAGAAAAGCATGCAAAGCCCTCAGAATGGCTGCAAAGAGCTCCAACAAAACAATTTAGAACTTTATTAAGGAATAGGGGGAAGCTAGGAAGAA
5171 ACTCAAAACATCAAGATTTTAAATACGCTTCTTGGTCTCCTTGCTATAATTATCTGGGATAAGCATGCTGTTTTCTGTCTGTCCCTAACATGCT
5265 CTGTGATTATCCGCAAACAACACACCCAAGGGCAGAACTTTGTTACTTAAACACCATCCTGTTTGCTTCTTTCCTCAGGAACTGTGGCTGCACC
5359 ATCTGTCTTCATCTTCCCGCCATCTGATGAGCAGTTGAAATCTGGAACTGCCTCTGTTGTGTGCCTGCTGAATAACTTCTATCCCAGAGAGGCC
5453 AAAGTACAGTGGAAGGTGGATAACGCCCTCCAATCGGGTAACTCCCAGGAGAGTGTCACAGAGCAGGACAGCAAGGACAGCACCTACAGCCTCA
5547 GCAGCACCCTGACGCTGAGCAAAGCAGACTACGAGAAACACAAAGTCTACGCCTGCGAAGTCACCCATCAGGGCCTGAGCTCGCCCGTCACAAA
5641 GAGCTTCAACAGGGGAGAGTGTTAGAGGGAGAAGTGCCCCCACCTGCTCCTCAGTTCCAGCCTGACCCCCTCCCATCCTTTGGCCTCTGACCCT
5735 TTTTCCACAGGGGACCTACCCCTATTGCGGTCCTCCAGCTCATCTTTCACCTCACCCCCCTCCTCCTCCTTGGCTTTAATTATGCTAATGTTGG
5829 AGGAGAATGAATAAATAAAGTGAATCTTTGCACCTGTGGTTTCTCTCTTTCCTCATTTAATAATTATTATCTGTTGTTTACCAACTACTCAATT
5923 TCTCTTATAAGGGACTAAATATGTAGTCATCCTAAGGCGCATAACCATTTATAAAAATCATCCTTCATTCTATTTTACCCTATCATCCTCTGCA
6017 AGACAGTCCTCCCTCAAACCCACAAGCCTTCTGTCCTCACAGTCCCCTGGGCCATGGTAGGAGAGACTTGCTTCCTTGTTTTCCCCTCCTCAGC
6111 AAGCCCTCATAGTCCTTTTTAAGGGTGACAGGTCTTACAGTCATATATCCTTTGATTCAATTCCCTGAGAATCAACCAAAGCAAATTTTTCAAA
6205 AGAAGAAACCTGCTATAAAGAGAATCATTCATTGCAACATGATATAAAATAACAACACAATAAAAGCAATTAAATAAACAAACAATAGGGAAAT
```

FIG. 3B

```
6299 GTTTAAGTTCATCATGGTACTTAGACTTAATGGAATGTCATGCCTTATTTACATTTTTAAACAGGTACTGAGGGACTCCTGTCTGCCAAGGGCC
6393 GTATTGAGTACTTTCCACAACCTAATTTAATCCACACTATACTGTGAGATTAAAAACATTCATTAAAATGTTGCAAAGGTTCTATAAAGCTGAG
6487 AGACAAATATATTCTATAACTCAGCAATCCCACTTCTAGGATCCGGGCCGCATGCATCTCAATTAGTCAGCAACCATAGTCCCGCCCCTAACTC
6581 CGCCCATCCCGCCCCTAACTCCGCCCAGTTCCGCCCATTCTCCGCCCCATGGCTGACTAATTTTTTTTATTTATGCAGAGGCCGAGGCCGCCTC
6675 GGCCTCTGAGCTATTCCAGAAGTAGTGAGGAGGCTTTTTTGGAGGCCTAGGCTTTTGCAAAAAGCTTGGACACAAGACAGGCTTGCGAGATATG
6769 TTTGAGAATACCACTTTATCCCGCGTCAGGGAGAGGCAGTGCGTAAAAAGACGCGGACTCATGTGAAATACTGGTTTTTAGTGCGCCAGATCTC
6863 TATAATCTCGCGCAACCTATTTTCCCCTCGAACACTTTTTAAGCCGTAGATAAACAGGCTGGGACACTTCACATGAGCGAAAAATACATCGTCA
6957 CCTGGGACATGTTGCAGATCCATGCACGTAAACTCGCAAGCCGACTGATGCCTTCTGAACAATGGAAAGGCATTATTGCCGTAAGCCGTGGCGG
7051 TCTGGTACCGGGTGCGTTACTGGCGCGTGAACTGGGTATTCGTCATGTCGATACCGTTTGTATTTCCAGCTACGATCACGACAACCAGCGCGAG
7145 CTTAAAGTGCTGAAACGCGCAGAAGGCGATGGCGAAGGCTTCATCGTTATTGATGACCTGGTGGATACCGGTGGTACTGCGGTTGCGATTCGTG
7239 AAATGTATCCAAAAGCGCACTTTGTCACCATCTTCGCAAAACCGGCTGGTCGTCCGCTGGTTGATGACTATGTTGTTGATATCCCGCAAGATAC
7333 CTGGATTGAACAGCCGTGGGATATGGGCGTCGTATTCGTCCCGCCAATCTCCGGTCGCTAATCTTTTCAACGCCTGGCACTGCCGGGCGTTGTT
7427 CTTTTTAACTTCAGGCGGGTTACAATAGTTTCCAGTAAGTATTCTGGAGGCTGCATCCATGACACAGGCAAACCTGAGCGAAACCCTGTTCAAA
7521 CCCCGCTTTAAACATCCTGAAACCTCGACGCTAGTCCGCCGCTTTAATCACGGCGCACAACCGCCTGTGCAGTCGGCCCTTGATGGTAAAACCA
7615 TCCCTCACTGGTATCGCATGATTAACCGTCTGATGTGGATCTGGCGCGGCATTGACCCACGCGAAATCCTCGACGTCCAGGCACGTATTGTGAT
7709 GAGCGATGCCGAACGTACCGACGATGATTTATACGATACGGTGATTGGCTACCGTGGCGGCAACTGGATTTATGAGTGGGCCCCGGATCTTTGT
7803 GAAGGAACCTTACTTCTGTGGTGTGACATAATTGGACAAACTACCTACAGAGATTTAAAGCTCTAAGGTAAATATAAAATTTTTAAGTGTATAA
7897 TGTGTTAAACTACTGATTCTAATTGTTTGTGTATTTTAGATTCCAACCTATGGAACTGATGAATGGGAGCAGTGGTGGAATGCCTTTAATGAGG
7991 AAAACCTGTTTTGCTCAGAAGAAATGCCATCTAGTGATGATGAGGCTACTGCTGACTCTCAACATTCTACTCCTCCAAAAAAGAAGAGAAAGGT
8085 AGAAGACCCCAAGGACTTTCCTTCAGAATTGCTAAGTTTTTTGAGTCATGCTGTGTTTAGTAATAGAACTCTTGCTTGCTTTGCTATTTACACC
8179 ACAAAGGAAAAAGCTGCACTGCTATACAAGAAAATTATGGAAAAATATTCTGTAACCTTTATAAGTAGGCATAACAGTTATAATCATAACATAC
8273 TGTTTTTTCTTACTCCACACAGGCATAGAGTGTCTGCTATTAATAACTATGCTCAAAAATTGTGTACCTTTAGCTTTTTAATTTGTAAAGGGGT
8367 TAATAAGGAATATTTGATGTATAGTGCCTTGACTAGAGATCATAATCAGCCATACCACATTTGTAGAGGTTTTACTTGCTTTAAAAAACCTCCC
8461 ACACCTCCCCCTGAACCTGAAACATAAAATGAATGCAATTGTTGTTGTTAACTTGTTTATTGCAGCTTATAATGGTTACAAATAAAGCAATAGC
8555 ATCACAAATTTCACAAATAAAGCATTTTTTTCACTGCATTCTAGTTGTGGTTTGTCCAAACTCATCAATGTATCTTATCATGTCTGGATCCTGC
8649 CTCGCGCGTTTCGGTGATGACGGTGAAAACCTCTGACACATGCAGCTCCCGGAGACGGTCACAGCTTGTCTGTAAGCGGATGCCGGGAGCAGAC
8743 AAGCCCGTCAGGGCGCGTCAGCGGGTGTTGGCGGGTGTCGGGGCGCAGCCATGACCCAGTCACGTAGCGATAGCGGAGTGTATACTGGCTTAAC
8837 TATGCGGCATCAGAGCAGATTGTACTGAGAGTGCACCATATGCGGTGTGAAATACCGCACAGATGCGTAAGGAGAAAATACCGCATCAGGCGCT
8931 CTTCCGCTTCCTCGCTCACTGACTCGCTGCGCTCGGTCGTTCGGCTGCGGCGAGCGGTATCAGCTCACTCAAAGGCGGTAATACGGTTATCCAC
9025 AGAATCAGGGGATAACGCAGGAAAGAACATGTGAGCAAAAGGCCAGCAAAAGGCCAGGAACCGTAAAAAGGCCGCGTTGCTGGCGTTTTTCCAT
9119 AGGCTCCGCCCCCCTGACGAGCATCACAAAAATCGACGCTCAAGTCAGAGGTGGCGAAACCCGACAGGACTATAAAGATACCAGGCGTTTCCCC
9213 CTGGAAGCTCCCTCGTGCGCTCTCCTGTTCCGACCCTGCCGCTTACCGGATACCTGTCCGCCTTTCTCCCTTCGGGAAGCGTGGCGCTTTCTCA
9307 ATGCTCACGCTGTAGGTATCTCAGTTCGGTGTAGGTCGTTCGCTCCAAGCTGGGCTGTGTGCACGAACCCCCCGTTCAGCCCGACCGCTGCGCC
```

FIG. 3C

```
9401  TTATCCGGTAACTATCGTCTTGAGTCCAACCCGGTAAGACACGACTTATCGCCACTGGCAGCAGCCACTGGTAACAGGATTAGCAGAGCGAGGT
9495  ATGTAGGCGGTGCTACAGAGTTCTTGAAGTGGTGGCCTAACTACGGCTACACTAGAAGGACAGTATTTGGTATCTGCGCTCTGCTGAAGCCAGT
9589  TACCTTCGGAAAAAGAGTTGGTAGCTCTTGATCCGGCAAACAAACCACCGCTGGTAGCGGTGGTTTTTTTGTTTGCAAGCAGCAGATTACGCGC
9683  AGAAAAAAAGGATCTCAAGAAGATCCTTTGATCTTTTCTACGGGGTCTGACGCTCAGTGGAACGAAAACTCACGTTAAGGGATTTTGGTCATGA
9777  GATTATCAAAAAGGATCTTCACCTAGATCCTTTTAAATTAAAAATGAAGTTTTAAATCAATCTAAAGTATATATGAGTAAACTTGGTCTGACAG
9871  TTACCAATGCTTAATCAGTGAGGCACCTATCTCAGCGATCTGTCTATTTCGTTCATCCATAGTTGCCTGACTCCCCGTCGTGTAGATAACTACG
9965  ATACGGGAGGGCTTACCATCTGGCCCCAGTGCTGCAATGATACCGCGAGACCCACGCTCACCGGCTCCAGATTTATCAGCAATAAACCAGCCAG
10059 CCGGAAGGGCCGAGCGCAGAAGTGGTCCTGCAACTTTATCCGCCTCCATCCAGTCTATTAATTGTTGCCGGGAAGCTAGAGTAAGTAGTTCGCC
10153 AGTTAATAGTTTGCGCAACGTTGTTGCCATTGCTGCAGGCATCGTGGTGTCACGCTCGTCGTTTGGTATGGCTTCATTCAGCTCCGGTTCCCAA
10247 CGATCAAGGCGAGTTACATGATCCCCCATGTTGTGCAAAAAAGCGGTTAGCTCCTTCGGTCCTCCGATCGTTGTCAGAAGTAAGTTGGCCGCAG
10341 TGTTATCACTCATGGTTATGGCAGCACTGCATAATTCTCTTACTGTCATGCCATCCGTAAGATGCTTTTCTGTGACTGGTGAGTACTCAACCAA
10435 GTCATTCTGAGAATAGTGTATGCGGCGACCGAGTTGCTCTTGCCCGGCGTCAACACGGGATAATACCGCGCCACATAGCAGAACTTTAAAAGTG
10529 CTCATCATTGGAAAACGTTCTTCGGGGCGAAAACTCTCAAGGATCTTACCGCTGTTGAGATCCAGTTCGATGTAACCCACTCGTGCACCCAACT
10623 GATCTTCAGCATCTTTTACTTTCACCAGCGTTTCTGGGTGAGCAAAAACAGGAAGGCAAAATGCCGCAAAAAAGGGAATAAGGGCGACACGGAA
10717 ATGTTGAATACTCATACTCTTCCTTTTTCAATATTATTGAAGCATTTATCAGGGTTATTGTCTCATGAGCGGATACATATTTGAATGTATTTAG
10811 AAAAATAAACAAATAGGGGTTCCGCGCACATTTCCCCGAAAAGTGCCACCTGACGTCTAAGAAACCATTATTATCATGACATTAACCTATAAAA
10905 ATAGGCGTATCACGAGGCCCTTTCGTCTTCAA
```

FIG. 3D

GCATGCATCTCAATTAGTCAGCAACCATAGTCCCGCCCCTAAC
TCCGCCCATCCCGCCCCTAACTCCGCCCAGTTCCGCCCATTCT
CCGCCCCATGGCTGACTAATTTTTTTTATTTATGCAGAGGCCG
AGGCCGCCTCGGCCT CTGAGCTATTCCAGAAGTAGTGAGGAGG
CTTTTTTGGAGGCCTAGGCTTTTGCAAAAAGCTT

FIG. 3E

DAC HYP UF

SEQUENCE LISTING

```
<160> NUMBER OF SEQ ID NOS: 14

<210> SEQ ID NO 1
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(699)

<400> SEQUENCE: 1

atg gag acc gat acc ctc ctg cta tgg gtc ctc ctg cta tgg gtc cca       48
Met Glu Thr Asp Thr Leu Leu Leu Trp Val Leu Leu Leu Trp Val Pro
1               5                   10                  15
```

```
gga tca acc gga gat att cag atg acc cag tct cca tct acc ctc tct        96
Gly Ser Thr Gly Asp Ile Gln Met Thr Gln Ser Pro Ser Thr Leu Ser
            20                  25                  30

gct agc gtc ggg gat agg gtc acc ata acc tgc tct gcc agc tca agt       144
Ala Ser Val Gly Asp Arg Val Thr Ile Thr Cys Ser Ala Ser Ser Ser
        35                  40                  45

ata agt tac atg cac tgg tac cag cag aag cca ggc aaa gct ccc aag       192
Ile Ser Tyr Met His Trp Tyr Gln Gln Lys Pro Gly Lys Ala Pro Lys
    50                  55                  60

ctt cta att tat acc aca tcc aac ctg gct tct gga gtc cct gct cgc       240
Leu Leu Ile Tyr Thr Thr Ser Asn Leu Ala Ser Gly Val Pro Ala Arg
65                  70                  75                  80

ttc agt ggc agt gga tct ggg acc gag ttc acc ctc aca atc agc tct       288
Phe Ser Gly Ser Gly Ser Gly Thr Glu Phe Thr Leu Thr Ile Ser Ser
                85                  90                  95

ctg cag cca gat gat ttc gcc act tat tac tgc cat caa agg agt act       336
Leu Gln Pro Asp Asp Phe Ala Thr Tyr Tyr Cys His Gln Arg Ser Thr
            100                 105                 110

tac cca ctc acg ttc ggt cag ggg acc aag gtg gag gtc aaa cga act       384
Tyr Pro Leu Thr Phe Gly Gln Gly Thr Lys Val Glu Val Lys Arg Thr
        115                 120                 125

gtg gct gca cca tct gtc ttc atc ttc ccg cca tct gat gag cag ttg       432
Val Ala Ala Pro Ser Val Phe Ile Phe Pro Pro Ser Asp Glu Gln Leu
    130                 135                 140

aaa tct gga act gcc tct gtt gtg tgc ctg ctg aat aac ttc tat ccc       480
Lys Ser Gly Thr Ala Ser Val Val Cys Leu Leu Asn Asn Phe Tyr Pro
145                 150                 155                 160

aga gag gcc aaa gta cag tgg aag gtg gat aac gcc ctc caa tcg ggt       528
Arg Glu Ala Lys Val Gln Trp Lys Val Asp Asn Ala Leu Gln Ser Gly
                165                 170                 175

aac tcc cag gag agt gtc aca gag cag gac agc aag gac agc acc tac       576
Asn Ser Gln Glu Ser Val Thr Glu Gln Asp Ser Lys Asp Ser Thr Tyr
            180                 185                 190

agc ctc agc agc acc ctg acg ctg agc aaa gca gac tac gag aaa cac       624
Ser Leu Ser Ser Thr Leu Thr Leu Ser Lys Ala Asp Tyr Glu Lys His
        195                 200                 205

aaa gtc tac gcc tgc gaa gtc acc cat cag ggc ctg agc tcg ccc gtc       672
Lys Val Tyr Ala Cys Glu Val Thr His Gln Gly Leu Ser Ser Pro Val
    210                 215                 220

aca aag agc ttc aac agg gga gag tgt tag                               702
Thr Lys Ser Phe Asn Arg Gly Glu Cys
225                 230
```

<210> SEQ ID NO 2
<211> LENGTH: 233
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Thr Leu Ser
            20                  25                  30

Ala Ser Val Gly Asp Arg Val Thr Ile Thr Cys Ser Ala Ser Ser Ser
        35                  40                  45

Ile Ser Tyr Met His Trp Tyr Gln Gln Lys Pro Gly Lys Ala Pro Lys
    50                  55                  60
```

```
Leu Leu Ile Tyr Thr Thr Ser Asn Leu Ala Ser Gly Val Pro Ala Arg
65                  70                  75                  80

Phe Ser Gly Ser Gly Ser Gly Thr Glu Phe Thr Leu Thr Ile Ser Ser
                85                  90                  95

Leu Gln Pro Asp Asp Phe Ala Thr Tyr Tyr Cys His Gln Arg Ser Thr
            100                 105                 110

Tyr Pro Leu Thr Phe Gly Gln Gly Thr Lys Val Glu Val Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 3
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1395)

<400> SEQUENCE: 3

atg gga tgg agc tgg atc ttt ctc ttc ctc ctg tca ggt acc gcg ggc       48
Met Gly Trp Ser Trp Ile Phe Leu Phe Leu Leu Ser Gly Thr Ala Gly
1               5                   10                  15

gtg cac tct cag gtc cag ctt gtc cag tct ggg gct gaa gtc aag aaa       96
Val His Ser Gln Val Gln Leu Val Gln Ser Gly Ala Glu Val Lys Lys
            20                  25                  30

cct ggc tcg agc gtg aag gtc tcc tgc aag gct tct ggc tac acc ttt      144
Pro Gly Ser Ser Val Lys Val Ser Cys Lys Ala Ser Gly Tyr Thr Phe
        35                  40                  45

act agc tac agg atg cac tgg gta agg cag gcc cct gga cag ggt ctg      192
Thr Ser Tyr Arg Met His Trp Val Arg Gln Ala Pro Gly Gln Gly Leu
    50                  55                  60

gaa tgg att gga tat att aat ccg tcg act ggg tat act gaa tac aat      240
Glu Trp Ile Gly Tyr Ile Asn Pro Ser Thr Gly Tyr Thr Glu Tyr Asn
65                  70                  75                  80

cag aag ttc aag gac aag gca aca att act gca gac gaa tcc acc aat      288
Gln Lys Phe Lys Asp Lys Ala Thr Ile Thr Ala Asp Glu Ser Thr Asn
                85                  90                  95

aca gcc tac atg gaa ctg agc agc ctg aga tct gag gac acc gca gtc      336
Thr Ala Tyr Met Glu Leu Ser Ser Leu Arg Ser Glu Asp Thr Ala Val
            100                 105                 110

tat tac tgt gca aga ggg ggg ggg gtc ttt gac tac tgg ggc caa gga      384
Tyr Tyr Cys Ala Arg Gly Gly Gly Val Phe Asp Tyr Trp Gly Gln Gly
        115                 120                 125
```

-continued

```
acc ctg gtc aca gtc tcc tca gcc tcc acc aag ggc cca tcg gtc ttc      432
Thr Leu Val Thr Val Ser Ser Ala Ser Thr Lys Gly Pro Ser Val Phe
    130                 135                 140

ccc ctg gca ccc tcc tcc aag agc acc tct ggg ggc aca gcg gcc ctg      480
Pro Leu Ala Pro Ser Ser Lys Ser Thr Ser Gly Gly Thr Ala Ala Leu
145                 150                 155                 160

ggc tgc ctg gtc aag gac tac ttc ccc gaa ccg gtg acg gtg tcg tgg      528
Gly Cys Leu Val Lys Asp Tyr Phe Pro Glu Pro Val Thr Val Ser Trp
                165                 170                 175

aac tca ggc gcc ctg acc agc ggc gtg cac acc ttc ccg gct gtc cta      576
Asn Ser Gly Ala Leu Thr Ser Gly Val His Thr Phe Pro Ala Val Leu
            180                 185                 190

cag tcc tca gga ctc tac tcc ctc agc agc gtg gtg acc gtg ccc tcc      624
Gln Ser Ser Gly Leu Tyr Ser Leu Ser Ser Val Val Thr Val Pro Ser
        195                 200                 205

agc agc ttg ggc acc cag acc tac atc tgc aac gtg aat cac aag ccc      672
Ser Ser Leu Gly Thr Gln Thr Tyr Ile Cys Asn Val Asn His Lys Pro
    210                 215                 220

agc aac acc aag gtg gac aag aaa gtt gag ccc aaa tct tgt gac aaa      720
Ser Asn Thr Lys Val Asp Lys Lys Val Glu Pro Lys Ser Cys Asp Lys
225                 230                 235                 240

act cac aca tgc cca ccg tgc cca gca cct gaa ctc ctg ggg gga ccg      768
Thr His Thr Cys Pro Pro Cys Pro Ala Pro Glu Leu Leu Gly Gly Pro
                245                 250                 255

tca gtc ttc ctc ttc ccc cca aaa ccc aag gac acc ctc atg atc tcc      816
Ser Val Phe Leu Phe Pro Pro Lys Pro Lys Asp Thr Leu Met Ile Ser
            260                 265                 270

cgg acc cct gag gtc aca tgc gtg gtg gtg gac gtg agc cac gaa gac      864
Arg Thr Pro Glu Val Thr Cys Val Val Val Asp Val Ser His Glu Asp
        275                 280                 285

cct gag gtc aag ttc aac tgg tac gtg gac ggc gtg gag gtg cat aat      912
Pro Glu Val Lys Phe Asn Trp Tyr Val Asp Gly Val Glu Val His Asn
    290                 295                 300

gcc aag aca aag ccg cgg gag gag cag tac aac agc acg tac cgt gtg      960
Ala Lys Thr Lys Pro Arg Glu Glu Gln Tyr Asn Ser Thr Tyr Arg Val
305                 310                 315                 320

gtc agc gtc ctc acc gtc ctg cac cag gac tgg ctg aat ggc aag gag     1008
Val Ser Val Leu Thr Val Leu His Gln Asp Trp Leu Asn Gly Lys Glu
                325                 330                 335

tac aag tgc aag gtc tcc aac aaa gcc ctc cca gcc ccc atc gag aaa     1056
Tyr Lys Cys Lys Val Ser Asn Lys Ala Leu Pro Ala Pro Ile Glu Lys
            340                 345                 350

acc atc tcc aaa gcc aaa ggg cag ccc cga gaa cca cag gtg tac acc     1104
Thr Ile Ser Lys Ala Lys Gly Gln Pro Arg Glu Pro Gln Val Tyr Thr
        355                 360                 365

ctg ccc cca tcc cgg gat gag ctg acc aag aac cag gtc agc ctg acc     1152
Leu Pro Pro Ser Arg Asp Glu Leu Thr Lys Asn Gln Val Ser Leu Thr
    370                 375                 380

tgc ctg gtc aaa ggc ttc tat ccc agc gac atc gcc gtg gag tgg gag     1200
Cys Leu Val Lys Gly Phe Tyr Pro Ser Asp Ile Ala Val Glu Trp Glu
385                 390                 395                 400

agc aat ggg cag ccg gag aac aac tac aag acc acg cct ccc gtg ctg     1248
Ser Asn Gly Gln Pro Glu Asn Asn Tyr Lys Thr Thr Pro Pro Val Leu
                405                 410                 415

gac tcc gac ggc tcc ttc ttc ctc tac agc aag ctc acc gtg gac aag     1296
Asp Ser Asp Gly Ser Phe Phe Leu Tyr Ser Lys Leu Thr Val Asp Lys
            420                 425                 430

agc agg tgg cag cag ggg aac gtc ttc tca tgc tcc gtg atg cat gag     1344
Ser Arg Trp Gln Gln Gly Asn Val Phe Ser Cys Ser Val Met His Glu
        435                 440                 445
```

```
gct ctg cac aac cac tac acg cag aag agc ctc tcc ctg tct ccg ggt     1392
Ala Leu His Asn His Tyr Thr Gln Lys Ser Leu Ser Leu Ser Pro Gly
    450                 455                 460

aaa tga                                                             1398
Lys
465


<210> SEQ ID NO 4
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Arg Met His Trp Val Arg Gln Ala Pro Gly Gln Gly Leu
    50                  55                  60

Glu Trp Ile Gly Tyr Ile Asn Pro Ser Thr Gly Tyr Thr Glu Tyr Asn
65                  70                  75                  80

Gln Lys Phe Lys Asp Lys Ala Thr Ile Thr Ala Asp Glu Ser Thr Asn
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Gly Val Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320
```

```
Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 5
<211> LENGTH: 10936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gaattctcga gcgcgttaca taacttacgg taaatggccc gcctggctga ccgcccaacg      60

acccccgccc attgacgtca ataatgacgt atgttcccat agtaacgcca atagggactt     120

tccattgacg tcaatgggtg gagtatttac ggtaaactgc ccacttggca gtacatcaag     180

tgtatcatat gccaagtacg ccccctattg acgtcaatga cggtaaatgg cccgcctggc     240

attatgccca gtacatgacc ttatgggact ttcctacttg gcagtacatc tacgtattag     300

tcatcgctat taccatggtg atgcggtttt ggcagtacat caatgggcgt ggatagcggt     360

ttgactcacg gggatttcca agtctccacc ccattgacgt caatgggagt ttgttttggc     420

accaaaatca acgggacttt ccaaaatgtc gtaacaactc cgccccattg acgcaaatgg     480

gcggtaggcg tgtacggtgg gaggtctata taagcagagc tcgtttagtg aaccgtcaga     540

tcgcctggag acgccatcca cgctgttttg acctccatag aagacaccgg gaccgatcca     600

gcctccgcct cgatcgagac gcgtctagac caccatggga tggagctgga tctttctctt     660

cctcctgtca ggtaccgcgg gcgtgcactc tcaggtccag cttgtccagt ctggggctga     720

agtcaagaaa cctggctcga gcgtgaaggt ctcctgcaag gcttctggct acacctttac     780

tagctacagg atgcactggg taaggcaggc ccctggacag ggtctggaat ggattggata     840

tattaatccg tcgactgggt atactgaata caatcagaag ttcaaggaca aggcaacaat     900

tactgcagac gaatccacca atacagccta catggaactg agcagcctga gatctgagga     960

caccgcagtc tattactgtg caagaggggg gggggtcttt gactactggg gccaaggaac    1020

cctggtcaca gtctcctcag gtgagtcctt aaaacctcta gagctttctg gggcaggcca    1080

ggcctgacct tggctttggg gcagggaggg ggctaaggtg aggcaggtgg cgccagccag    1140
```

```
gtgcacaccc aatgcccatg agcccagaca ctggacgctg aacctcgcgg acagttaaga   1200
acccaggggc ctctgcgccc tgggcccagc tctgtcccac accgcggtca catggcacca   1260
cctctcttgc agcctccacc aagggcccat cggtcttccc cctggcaccc tcctccaaga   1320
gcacctctgg gggcacagcg gccctgggct gcctggtcaa ggactacttc cccgaaccgg   1380
tgacggtgtc gtggaactca ggcgccctga ccagcggcgt gcacaccttc ccggctgtcc   1440
tacagtcctc aggactctac tccctcagca gcgtggtgac cgtgccctcc agcagcttgg   1500
gcacccagac ctacatctgc aacgtgaatc acaagcccag caacaccaag gtggacaaga   1560
aagttggtga gaggccagca cagggaggga gggtgtctgc tggaagccag gctcagcgct   1620
cctgcctgga cgcatcccgg ctatgcagcc ccagtccagg gcagcaaggc aggccccgtc   1680
tgcctcttca cccggaggcc tctgcccgcc ccactcatgc tcagggagag ggtcttctgg   1740
ctttttcccc aggctctggg caggcacagg ctaggtgccc ctaacccagg ccctgcacac   1800
aaaggggcag gtgctgggct cagacctgcc aagagccata tccgggagga ccctgcccct   1860
gacctaagcc caccccaaag gccaaactct ccactccctc agctcggaca ccttctctcc   1920
tcccagattc cagtaactcc caatcttctc tctgcagagc ccaaatcttg tgacaaaact   1980
cacacatgcc caccgtgccc aggtaagcca gcccaggcct cgccctccag ctcaaggcgg   2040
gacaggtgcc ctagagtagc ctgcatccag ggacaggccc cagccgggtg ctgacacgtc   2100
cacctccatc tcttcctcag cacctgaact cctgggggga ccgtcagtct tcctcttccc   2160
cccaaaaccc aaggacaccc tcatgatctc ccggacccct gaggtcacat gcgtggtggt   2220
ggacgtgagc cacgaagacc ctgaggtcaa gttcaactgg tacgtggacg gcgtggaggt   2280
gcataatgcc aagacaaagc cgcgggagga gcagtacaac agcacgtacc gtgtggtcag   2340
cgtcctcacc gtcctgcacc aggactggct gaatggcaag gagtacaagt gcaaggtctc   2400
caacaaagcc ctcccagccc ccatcgagaa aaccatctcc aaagccaaag gtgggacccg   2460
tggggtgcga gggccacatg gacagaggcc ggctcggccc accctctgcc ctgagagtga   2520
ccgctgtacc aacctctgtc cctacagggc agccccgaga accacaggtg tacaccctgc   2580
ccccatcccg ggatgagctg accaagaacc aggtcagcct gacctgcctg gtcaaaggct   2640
tctatcccag cgacatcgcc gtggagtggg agagcaatgg gcagccggag aacaactaca   2700
agaccacgcc tcccgtgctg gactccgacg gctccttctt cctctacagc aagctcaccg   2760
tggacaagag caggtggcag caggggaacg tcttctcatg ctccgtgatg catgaggctc   2820
tgcacaacca ctacacgcag aagagcctct ccctgtctcc gggtaaatga gtgcgacggc   2880
cggcaagccc ccgctccccg ggctctcgcg gtcgcacgag gatgcttggc acgtaccccc   2940
tgtacatact tcccgggcgc ccagcatgga aataaagcac ccagcgctgc cctgggcccc   3000
tgcgagactg tgatggttct ttccacgggt caggccgagt ctgaggcctg agtggcatga   3060
gggaggcaga gcgggtccca ctgtccccac actggcccag gctgtgcagg tgtgcctggg   3120
ccgcctaggg tggggctcag ccaggggctg ccctcggcag ggtgggggat ttgccagcgt   3180
ggccctccct ccagcagcac ctgccctggg ctgggccacg ggaagcccta ggagcccctg   3240
gggacagaca cacagcccct gcctctgtag gagactgtcc tgttctgtga gcgccctgtc   3300
ctccgacctc catgcccact cgggggcatg cctagtccat gtgcgtaggg acaggccctc   3360
cctcacccat ctacccccac ggcactaacc cctggctgcc ctgcccagcc tcgcacccgc   3420
atggggacac aaccgactcc ggggacatgc actctcgggc cctgtggagg gactggtgca   3480
```

```
gatgcccaca cacacactca gcccagaccc gttcaacaaa ccccgcactg aggttggccg   3540
gccacacggc caccacacac acacgtgcac gcctcacaca cggagcctca cccgggcgaa   3600
ctgcacagca cccagaccag agcaaggtcc tcgcacacgt gaacactcct cggacacagg   3660
cccccacgag ccccacgcgg cacctcaagg cccacgagcc tctcggcagc ttctccacat   3720
gctgacctgc tcagacaaac ccagccctcc tctcacaagg gtgcccctgc agccgccaca   3780
cacacacagg ggatcacaca ccacgtcacg tccctggccc tggcccactt cccagtgccg   3840
cccttccctg caggatcctg gccttggggg agggggaggc cagaatgact ccaagagcta   3900
caggaggcag gtcagagacc ccactggaca aacagtggct ggactctgca ccataacaca   3960
caatcacagg ggagtgagct ggaattctcg agcgcgttac ataacttacg gtaaatggcc   4020
cgcctggctg accgcccaac gacccccgcc cattgacgtc aataatgacg tatgttccca   4080
tagtaacgcc aatagggact ttccattgac gtcaatgggt ggagtattta cggtaaactg   4140
cccacttggc agtacatcaa gtgtatcata tgccaagtac gccccctatt gacgtcaatg   4200
acggtaaatg gcccgcctgg cattatgccc agtacatgac cttatgggac tttcctactt   4260
ggcagtacat ctacgtatta gtcatcgcta ttaccatggt gatgcggttt tggcagtaca   4320
tcaatgggcg tggatagcgg tttgactcac ggggatttcc aagtctccac cccattgacg   4380
tcaatgggag tttgttttgg caccaaaatc aacgggactt tccaaaatgt cgtaacaact   4440
ccgccccatt gacgcaaatg ggcggtaggc gtgtacggtg ggaggtctat ataagcagag   4500
ctcgtttagt gaaccgtcag atcgcctgga gacgccatcc acgctgtttt gacctccata   4560
gaagacaccg ggaccgatcc agcctccgcc tcgatcgaga cgcgtctaga tggagaccga   4620
taccctcctg ctatgggtcc tcctgctatg ggtcccagga tcaaccggag atattcagat   4680
gacccagtct ccatctaccc tctctgctag cgtcggggat agggtcacca taacctgctc   4740
tgccagctca agtataagtt acatgcactg gtaccagcag aagccaggca aagctcccaa   4800
gcttctaatt tataccacat ccaacctggc ttctggagtc cctgctcgct tcagtggcag   4860
tggatctggg accgagttca ccctcacaat cagctctctg cagccagatg atttcgccac   4920
ttattactgc catcaaagga gtacttaccc actcacgttc ggtcagggga ccaaggtgga   4980
ggtcaaacgt aagtacactt ttctagaaat tctaaactct gagggggtcg gatgacgtgg   5040
ccattctttg cctaaagcat tgagtttact gcaaggtcag aaaagcatgc aaagccctca   5100
gaatggctgc aaagagctcc aacaaaacaa tttagaactt tattaaggaa tagggggaag   5160
ctaggaagaa actcaaaaca tcaagatttt aaatacgctt cttggtctcc ttgctataat   5220
tatctgggat aagcatgctg ttttctgtct gtccctaaca tgctctgtga ttatccgcaa   5280
acaacacacc caagggcaga actttgttac ttaaacacca tcctgtttgc ttctttcctc   5340
aggaactgtg gctgcaccat ctgtcttcat cttcccgcca tctgatgagc agttgaaatc   5400
tggaactgcc tctgttgtgt gcctgctgaa taacttctat cccagagagg ccaaagtaca   5460
gtggaaggtg gataacgccc tccaatcggg taactcccag gagagtgtca cagagcagga   5520
cagcaaggac agcacctaca gcctcagcag caccctgacg ctgagcaaag cagactacga   5580
gaaacacaaa gtctacgcct gcgaagtcac ccatcagggc ctgagctcgc ccgtcacaaa   5640
gagcttcaac aggggagagt gttagaggga gaagtgcccc cacctgctcc tcagttccag   5700
cctgaccccc tcccatcctt tggcctctga ccctttttcc acaggggacc tacccctatt   5760
gcggtcctcc agctcatctt tcacctcacc cccctcctcc tccttggctt taattatgct   5820
aatgttggag gagaatgaat aaataaagtg aatctttgca cctgtggttt ctctctttcc   5880
```

```
tcatttaata attattatct gttgtttacc aactactcaa tttctcttat aagggactaa   5940
atatgtagtc atcctaaggc gcataaccat ttataaaaat catccttcat tctattttac   6000
cctatcatcc tctgcaagac agtcctccct caaacccaca agccttctgt cctcacagtc   6060
ccctgggcca tggtaggaga gacttgcttc cttgttttcc cctcctcagc aagccctcat   6120
agtccttttt aagggtgaca ggtcttacag tcatatatcc tttgattcaa ttccctgaga   6180
atcaaccaaa gcaaattttt caaaagaaga aacctgctat aaagagaatc attcattgca   6240
acatgatata aaataacaac acaataaaag caattaaata aacaaacaat agggaaatgt   6300
ttaagttcat catggtactt agacttaatg gaatgtcatg ccttatttac atttttaaac   6360
aggtactgag ggactcctgt ctgccaaggg ccgtattgag tactttccac aacctaattt   6420
aatccacact atactgtgag attaaaaaca ttcattaaaa tgttgcaaag gttctataaa   6480
gctgagagac aaatatattc tataactcag caatcccact tctaggatcc gggccgcatg   6540
catctcaatt agtcagcaac catagtcccg cccctaactc cgcccatccc gcccctaact   6600
ccgcccagtt ccgcccattc tccgccccat ggctgactaa ttttttttat ttatgcagag   6660
gccgaggccg cctcggcctc tgagctattc cagaagtagt gaggaggctt ttttggaggc   6720
ctaggctttt gcaaaaagct tggacacaag acaggcttgc gagatatgtt tgagaatacc   6780
actttatccc gcgtcaggga gaggcagtgc gtaaaaagac gcggactcat gtgaaatact   6840
ggtttttagt gcgccagatc tctataatct cgcgcaacct atttcccct cgaacacttt    6900
ttaagccgta gataaacagg ctgggacact tcacatgagc gaaaaataca tcgtcacctg   6960
ggacatgttg cagatccatg cacgtaaact cgcaagccga ctgatgcctt ctgaacaatg   7020
gaaaggcatt attgccgtaa gccgtggcgg tctggtaccg ggtgcgttac tggcgcgtga   7080
actgggtatt cgtcatgtcg ataccgtttg tatttccagc tacgatcacg acaaccagcg   7140
cgagcttaaa gtgctgaaac gcgcagaagg cgatggcgaa ggcttcatcg ttattgatga   7200
cctggtggat accggtggta ctgcggttgc gattcgtgaa atgtatccaa aagcgcactt   7260
tgtcaccatc ttcgcaaaac cggctggtcg tccgctggtt gatgactatg ttgttgatat   7320
cccgcaagat acctggattg aacagccgtg ggatatgggc gtcgtattcg tcccgccaat   7380
ctccggtcgc taatcttttc aacgcctggc actgccgggc gttgttcttt ttaacttcag   7440
gcgggttaca atagtttcca gtaagtattc tggaggctgc atccatgaca caggcaaacc   7500
tgagcgaaac cctgttcaaa ccccgcttta aacatcctga aacctcgacg ctagtccgcc   7560
gctttaatca cggcgcacaa ccgcctgtgc agtcggccct tgatggtaaa accatccctc   7620
actggtatcg catgattaac cgtctgatgt ggatctggcg cggcattgac ccacgcgaaa   7680
tcctcgacgt ccaggcacgt attgtgatga gcgatgccga acgtaccgac gatgatttat   7740
acgatacggt gattggctac cgtggcggca actggattta tgagtgggcc ccggatcttt   7800
gtgaaggaac cttacttctg tggtgtgaca taattggaca aactacctac agagatttaa   7860
agctctaagg taaatataaa atttttaagt gtataatgtg ttaaactact gattctaatt   7920
gtttgtgtat tttagattcc aacctatgga actgatgaat gggagcagtg gtggaatgcc   7980
tttaatgagg aaaacctgtt ttgctcagaa gaaatgccat ctagtgatga tgaggctact   8040
gctgactctc aacattctac tcctccaaaa aagaagagaa aggtagaaga ccccaaggac   8100
tttccttcag aattgctaag tttttgagt catgctgtgt ttagtaatag aactcttgct    8160
tgctttgcta tttacaccac aaaggaaaaa gctgcactgc tatacaagaa aattatggaa   8220
```

```
aaatattctg taacctttat aagtaggcat aacagttata atcataacat actgtttttt   8280
cttactccac acaggcatag agtgtctgct attaataact atgctcaaaa attgtgtacc   8340
tttagctttt taatttgtaa aggggttaat aaggaatatt tgatgtatag tgccttgact   8400
agagatcata atcagccata ccacatttgt agaggtttta cttgctttaa aaaacctccc   8460
acacctcccc ctgaacctga aacataaaat gaatgcaatt gttgttgtta acttgtttat   8520
tgcagcttat aatggttaca aataaagcaa tagcatcaca aatttcacaa ataaagcatt   8580
tttttcactg cattctagtt gtggtttgtc caaactcatc aatgtatctt atcatgtctg   8640
gatcctgcct cgcgcgtttc ggtgatgacg gtgaaaacct ctgacacatg cagctcccgg   8700
agacggtcac agcttgtctg taagcggatg ccgggagcag acaagcccgt cagggcgcgt   8760
cagcgggtgt tggcgggtgt cggggcgcag ccatgaccca gtcacgtagc gatagcggag   8820
tgtatactgg cttaactatg cggcatcaga gcagattgta ctgagagtgc accatatgcg   8880
gtgtgaaata ccgcacagat gcgtaaggag aaaataccgc atcaggcgct cttccgcttc   8940
ctcgctcact gactcgctgc gctcggtcgt tcggctgcgg cgagcggtat cagctcactc   9000
aaaggcggta atacggttat ccacagaatc aggggataac gcaggaaaga acatgtgagc   9060
aaaaggccag caaaaggcca ggaaccgtaa aaaggccgcg ttgctggcgt ttttccatag   9120
gctccgcccc cctgacgagc atcacaaaaa tcgacgctca agtcagaggt ggcgaaaccc   9180
gacaggacta taaagatacc aggcgtttcc ccctggaagc tccctcgtgc gctctcctgt   9240
tccgaccctg ccgcttaccg gatacctgtc cgcctttctc ccttcgggaa gcgtggcgct   9300
ttctcaatgc tcacgctgta ggtatctcag ttcggtgtag gtcgttcgct ccaagctggg   9360
ctgtgtgcac gaaccccccg ttcagcccga ccgctgcgcc ttatccggta actatcgtct   9420
tgagtccaac ccggtaagac acgacttatc gccactggca gcagccactg gtaacaggat   9480
tagcagagcg aggtatgtag gcggtgctac agagttcttg aagtggtggc ctaactacgg   9540
ctacactaga aggacagtat ttggtatctg cgctctgctg aagccagtta ccttcggaaa   9600
aagagttggt agctcttgat ccggcaaaca aaccaccgct ggtagcggtg gtttttttgt   9660
ttgcaagcag cagattacgc gcagaaaaaa aggatctcaa gaagatcctt tgatcttttc   9720
tacggggtct gacgctcagt ggaacgaaaa ctcacgttaa gggattttgg tcatgagatt   9780
atcaaaaagg atcttcacct agatcctttt aaattaaaaa tgaagtttta aatcaatcta   9840
aagtatatat gagtaaactt ggtctgacag ttaccaatgc ttaatcagtg aggcacctat   9900
ctcagcgatc tgtctatttc gttcatccat agttgcctga ctccccgtcg tgtagataac   9960
tacgatacgg gagggcttac catctggccc cagtgctgca atgataccgc gagacccacg  10020
ctcaccggct ccagatttat cagcaataaa ccagccagcc ggaagggccg agcgcagaag  10080
tggtcctgca actttatccg cctccatcca gtctattaat tgttgccggg aagctagagt  10140
aagtagttcg ccagttaata gtttgcgcaa cgttgttgcc attgctgcag gcatcgtggt  10200
gtcacgctcg tcgtttggta tggcttcatt cagctccggt tcccaacgat caaggcgagt  10260
tacatgatcc cccatgttgt gcaaaaaagc ggttagctcc ttcggtcctc cgatcgttgt  10320
cagaagtaag ttggccgcag tgttatcact catggttatg gcagcactgc ataattctct  10380
tactgtcatg ccatccgtaa gatgcttttc tgtgactggt gagtactcaa ccaagtcatt  10440
ctgagaatag tgtatgcggc gaccgagttg ctcttgcccg gcgtcaacac gggataatac  10500
cgcgccacat agcagaactt taaaagtgct catcattgga aaacgttctt cggggcgaaa  10560
actctcaagg atcttaccgc tgttgagatc cagttcgatg taacccactc gtgcacccaa  10620
```

```
ctgatcttca gcatctttta ctttcaccag cgtttctggg tgagcaaaaa caggaaggca  10680

aaatgccgca aaaaagggaa taagggcgac acggaaatgt tgaatactca tactcttcct  10740

ttttcaatat tattgaagca tttatcaggg ttattgtctc atgagcggat acatatttga  10800

atgtatttag aaaaataaac aaataggggt tccgcgcaca tttccccgaa aagtgccacc  10860

tgacgtctaa gaaaccatta ttatcatgac attaacctat aaaaataggc gtatcacgag  10920

gccctttcgt cttcaa                                                  10936
```

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

```
Ser Ala Ser Ser Ser Ile Ser Tyr Met His
1               5                   10
```

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

```
Thr Thr Ser Asn Leu Ala Ser
1               5
```

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

```
His Gln Arg Ser Thr Tyr Pro Leu Thr
1               5
```

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

```
Ser Tyr Arg Met His
1               5
```

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

-continued

Tyr Ile Asn Pro Ser Thr Gly Tyr Thr Glu Tyr Asn Gln Lys Phe Lys
1               5                   10                  15

Asp

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Gly Gly Gly Val Phe Asp Tyr
1               5

<210> SEQ ID NO 12
<211> LENGTH: 206
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
gcatgcatct caattagtca gcaaccatag tcccgcccct aactccgccc atcccgcccc     60
taactccgcc cagttccgcc cattctccgc cccatggctg actaattttt tttatttatg    120
cagaggccga ggccgcctcg gcctctgagc tattccagaa gtagtgagga ggcttttttg    180
gaggcctagg cttttgcaaa aagctt                                         206

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Asp Ile Gln Met Thr Gln Ser Pro Ser Thr Leu Ser Ala Ser Val
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Val His Ser Gln Val Gln Leu Val Gln Ser Gly Ala Glu Val Lys
1               5                   10                  15

DAC HYP COMPOSITIONS AND METHODS

1. CROSS REFERENCE TO RELATED APPLICATIONS

The present application is a divisional under 35 U.S.C. & 121 of U.S. application Ser. No. 13/481,081, filed on May 25, 2012, which claims the benefit U.S. Provisional Application No. 61/490,998, filed May 27, 2011. Each of these applications is hereby incorporated by reference in its entirety.

2. SEQUENCE LISTING

The instant application contains a Sequence Listing which has been submitted in ASCII format via EFS-Web and is hereby incorporated by reference in its entirety. Said ASCII copy, created on May 25, 2012, is named 386003US.txt and is 34,217 bytes in size.

3. BACKGROUND

Daclizumab (DAC) is a humanized $IgG_1$ monoclonal antibody that binds to the alpha subunit (CD25 or Tac) of the human high-affinity interleukin-2 (IL-2) receptor, which is expressed on the surface of activated, but not resting, T- and B-lymphocytes. When bound to CD25 on the activated cells, DAC blocks the formation of the high affinity IL-2 receptor complex, thereby blocking IL-2-induced proliferation of the activated cells.

As measured in direct binding assays on PHA blasts, DAC binds to CD25 with an approximate binding affinity ($K_D$) of 0.3 nM, and inhibits the proliferation of PHA blasts in a dose-dependent manner (Hakimi et al., 1993, J. Immunol. 151(2):1075-85). At a suboptimal dose of IL-2 (2.5 ng/mL), 15 nM DAC inhibits proliferation of IL-2-dependent cell line Kit225/K6 by 50% (Pilson et al., 1997, J. Immunol. 159(3):1543-56). In an IL2-dependent antigen-induced T-cell proliferation assay, 50% inhibition of proliferation was observed with DAC in the range of 0.5-1 μg/mL (3-7 nM) (Junghans et al., 1990, Cancer Res. 50(5):1495-502).

A version of DAC was previously marketed for the treatment of acute allograft rejection in renal transplant patients as an adjunct to an immunosuppressive regimen that includes cyclosporine and corticosteroids by Hoffman-La Roche, Inc. under the tradename ZENAPAX™. ZENAPAX was supplied as a concentrate for further dilution and intravenous administration. Each vial of concentrate contained 5 mL of a solution containing 5 mg/mL DAC, 3.6 mg/mL sodium phosphate monobasic monohydrate, 11 mg/mL sodium phosphate dibasic heptahydrate, 4.6 mg/mL sodium chloride, 0.2 mg/mL polysorbate 80 and HCl and/or NaOH sufficient to adjust the pH to pH 6.9. The recommended dose for both adult and pediatric patients was 1.0 mg/kg, prepared by diluting the calculated volume of 25 mg/5 mL ZENAPAX concentrate with 50 mL sterile 0.9% sodium chloride solution and administering intravenously via a peripheral or central vein over a 15-minute period.

DAC has also shown efficacy in the treatment of uveitis (Nussenblatt et al., 2004, FOCIS 2004 meeting; July 18-23, Montreal, QC. Abstract 4688; Nussenblatt et al., 2003, J. Autoimmun. 21:283-93) and multiple sclerosis (see, e.g., Bielekova et al., 2004, Proc. Nat'l. Acad. Sci. USA 101(23): 8705-8708; Rose et al., 2007, Neurology 69:785-789; U.S. Pat. No. 7,258,859), and is currently the subject of ongoing clinical trials for the treatment of multiple sclerosis. Although DAC has proven to be safe and effective, high concentration, liquid formulations that have long shelf lives and that can be conveniently administered without further formulation or manipulation, as well as new daclizumab molecules that have improved properties, such as enhanced safety, as compared to ZENAPAX DAC, would be desirable.

4. SUMMARY

As mentioned in the Background Section, daclizumab is a humanized $IgG_1$ antibody that specifically binds the alpha subunit (also referred to as CD25 or Tac) of the human interleukin-2 receptor (IL-2R), which is an important mediator of lymphocyte activation. A version of daclizumab previously marketed by Hoffman-La Roche under the tradename ZENAPAX™ has demonstrated safety and efficacy in the treatment of renal allograft rejection when used as an adjunct to an immunosuppressive regimen including cyclosporine and corticosteroids (see, e.g., the European Medicines Agency ("EMEA") market authorization for ZENAPAX), and has also demonstrated efficacy in the treatment of multiple sclerosis (see, e.g., Bielekova et al., 2004, Proc. Nat'l. Acad. Sci. USA 101(23):8705-8708; Rose et al., 2007, Neurology 69:785-789; U.S. Pat. No. 7,258, 859). According to EMEA, ZENAPAX DAC is expressed in GS-NS0 (murine myeloma) cells and purified using a process that involves Q-Sepharose chromatography, S-Sepharose chromatography, diafiltration, Q-Sepharose II chromatography, ultrafiltration, S-300 gel filtration chromatography and ultrafiltration. It has now been discovered that daclizumab expressed in an NS0 cell line that has been adapted to grow in serum-free, cholesterol-free and other animal product-free media and that is isolated by a different process has characteristics and properties that are different from, and in some instances, superior to, ZENAPAX daclizumab ("ZENAPAX DAC"). This new daclizumab, referred to herein as DAC HYP, has: a different isoform profile than ZENAPAX DAC (as determined via cation exchange chromatography); a different N-linked glycosylation profile than ZENAPAX DAC, even though both forms of daclizumab are expressed in NS0 cells; and less ADCC cytotoxicity than ZENAPAX DAC in biological assays.

For example, isoforms of daclizumab are possible due to heterogeneity at the heavy chain N- and C-termini. The amino acid sequence of the mature $V_H$ chain of daclizumab begins at position 20 of the amino acid sequence shown in FIG. 2 (SEQ ID NO:4). The N-terminal glutamine (Q) of the mature $V_H$ chain (in bold, underlined text in FIG. 2) can cyclize, forming pyroglutamate (pE). In some instances, the signal peptide sequence may truncate, leaving a valine-histidine-serine (VHS) sequence attached to the N-terminal glutamine residue of the mature $V_H$ chain. Because each daclizumab molecule contains two $V_H$ chains, the various N-terminal isoforms of daclizumab can include forms containing: (1) two glutamine residues (Q/Q); (2) one glutamine residue and one VHS sequence (Q/VHS or VHS/Q); (3) two VHS sequences (VHS/VHS); (4) one glutamine residue and one pyroglutamate residue (Q/pE or pE/Q); (5) one pyroglutamate residue and one VHS sequence (pE/VHS or VHS/pE); and (6) two pyroglutamate residues (pE/pE). Different C-terminal isoforms also are possible, which contain either 0, 1 or 2 C-terminal lysine (K) residues (0K, 1K or 2K), resulting in a complex isoform profile.

Quite surprisingly, while the N-terminal glutamines of the $V_H$ chains of ZENAPAX DAC are completely cyclized to pyroglutamate, complete cyclization is not achieved for DAC HYP. As a consequence, the cation exchange chromatogram of DAC HYP is characterized by a pE/Q isoform peak and a Q/VHS isoform peak. While not intending to be bound by any theory, it is believed that these unique pE/Q and Q/VHS isoforms may be influenced by the leader sequence used to express DAC HYP. Accordingly, in one aspect, the present disclosure provides daclizumab compositions in which the pE/Q isoform ranges from 3%-17%, from 3%-15%, from 5%-15%, more preferably from 5%-12% or 7%-12% of the N-terminal isoforms, and/or in which the Q/VHS isoform ranges from 1%-15%, more preferably 3%-12% of the N-terminal isoforms, as determined by cation exchange chromatography.

In some embodiments, the daclizumab composition is characterized by a cation exchange chromatography profile that is substantially similar to FIG. 18 or the DAC HYP profile of FIG. 23.

Daclizumab has N-linked oligosaccharides attached to heavy chain residue Asn 296. When these N-linked oligosaccharides are released using amidase PNGaseF and analyzed via HPLC, DAC HYP exhibits a glycosylation profile different from ZENAPAX DAC, despite the fact that both are recombinantly produced in NS0 cell lines. Indeed, the glycosylation profile of DAC HYP is unusually homogeneous. Referring to the upper panel of FIG. 21, the glycosylation profile of ZENAPAX DAC is characterized by peaks representing oligosaccharides G0-GlcNAc, G0, G1, Man5, G2, Man6, Man7 and sialylated oligosaccharide. The lower panel of FIG. 21 shows that the glycosylation profile of DAC HYP is characterized by two main peaks corresponding to G0-GlcNAc glycoforms and G0 glycoforms and a minor peak corresponding to a G1 glycoform. The G0-GlcNAc glycoforms can range from about 5% to about 20% of the AUC, more typically about 7.2% to 14.6% of the AUC. The G0 glycoforms can range from 70% to 99.2% of the AUC, more typically from 80.9% to 99.2% of the AUC. The G1 glycoform can range from 1% to 9% of the AUC, more typically from 1.4% to 3.8% of the AUC. Sialylated oligosaccharides are 1.0% of the total AUC or less.

Immunogenicity and high levels of effector function can be problematic for chronically administered drugs. In addition, rapid clearance rates can reduce drug availability. As is well-known by skilled artisans, differences in glycosylation patterns of therapeutic antibodies can give rise to differences in immunogenicity. Antibodies having highly homogeneous glycosylation patterns like DAC HYP may provide beneficial immunogenicity profiles, ADCC levels, and clearance rates. In addition, biologics having more homogeneous glycosylation patterns reduce batch to batch variation and can improve consistency and stability.

Accordingly, in another aspect the present disclosure provides daclizumab compositions that are characterized by a homogeneous N-linked glycosylation profile. In one embodiment, the daclizumab composition is characterized by an N-linked glycosylation profile that includes approximately 5-20% of the total AUC of G0-GlcNAc glycoforms, and in some embodiments approximately 5%-18% or approximately 7-15% (e.g., 7.2%-14.6% or 6.9%-14.7%) of the total AUC of G0-GlcNAC glycoforms (and in some specific embodiments 7.3% of the total AUC of G0-GlcNAc glycoforms), and approximately 70%-99.2% of the total AUC of G0 glycoforms, and in some embodiments approximately 75%-90%, approximately 75-92%, or approximately 81-88% of the total AUC of G0 glycoforms (and in some specific embodiments 86% of the total AUC of G0 glycoforms), as measured by HPLC. Optionally, the G1 peak is less than about 10% of the total AUC, less than about 5%, less than about 4% or less than about 3% of the total AUC and, in certain embodiments, ranges from about 1% to about 4% (e.g., 1.4% to 3.8%) or about 1% to about 3%. The Man5 glycoforms are preferably about 3% of the total AUC or less. In other embodiments, the daclizumab composition is characterized by an HPLC N-linked glycoform profile substantially similar to a profile illustrated in FIG. 19.

In certain aspects, a daclizumab composition of the disclosure is characterized by the sum total of two or more glycoform peaks. In certain embodiments, the daclizumab compositions of the disclosure are characterized by (a) two main peaks corresponding to G0-GlcNAc glycoforms and G0 glycoforms which together range from about 75% to about 100%, from about 80% to about 100%, or about 85% to about 100% of the total AUC and/or (b) peaks corresponding to Man5, Man6, and Man7 glycoforms which together are about 6% of the total AUC or less and/or (c) peaks corresponding to Man6 and Man7 glycoforms which together are about 2% of the total AUC or less. In such embodiments, the percentage of G0-GlcNAc G0, G1, and/or Man5 can be present in the amounts described in the preceding paragraph.

The binding and inhibitory properties of DAC HYP, as well as the functional potency of DAC HYP as evaluated in an assay that measures the inhibition of IL-2-induced proliferation of T-cells, are similar to those of ZENAPAX DAC. However, quite surprisingly, DAC HYP exhibits significantly less ADCC cytotoxicity than ZENAPAX DAC, which is likely due, at least in part, to differences in their non-fucosylated mannose glycosylation levels (see FIG. 21). As shown in FIG. 22A and FIG. 22B, DAC HYP exhibits at least 25% less ADCC cytotoxicity than ZENAPAX DAC as measured in a cellular assay. As will be recognized by skilled artisans, the reduced ADCC cytotoxicity of DAC HYP may be beneficial for indications involving chronic administration where cell death is not desirable, for example, for the treatment of multiple sclerosis or uveitis. In these contexts, where therapy is applied chronically, such as, for example, in the treatment of multiple sclerosis and other non-oncology indications, DAC HYP therapy may be safer than therapy with ZENAPAX™.

Accordingly, in another aspect, the disclosure provides daclizumab compositions that are characterized by exhibiting ADCC cytotoxicity of less than about 30%, 25%, 20%, 15%, 10%, 5%, or even lower, at a concentration of 1 μg/mL as measured in an in vitro assay using an effector to target cell ratio of 25:1, 40:1, 50:1 or 60:1, for example when using Kit225/K6 as a target cell and/or when using PBMC effector cells from 3 or more, 6 or more, 10 or more, or 50 or more healthy donors. In specific embodiments, the disclosure provides daclizumab compositions that are characterized by exhibiting ADCC cytotoxicity ranging from 5-30%, from 10-30%, from 15-30%, from 15-30%, from 5-25%, from 10-25%, from 20-30%, from 15-25%, from 15-35%, or from 20-35% at a concentration of 1 μg/mL as measured in an in vitro assay using an effector to target cell ratio of 25:1, 40:1, 50:1 or 60:1, for example when using Kit225/K6 as a target cell and/or when using PBMC effector cells from 3 or more, 6 or more, 10 or more, or 50 or more healthy donors. The lower levels of ADCC cytotoxicity observed with DAC HYP as compared to ZENAPAX DAC are surprising given that DAC HYP is an $IgG_1$ immunoglobulin and does not contain framework mutations known to reduce ADCC cytotoxicity.

The safety profile of DAC HYP as compared to ZENAPAX DAC may be further improved by the use of a high yield serum free process, that permits the production of a highly pure product free of bovine serum albumin (BSA). Accordingly, the present disclosure provides a daclizumab composition that is free of BSA and/or is the product of a cell culture process in which BSA is not present.

Daclizumab compositions characterized by one or more of the properties discussed above (DAC HYP compositions) can be conveniently obtained via recombinant expression in mammalian cells. While not intending to be bound by any particular theory of operation, it is believed that one or more of the unique characteristics and/or properties discussed above may be due, at least in part, to the use of a high productivity recombinant expression system. This can be achieved by any method, such as by gene amplification using the DHFR, or using a selectable marker gene under the control a weak promoter, preferably in combination with a strong promoter driving the expression of the protein of interest (preferably a secreted protein). Without being bound by theory, it is believed that selection of markers under the control of a weak promoter facilitates the identification of stable transfectants in which the expression vector integrates into a chromosomal region that is transcriptionally active, yielding high expression levels of the protein of interest. In one embodiment, the weak promoter driving the expression of a selectable marker is an SV40 promoter (Reddy et al., 1978, Science 200:494-502) in which the activity of one or both enhancer regions has been reduced or eliminated, such as by partial or complete deletion, optionally in combination with a strong promoter, such as the CMV IE promoter (Boshart et al., 1985, Cell 41(2):521-30), driving expression of the protein of interest.

Accordingly, in another aspect, the disclosure provides vectors useful for generating recombinant cell lines that stably express high levels of a daclizumab such as DAC HYP, in which expression of the selection marker is under the control of an SV40 promoter whose enhancer function has been reduced, such as by partial deletion of one or both enhancer sequences (designated dE-SV40). A specific dE-SV40 promoter sequence that can be used to produce stable expression cell lines is at positions 6536-6735 of vector pHAT.IgG1.rg.dE (SEQ ID NO:5), illustrated in FIG. 3A-FIG. 3D, and in FIG. 3E (SEQ ID NO: 12). Various embodiments of specific vectors that can be used to produce stable expression cell lines are described in U.S. Application No. 61/565,419 filed Nov. 30, 2011 and International Application No. PCT/US11/62720 filed Nov. 30, 2011, incorporated herein by reference.

Generally, vectors useful for expressing a daclizumab such as DAC HYP will include one or more of the features exemplified by pHAT.IgG1.rg.dE (described in Section 7.1 below), such as a promoter. The two chains of daclizumab can be placed under separate transcriptional control but are preferably on the same vector, and their coding regions can be cDNA or genomic DNA containing introns and exons. As an alternative to separate transcriptional control, the two chains can be expressed as a single transcript or a single open reading frame, with their coding regions separated by an internal ribosome entry site or a self-cleaving intein sequence, in which case the heavy and light chain coding sequences are under the control of a single promoter. An exemplary promoter is the CMV IE promoter and enhancer (at positions 0001-0623 and 3982-4604 of pHAT.IgG1.rg.dE (SEQ ID NO:5)). Additional features include transcriptional initiation sites (if absent from the promoter chosen), transcription termination sites, and origins of replication. Examples of such features are illustrated in Table 1, which outlines the components of pHAT.IgG1.rg.dE.

A specific embodiment useful for expressing both heavy and light chains of a daclizumab such as DAC HYP from a single exogenous nucleic acid, in NS0 cells utilizes a selection marker operable in mammalian cells, such as neomycin phosphotransferase (neo'), hygromycin B phosphotransferase (hyd), hygromycin B phosphotransferase (Hph), puromycin-N-acetyltransferase (purd), blasticidin S deaminase (bse), xanthine/guanine phosphoribosyl transferase (gpt), glutamine synthetase (GS) or Herpes simplex virus thymidine kinase (HSV-tk). In a preferred embodiment, the selectable marker in a vector of the disclosure is an *E. coli* guanine phosphoribosyl transferase selectable marker under the control of an enhancer-less SV40 promoter, the encoding sequence of which can be found at positions 6935-7793 of pHAT.IgG1.rg.dE (SEQ ID NO:5) shown in FIG. 3A-FIG. 3D.

In another aspect, the disclosure provides host cells transfected with vectors useful for recombinantly producing daclizumab, such as for example, DAC HYP. The host cell may be any mammalian cell, including, for example, Chinese Hamster Ovary (CHO) cells, NS0 murine myeloma cells, Sp2/0 cells, PER.C6 cells, Vero cells, BHK cells, HT1080 cells, COST cells, WI38 cells, CV-1/EBNA cells, L cells, 3T3 cells, HEPG2 cells, MDCK cells and 293 cells. Once transfected, the vector may integrate into the genome to yield a stable production cell line. Skilled artisans will appreciate that it is undesirable to include animal products in compositions designated for administration to humans. Accordingly, host cells that do not require serum or other animal products for growth (such as, e.g., cholesterol) are preferred. Host cells that require such animal products can be adapted to utilize serum-free and other animal product-free medium. A method for adapting murine myeloma NS0 cells to grow in serum- and cholesterol-free medium is described in Hartman et al., 2007, Biotech. & Bioeng. 96(2):294-306 and Burky et al., 2007, Biotech. & Bioeng. 96(2):281-293.

As will be recognized by skilled artisans, the basal and feed media used to culture cells for recombinant protein production, as well as other variables such as the feeding schedule, growth rate, temperature, and oxygen levels, can affect the yield and quality of the expressed protein. Methods of optimizing these conditions are within the purview of a skilled artisan; exemplary conditions are set forth in the Exemplary Embodiments of the disclosure. Preferably, cells are adapted to grow in media free of cholesterol-, serum-, and other animal-sourced components; in such instances the basal and feed media preferably include defined chemicals that substitute for such components. It has also been discovered that media containing high levels of glucose, e.g., 10-35 g/L glucose, advantageously increase the cell culture productivity. In a specific embodiment, the basal medium has about 10-20 g/L, more preferably about 15 g/L, glucose and/or the feed medium has 22-35 g/L, more preferably around 28 g/L, glucose. The feed medium can be added to the cells according to an escalating feed schedule, as is known in the art, over a period of 8-15 days, 9-13 days, or, most preferably, 10-13 days.

For a DAC HYP expressed in NS0 producer strain 7A11-5H7-14-43, the components of the growth and feed media, and other variables affecting expression and production have been optimized. Accordingly, the disclosure also provides optimized basal media, feed media, feeding schedules and other culturing methods and conditions useful for producing daclizumab in high yield and purity. These media and culturing parameters and methods are described in more detail in Section 7.3.

It has also been discovered that purifying daclizumab from a cell culture utilizing a combination of certain chromatography steps yields purified daclizumab and DAC HYP drug substance compositions and liquid daclizumab and DAC HYP drug formulations that are shelf stable in liquid form at high concentrations, typically at nominal daclizumab or DAC HYP concentrations of at least about 100 mg/mL±10-15% and in some embodiments 150 mg/mL±10-15% (as measured by UV spectroscopy or refractive index).

The stable, high concentration daclizumab drug formulations are generally prepared by exchanging a concentrated daclizumab formulation with exchange buffer having an osmolality in the range of about 267-327 mOsm/kg (e.g., 270-310 mOsm/kg) and a pH in the range of about pH 5.8-6.2 at 25° C. (e.g., 5.9-6.1 at 25° C.) to yield an intermediate formulation, and then diluting the intermediate formulation with polysorbate dilution buffer to yield a stable, high concentration liquid formulation comprising of about 100 mg/mL±10% daclizumab (e.g., DAC HYP), and in some embodiments at least about 150 mg/mL daclizumab (e g., DAC HYP), as measured by UV spectroscopy or refractive index. The dilution buffer is the same as the exchange buffer, but includes about 0-10% (w/v) polysorbate 80, and is used in an amount such that the final, stable, high concentration daclizumab formulation has a calculated polysorbate 80 concentration (nominal concentration) in a range of 0.02-0.04%, in some embodiments about 0.03% (w/v). A variety of different buffering agents and excipients can be included in the exchange and dilution buffers to achieve an osmolality and pH within the defined ranges. A specific, non-limiting example of an exchange buffer suitable for formulating stable, high concentration liquid daclizumab and DAC HYP drug formulations contains about 40 mM succinate and about 100 mM NaCl and has a pH of about 6.0 at 25° C. A specific, non-limiting example of a dilution buffer suitable for use with this exchange buffer contains about 40 mM succinate, about 100 mM NaCl and about 1% (w/v) polysorbate 80 and has a pH of about 6.0 at 25° C. The pH of the final formulation can be adjusted with acid or base to yield an actual pH of about 6.0 at 25° C.

The stable, high concentration liquid daclizumab formulations are characterized by a low level of aggregation, typically containing at least 95% monomer and less than 3% aggregates, sometimes less than 1.5% aggregates, and more usually greater than 99% monomer and less than 0.8% aggregates, as measured by size exclusion chromatography. Other purity characteristics of the high concentration liquid daclizumab drug formulations are described in more detail in Section 7.6.

The high concentration daclizumab drug formulations are also characterized by a long shelf life, being stable against greater than 5% degradation and formation of greater than 3% aggregates (as measured by SDS-PAGE and size exclusion chromatography, respectively) for periods of up to 54 months or longer, for example, for at least 5 years, when stored at 2-8° C., for periods of up to 9 months when stored under accelerated conditions (23-27° C./60±5% relative humidity) and for periods of up to 3 months when stored under stressed conditions (38-42° C./75±5% relative humidity).

As noted above, the stable, high concentration liquid daclizumab formulations can be prepared by diluting an intermediate formulation with polysorbate dilution buffer to yield finished daclizumab drug formulation. Accordingly, in another aspect, the disclosure provides polysorbate-free purified daclizumab (preferably DAC HYP) intermediate formulations containing at least about 150 mg/mL daclizumab, in some embodiments about 170-190 mg/mL daclizumab, that can be diluted with polysorbate dilution buffer to yield a stable, high concentration daclizumab liquid drug formulations as described herein. In a specific embodiment, the concentrated polysorbate-free intermediate formulations nominally contain about 155 mg/mL or about 180 mg/mL daclizumab (preferably DAC HYP), about 40 mM sodium citrate and about 100 mN NaCl, pH 6.0 at 25° C. In a specific embodiment, the concentrated polysorbate-free intermediate formulations nominally contain about 155 mg/mL or about 180 mg/mL daclizumab (preferably DAC HYP), about 40 mM sodium succinate and about 100 mN NaCl, pH 6.0 at 25° C. The daclizumab compositions are characterized by a low level of aggregates, described further below.

It has been discovered that concentrating daclizumab via ultrafiltration induces aggregates to form, which can result in a high concentration daclizumab drug formulation containing unacceptable (e.g., >3%) levels of aggregates. Accordingly, it is preferable to utilize a "polishing" step prior to concentrating the daclizumab drug substance to remove aggregates. The level of acceptable aggregates prior to concentration will depend upon the concentration of the daclizumab drug substance to be concentrated, the desired concentration in the final daclizumab drug formulation, and the acceptable level of aggregates in the final daclizumab drug formulation. For example, if a 150 mg/mL daclizumab formulation containing less than 3% aggregates is desired, and the daclizumab drug substance must be concentrated 10- to 30-fold (e.g., 20-fold) to achieve this finished daclizumab formulation, the daclizumab composition to be concentrated should contain <0.3% aggregates, preferably <0.2% aggregates, and preferably even lower levels, e.g., about 0.1% aggregates.

A variety of known techniques can be used to obtain a starting daclizumab drug substance composition containing acceptable levels of aggregates for concentration into concentrated daclizumab intermediate and final drug formulations as described herein, including, for example, strong cation exchange chromatography and hydrophobic interaction chromatography. However, it has been surprisingly discovered that weak cation exchange chromatography reduces levels of aggregates of daclizumab compositions containing in the range of 4-12 mg/mL daclizumab and up to 2.5% aggregates to extremely low levels, typically to about 0.1% aggregates. The use of weak cationic exchange to remove aggregates is more environmentally friendly than hydrophobic interaction chromatography, which utilizes nitrogen containing solutions (such as ammonium sulfate solutions).

Accordingly, in another aspect, the disclosure provides methods of polishing daclizumab compositions to remove aggregates such that the resulting polished composition generally contains about 4 to 15 mg/mL daclizumab, where 0.3% or less (e.g., 0.2% or less or 0.1% or less) is in aggregate form, as measured by size exclusion chromatography. The method generally involves passing a daclizumab composition containing about 4-10 mg/mL, typically about 8-9 mg/mL, and preferably about 8.5 mg/mL daclizumab and >0.5% aggregates over a weak cation exchange resin in a suitable buffer to adsorb to the daclizumab, and eluting the adsorbed daclizumab with an elution buffer. Useful weak cation exchange resins include, but are not limited to, CM-650M (Tosoh Biosciences), CM-Sepharose, CM-HyperD. The components of the equilibration, washing and elution buffers will depend upon the weak cation exchange resin used, and will be apparent to those of skill in the art. For CM-650M resin (Tosoh Biosciences, part Number 101392), an equilibration and wash buffer containing about 20 mM sodium citrate, pH 4.5 and an elution buffer containing 20 mM sodium citrate and 75 mM sodium sulfate, pH 4.5 works well. The flow rate used will depend upon the choice of resin and size of the column. For a cylindrical column of CM-650M resin having a bed height in the range of about 10-30 cm (e.g., 17-19 cm) and a flow rate in the range of about 50-200 cm/hr (e.g., 90-110 cm/hr, preferably about 100 cm/hr), works well with the chromatography can be carried out at room temperature, or at lower temperature, for examples temperatures ranging from 4°, 10°, 15°, 20° or 25° C. A typical useful temperature range is 18-25° C. (e.g., 18-22° C.).

According to the ZENAPAX EMEA, the purification process for ZENAPAX DAC involves the following twelve steps:

(i) culture broth concentration;
(ii) Q-Sepharose chromatography;
(iii) S-Sepharose chromatography;
(iv) low pH treatment for viral inactivation;
(v) concentration/diafiltration;
(vi) DV50 filtration for virus removal;
(vii) Q-Sepharose II chromatography;
(viii) viresolve chromatography for virus removal;
(ix) concentration by ultrafiltration;
(x) S-300 gel filtration chromatography;
(xi) concentration by ultrafiltration;
(xii) aseptic filling of vials.

This process is inefficient, and provides a low purification yield. It has been discovered that higher yields can be achieved with a process having fewer steps, while at the same time yielding a higher degree of purity, which permits the resultant daclizumab drug substance to be formulated into high concentration drug formulations as described above. Accordingly, the present disclosure also provides improved methods for isolating and/or purifying both daclizumab drug substance and high concentration drug formulations. The process utilizes Protein A affinity chromatography in conjunction with strong anion exchange (Q-Sepharose) chromatography and weak cation exchange (CM-650M) chromatography, permitting continuous flow processing without dilution of process intermediate. The improved method for obtaining purified daclizumab drug substance involves the following steps:

(i) protein A affinity chromatography to isolate daclizumab from other cell culture components;
(ii) low pH viral inactivation;
(iii) strong anion exchange (Q-Sepharose) chromatography to remove DNA;
(iv) weak cation exchange (CM-650M) chromatography to reduce aggregates; and
(v) filtration to remove viruses.

The exact volumes, column sizes and operating parameters will depend, in part, on the scale of purification, as is well-known in the art. Specific volumes, column sizes and operating parameters useful for large-scale purifications are described in Section 7.4.

Crude daclizumab to be purified and optionally formulated via the above methods can be harvested from the cell culture using a variety of conventional means, e.g., microfiltration, centrifugation, and depth filtration directly from bioreactor. However, it has been discovered that crude daclizumab can be conveniently harvested by lowering the pH of the cell culture to approximately pH 5 at a temperature of less than 15° C. to flocculate the cells, which can be removed via centrifugation. In a specific embodiment, crude daclizumab is harvested by lowering the pH of the cell culture to approximately pH 5, chilling the culture to less than 15° C., for example 4° C., for 30-90 minutes, and centrifuging the resultant suspension to remove cells. This process is generally applicable to any cell culture that secretes recombinant proteins into the culture medium, and is not specific to cultures producing daclizumab or therapeutic antibodies. The pH of the culture can be adjusted using a variety of different acids, including weak or strong organic acids, or weak or strong inorganic acids. For daclizumab cultures, it has been discovered that citric acid works well. A concentrated citric acid solution, e.g., a 0.5 M-2 M solution, can be used for adjusting the pH of the culture prior to harvesting.

The purification of DAC HYP is accomplished by use of three chromatography steps, virus inactivation, virus filtration and final ultra filtrations. Protein A affinity chromatography is the first step in the purification process, which clears the majority of process related impurities. To enable the reuse of protein A affinity column, it must be regenerated and sanitized. It has been discovered that aqueous NaOH solution is effective in accomplishing both column regeneration and sanitization. However, the use of NaOH solutions can degrade the protein A resin, increasing overall production costs. It has also been discovered that sanitizing protein A affinity chromatography resins with a solution containing NaOH and benzyl alcohol yields good results and significantly increases the number of purification cycles. Accordingly, the disclosure also provides a sanitization solution and method for regenerating and sanitizing protein A affinity columns and resins. The buffer generally comprises about 100 to 500 mM sodium citrate, about 10 to 30 mM NaOH and about 0.5 to 3% (v/v) of benzyl alcohol, and has a pH in the range of about pH 10 to 13. The buffer may also optionally include other components, such as, for example, salts and/or detergents. Both sodium citrate and benzyl alcohol are important for protecting protein A resin from being destroyed by NaOH and enhancing microbicidal activities. In specific embodiments, the Protein A sanitization buffer contains about 200 mM sodium citrate, about 20 mM NaOH, and about 1% (v/v) benzyl alcohol. As described in Section 7.4.2, sanitization solutions containing benzyl alcohol and sodium hydroxide have beneficial antimicrobial effects, and can be used to sanitize protein A columns in purification processes for any antibody.

The sanitization buffer can be used to sanitize Protein A chromatography resin in a batch-wise process, where the resin is washed with excess (e.g., 1.5-2× volumes) of sanitization buffer followed by incubation for about 30-45 mM. in excess (e.g., 1.5-2× volumes) sanitization buffer, followed by equilibration with equilibration buffer or storage buffer. The sanitization buffer can also be used to sanitize a prepared Protein A chromatography column by washing the column with excess (e.g., 1.5-2× column volumes) sanitization buffer at a suitable flow rate (e.g., ranging from about 110-190 cm/hr, or 135-165 cm/hr), holding the column under conditions of zero flow for about 30-40 min, and then washing the column with equilibration buffer or storage buffer. Suitable equilibration and storage buffers are described in Section 0.

Sanitizing Protein A columns with the sanitization buffers described herein significantly increases the number of purifications for which a single batch of resin can be used. For example, whereas a single batch of Protein A resin typically lasts only about 30 purification cycles when sanitized with conventional NaOH buffers (e.g., 50 mM NaOH, 0.5 M NaCl), Protein A columns sanitized with the sanitization buffers described herein can be used for more than 100 purification cycles. While not intending to be bound by any theory of operation, it is believed that the sanitization buffers described herein in part protect the immobilized Protein A from NaOH-induced degradation, thereby increasing the useful life of the resin. Accordingly, while improvements are expected for all Protein A resins, including those that utilize mutant strains of Protein A designed to be resistant to NaOH degradation (for example MabSuRe resin), the sanitization buffers described herein are especially beneficial when used to sanitize Protein A resins and columns utilizing unmodified immobilized Protein As, or Protein As that have not been engineered to be NaOH stable. The disclosure further provides methods comprising using a protein A affinity resin for more than 30, more than 35 or more than 40 antibody purification runs, and in some instances up to 50 or up to 100 protein purification cycles, comprising conducting the purification runs and washing the resin with a sanitization solution as disclosed herein.

As mentioned above, daclizumab specifically binds CD25 expressed on activated and not resting T and B lymphocytes, and blocks binding of IL-2 to CD25, thereby inhibiting formation of the high affinity IL-2 receptor complex, inhibiting proliferation of the activated T- and B-cells. The DAC compositions and formulations described herein, and in particular the DAC HYP compositions and formulations, likewise specifically bind CD25 and exhibit similar biological properties. The DAC compositions and formulations described herein, and in particular DAC HYP, are therefore useful in any of the assays and therapeutic methods described for daclizumab generally, and ZENAPAX specifically. Accordingly, the present disclosure also provides methods of using the DAC compositions and formulations described herein, and in particular the DAC HYP compositions and high concentration stable liquid formulation, to inhibit proliferation of activated T- and B-cells, both in in vitro applications and in vivo as a therapeutic approach towards the treatment of diseases in which activated T- and/or B-cell proliferation play a role, such as the treatment and prevention of allograft rejection, the treatment of uveitis, and the treatment of multiple sclerosis.

The methods generally involve contacting an activated T- and/or B-cell with an amount of a daclizumab composition or formulation described herein sufficient to inhibit its proliferation.

For methods of treatment, the methods generally involve administering to a subject an amount of a daclizumab composition, for example a DAC HYP composition or a high concentration DAC formulation as described herein, to provide therapeutic benefit. In a specific embodiment, the daclizumab compositions and formulations can be used to treat multiple sclerosis, either alone or in combination with other agents such as interferon beta. The DAC compositions described herein can be administered subcutaneously to a patient from weekly to monthly (e.g., weekly, every two weeks, twice a month, every four weeks or monthly) in doses ranging from 75 mg to 300 mg (e.g., 75 mg, 100 mg, 125 mg, 150 mg, 175 mg, 200 mg, 225 mg, 250 mg, 275 mg or 300 mg) or ranging from 1 mg/kg to 4 mg/kg. The compositions can be provided in prefilled syringes convenient for subcutaneous use, preferably at nominal daclizumab concentrations of 100 mg/mL±10-15% or 150 mg/mL 10-15%. The concentrated DAC compositions can also be diluted for intravenous administration.

5. BRIEF DESCRIPTION OF THE FIGURES

FIG. 1 provides DAC-HYP light chain cDNA (SEQ ID NO:1) and translated amino acid (SEQ ID NO:2) sequences. The bold, underlined aspartate (D) residue is the first amino acid in the properly processed mature protein; the amino acid sequence upstream of this residue corresponds to the signal sequence.

FIG. 2 provides DAC-HYP heavy chain cDNA (SEQ ID NO:3) and translated amino acid sequences (SEQ ID NO:4). The bold, underlined glutamaine (Q) residue is the first amino acid in the properly processed mature protein; the amino acid sequence upstream of this residue corresponds to the signal sequence.

FIG. 3A-FIG. 3D together provide the full nucleotide sequence for vector pHAT.IgG1.rg.dE (SEQ ID NO:5).

FIG. 3E provides a specific embodiment of a dESV40 promoter (SEQ ID NO:12) that can be used to select high yielding producer strains.

FIG. 4A-4B provide a schematic diagram of vector pHAT.IgG1.rg.dE (FIG. 4A), which is derived from pABX.gpt, a vector that can be adapted to express any heavy and light chain genes or even a non-antibody polypeptide (FIG. 4B).

FIG. 5 provides an exemplary production process for DAC HYP.

FIG. 6 demonstrates UV (280 nm), pH and conductivity monitoring of product fractions during protein A affinity chromatography.

FIG. 7 demonstrates UV (280 nm), pH and conductivity monitoring of product fractions during Q-sepharose chromatography.

FIG. 8 demonstrates UV (280 nm), pH and conductivity monitoring of product fractions CM cation exchange chromatography.

FIG. 9 provides a schematic illustration of the DAC HYP ultrafiltration system.

FIG. 10 provides a 0-60 minute DAC HYP peptide map chromatogram. The reference profile is a 100 mg/ml DAC HYP preparation and Batch 1 and Batch 2 correspond to 150 mg/ml DAC HYP preparations.

FIG. 11 provides a 55-115 minute DAC HYP peptide map chromatogram. The reference profile is a 100 mg/ml DAC HYP preparation and Batch 1 and Batch 2 correspond to 150 mg/ml DAC HYP preparations.

FIG. 12 provides a 110-170 minute DAC HYP peptide map chromatogram. The reference profile is a 100 mg/ml DAC HYP preparation and Batch 1 and Batch 2 correspond to 150 mg/ml DAC HYP preparations.

FIG. 13 provides overlaid circular dichroism spectra of DAC HYP 150 mg/ml lots Batch 1 and Batch 2. The reference is a 100 mg/ml preparation of DAC HYP.

FIG. 14A-FIG. 14B provides overlaid zero-order ultraviolet spectra and overlaid second derivative ultraviolet spectra, respectively. The reference profile is a 100 mg/ml DAC HYP preparation and Batch 1 and Batch 2 correspond to 150 mg/ml DAC HYP preparations. All three spectra are present in each of FIG. 14A and FIG. 14B, but appear as a single spectrum once overlaid on one another.

FIG. 15A-FIG. 15B provide full scale and expanded scale size exclusion chromatograms, respectively. The reference profile is a 100 mg/ml DAC HYP preparation and Batch 1 and Batch 2 correspond to 150 mg/ml DAC HYP preparations.

Figure 18:
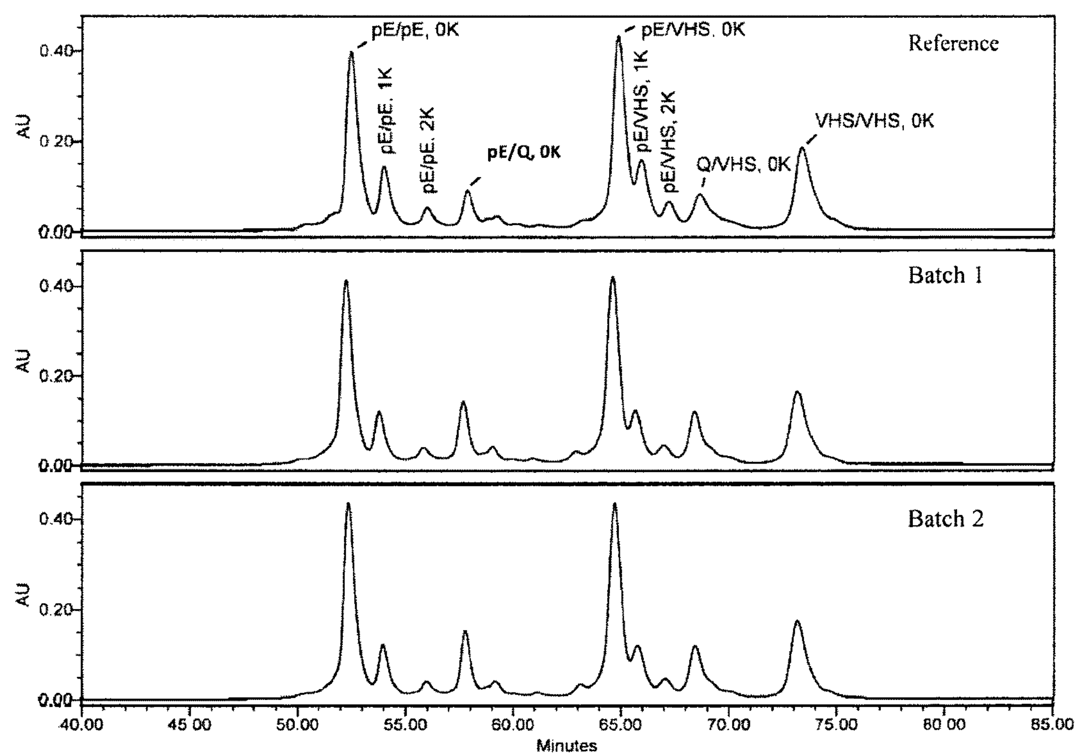

FIG. 18 shows cation exchange chromatograms of DAC HYP. The reference profile is a 100 mg/ml DAC HYP preparation and Batch 1 and Batch 2 correspond to 150 mg/ml DAC HYP preparations. The peak labels correspond to the different N- and C-terminal isoforms.

Figure 19:
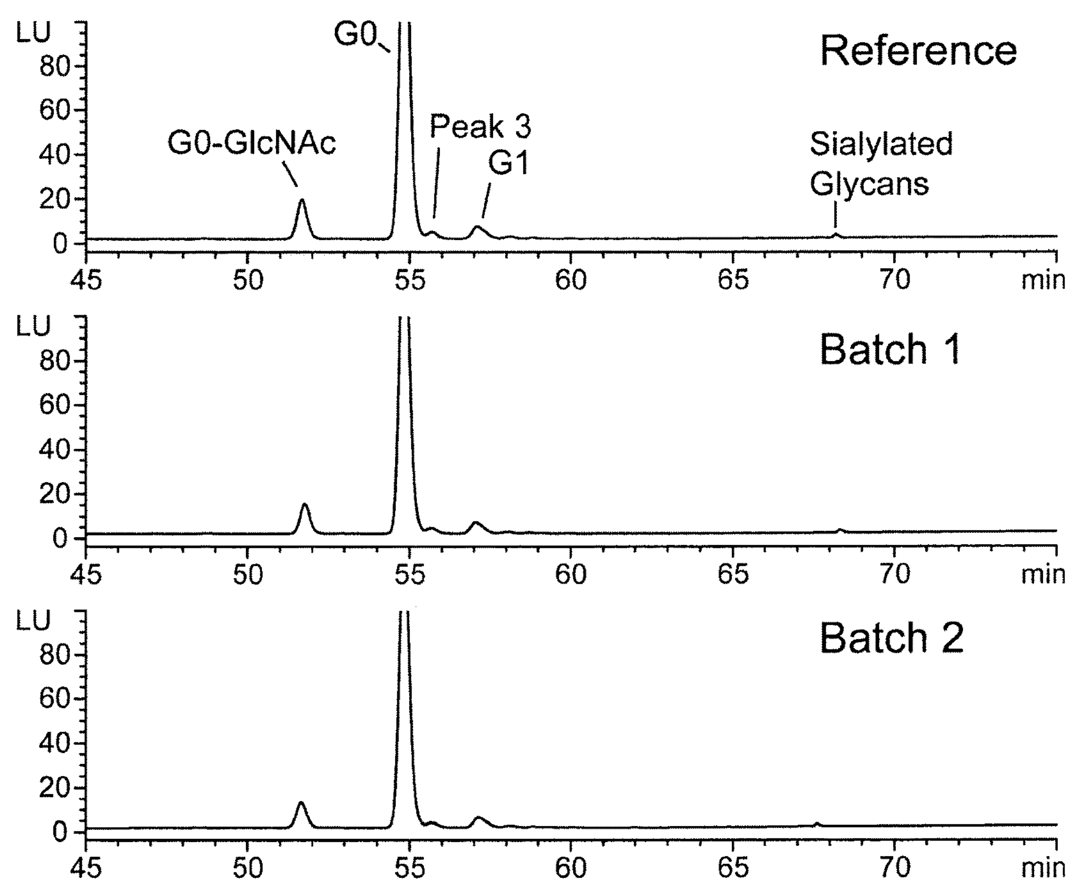

FIG. 19 shows HPLC chromatograms of N-linked oligosaccharides enzymatically cleaved from DAC HYP. The reference profile is a 100 mg/ml DAC HYP preparation and Batch 1 and Batch 2 correspond to 150 mg/ml DAC HYP preparations.

Figure 20:
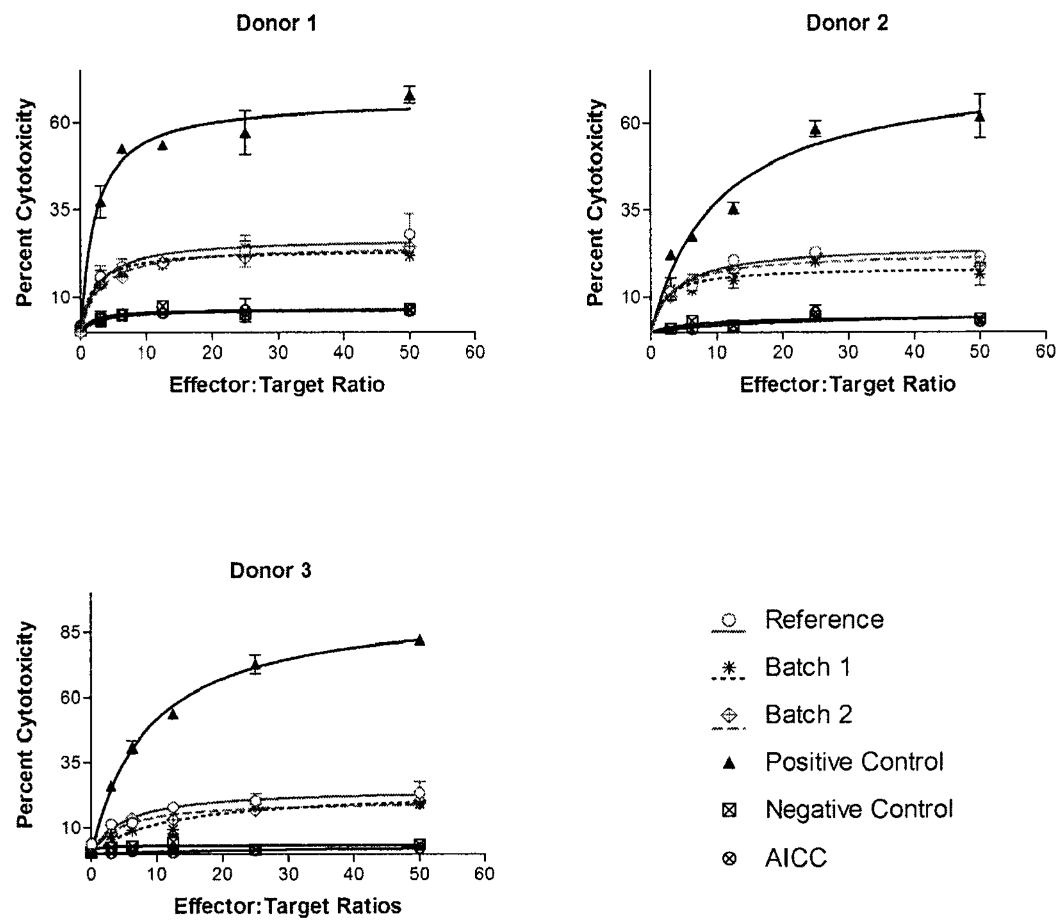

FIG. 20 shows ADCC response curves of DAC HYP. The reference profile is a 100 mg/ml DAC HYP preparation and Batch 1 and Batch 2 correspond to 150 mg/ml DAC HYP preparations.

Figure 21:
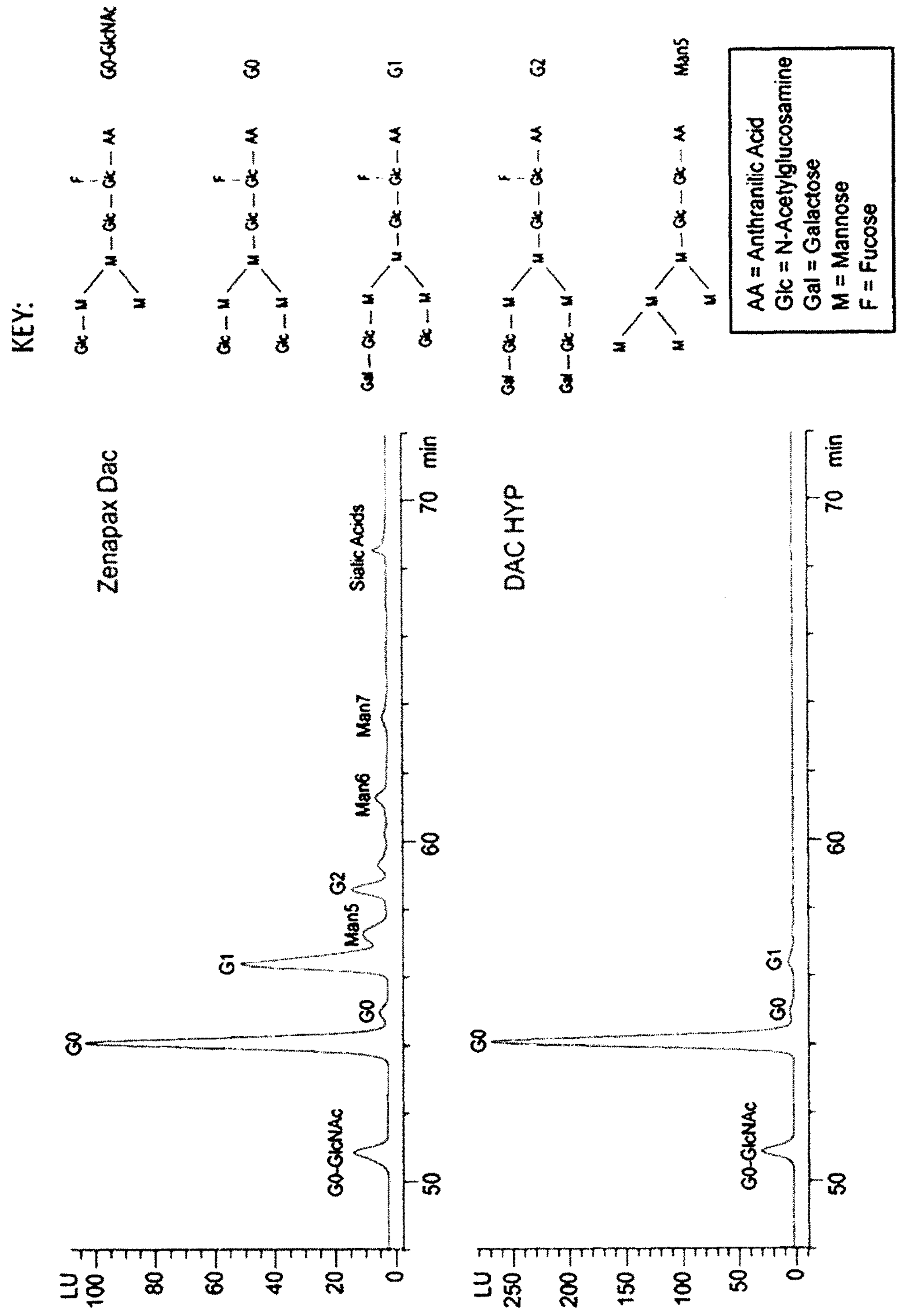

FIG. 21 shows HPLC chromatograms for N-linked oligosaccharides released from DAC HYP (lower panel) and ZENAPAX DAC (upper panel) illustrating their different glycosylation profiles.

Figure 22A:
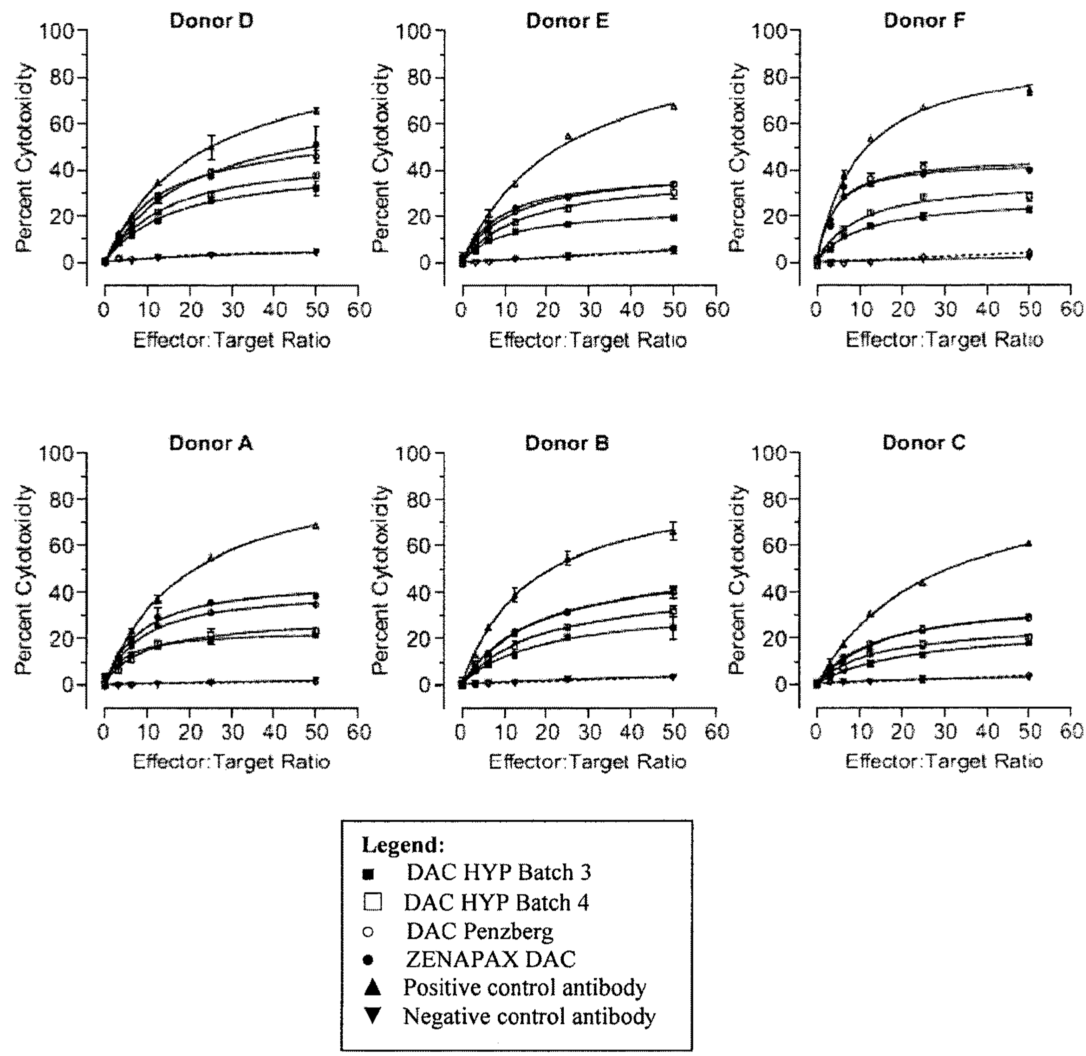
Figure 22B:
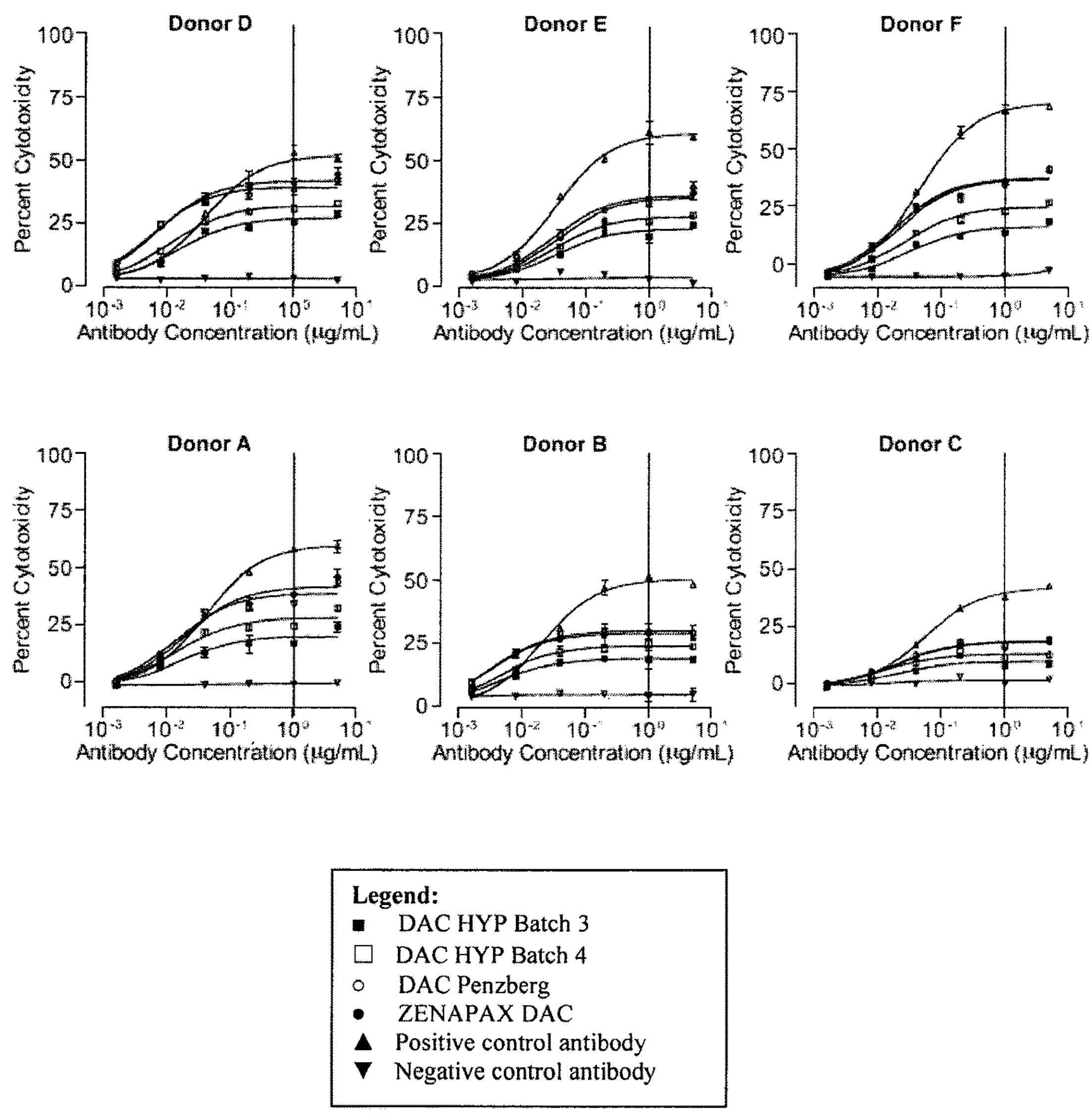

FIG. 22A-FIG. 22B provide a comparison between the ADCC activity of two DAC HYP preparations (referred to as DAC HYP Batch 3 and DAC HYP Batch 4), DAC Penzburg, and ZENAPAX DAC using the variable effector-to-target cell ratio ADCC assay format (FIG. 22A) and the variable antibody concentration ADCC assay format (FIG. 22B).

Figure 23:
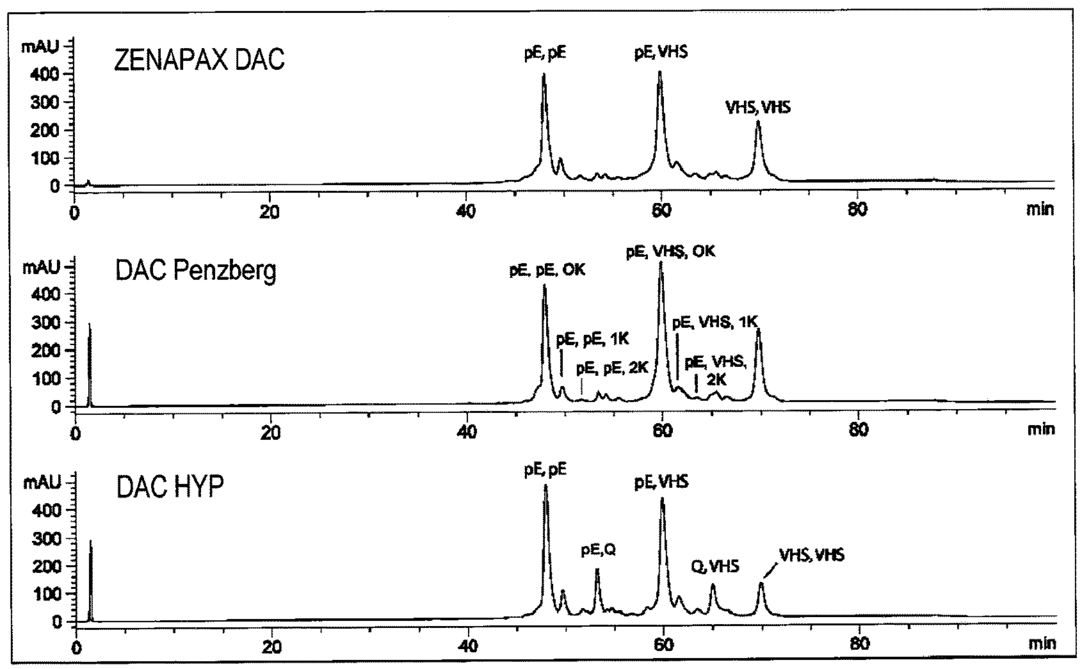

FIG. 23 provides a comparison of the charge isoforms of DAC HYP, DAC Penzberg and ZENAPAX DAC.

6. DETAILED DESCRIPTION

The present disclosure provides, among other things, DAC compositions having specified properties, high concentration DAC formulations especially useful for certain modes of administration that are shelf stable at different temperatures, vectors and host cells useful for producing the DAC compositions, optimized culture broths and culturing conditions useful for producing the DAC compositions, methods for purifying the DAC compositions and high concentration formulations, and methods of using the DAC compositions and high concentration formulations, for example to inhibit proliferation of activated T- and/or B-cells and to treat and/or prevent activated T- and/or B-cell mediated diseases, such as, for example, multiple sclerosis.

Daclizumab (DAC) as used herein refers to a humanized $IgG_1$ monoclonal antibody having the light ($V_L$) chain sequence illustrated in FIG. 1 (positions 21-233 of SEQ ID NO:2) and the heavy ($V_H$) chain sequence illustrated in FIG. 2 (positions 20 to 465 of SEQ ID NO:4). The CDR sequences of DAC are as follows:

$V_L$CDR#1: (SEQ ID NO: 6)

S A S S S I S Y M H $V_L$CDR#2: (SEQ ID NO: 7)

T T S N L A S $V_L$CDR#3: (SEQ ID NO: 8)

H Q R S T Y P L T $V_H$CDR#1: (SEQ ID NO: 9)

S Y R M H $V_H$CDR#2: (SEQ ID NO: 10)

Y I N P S T G Y T E Y N Q K F K D

-continued $V_H$CDR#3: (SEQ ID NO: 11)

G G G V F D Y

Certain daclizumab molecules have been reported in the literature, and a specific version of DAC has been previously marketed under the tradename ZENAPAX by Hoffman-La Roche for the prevention of allograft rejection in renal transplant patients as an adjunct to immunotherapy including cyclosporin and corticosteroids. The version of DAC sold under the tradename ZENAPAX is referred to herein as "ZENAPAX DAC."

Another version of DAC, produced at a facility in Penzberg, Germany, although never sold commercially, has been used in certain clinical trials. This version of DAC is referred to herein as "DAC Penzberg."

As described herein, the present disclosure concerns, in part, a new version of DAC having characteristics and properties that differ from, and in some instances that are superior to, the characteristics and properties of ZENAPAX DAC and DAC Penzberg. Accordingly, the present disclosure in part concerns DAC compositions that are new. The new DAC compositions are characterized by one or more of the following features, as described more fully in the Summary section:

(1) Characteristic pE/Q and/or Q/VHS N-terminal isoforms;

(2) A homogeneous N-linked oligosaccharide profile characterized by two main peaks and a minor peak;

(3) Reduced ADCC cytotoxicity as compared to ZENAPAX DAC and DAC Penzberg; and (4) A low level of aggregate forms (<3%) when formulated at nominal concentrations as high as 150±10-15%.

DAC compositions having one or more of these characteristics and/or properties are referred to herein as "DAC HYP" compositions. For purposes of exemplifying the various aspects and features of inventions described herein, a specific DAC HYP having all four of the above properties is described, as are specific compositions and methods for its production and purification. However, it is to be understood that a DAC HYP composition need not have all of the above four characteristics to fall within the scope of the disclosure. In specific embodiments, DAC HYP has at least two of characteristics (1) through (4) above (e.g., at least a combination of (1) and (2); (1) and (3); (1) and (4); (2) and (3); (2) and (4); or (3) and (4)) or at least three of characteristics (1) through (4) above (e.g., at least a combination of (1), (2) and (3); (1), (2) and (4); (1), (3), and (4); and (2), (3), (4)). Such DAC HYP compositions can also have <3% aggregates, <2% aggregates and even lower levels, e.g., <1% aggregates, when formulated at concentrations of 100 mg±10-15% or even 150±10-15%.

Moreover, while certain aspects and embodiments of the inventions described herein are illustrated and exemplified with DAC HYP, skilled artisans will appreciate that they are not limited to DAC HYP, and are useful for daclizumab compositions generally, and also to $IgG_2$, $IgG_3$, and $IgG_4$ anti-CD25 antibodies having specific CD25 binding properties similar to DAC, and to anti-CD25 antibodies suitable for administration to humans that have not been humanized. These various different anti-CD25 antibodies are referred to herein as "DAC analogs." Such DAC analogs may usually include the six DAC CDRs mentioned above, but may include other CDR sequences.

The characteristics and properties of DAC HYP compositions can be confirmed using standard assays and methods. For example, N-terminal and C-terminal isoform profiles can be assessed using cation exchange chromatography with detection at 220 nm. In a specific method, 100 μL of test sample (1 mg/mL antibody dissolved in Buffer A) is resolved at room temperature on a ProPac WCX-10 column (Dionex Corporation) equipped with a ProPac WCX-10G guard column (Dionex Corporation) using the following separation gradient (column is equilibrated with Buffer A):

| Time (min.) | % Buffer A | % Buffer B | Flow Rate (mL/min) |
|---|---|---|---|
| 0.0 | 100 | 0 | 1 |
| 60.0 | 40 | 60 | 1 |
| 80.0 | 0 | 100 | 1 |
| 85.0 | 0 | 100 | 1 |
| 85.1 | 100 | 0 | 1 |
| 100.0 | 100 | 0 | 1 |

Buffer A = 15 mM sodium phosphate, pH 5.9
Buffer B = 250 mM NaCl, 15 mM sodium phosphate, pH 5

N-linked glycosylation profiles can be assessed by cleaving the N-linked oligosaccharides with amidase PNGase F, derivatizing the oligosaccharides with a fluorescent label and analyzing the resultant mixture via normal phase HPLC with fluorescent detection. In a specific method, anthranilic acid-derivatized, cleaved N-linked glycans are resolved at 50° C. on a 250×4.6 mm polymeric-amine bonded Asahipak Amino $NH_2P$-504E column (5 μm particle size, Phenomenex, cat. No. CHO-2628) using the following elution gradient (using a sample injection volume of 100 μL; column is equilibrated with 85% Buffer A/15% Buffer B):

| Time (min.) | % Buffer A | % Buffer B | Flow Rate (mL/min) |
|---|---|---|---|
| 0 | 85 | 15 | 1 |
| 2 | 85 | 15 | 1 |
| 10 | 80 | 20 | 1 |
| 60 | 55 | 45 | 1 |
| 70 | 5 | 95 | 1 |
| 75 | 5 | 95 | 1 |
| 76 | 85 | 15 | 1 |
| 90 | 85 | 15 | 1 |

Buffer A = 1% v/v tetrahydrofuran, 2% v/v acetic acid in acetonitrile
Buffer B = 1% v/v tetrahydrofuran, 5% v/v acetic acid, 3% v/v triethylamine in water Purity can be confirmed using reduced SDS-PAGE (Precast 14% Tris-Glycine gradient minigels, Invitrogen Part No. 601632) and colloidal blue staining, and/or size exclusion chromatography with detection at 280 nm. In particular, 15 μL test sample (20 mg/mL antibody in elution buffer) can be resolved at room temperature on a 7.8 mm×30 cm TSK G3000SWXL column (Tosoh Biosciences, part no. 601342) equipped with a 0.5 μm pre-column filter (Upchurch, part no. A-102X) using an isocratic gradient of elution buffer (200 mM KPO4, 150 mM KCl, pH 6.9) at a flow rate of 1 mL/min.

The DAC HYP compositions and other DAC formulations described herein, such as the stable, high concentration liquid DAC formulations described herein, are useful for treating a variety of disorders and conditions thought to be mediated, at least in part, by activated T- and/or B-cells, including, for example, rejection of allograft transplants and multiple sclerosis. Specific patient populations, formulations, modes of administration and dosage amounts and schedules useful for treating or preventing allograft rejection are described in U.S. Pat. No. 6,013,256, and are incorporated herein by reference. Specific patient populations, formulations, modes of administration, dosage amounts and schedules useful for treating patients with multiple sclerosis are described in U.S. Pat. No. 7,258,859, and are incorporated herein by reference. All of these formulations, modes of administration, dosing amounts and schedules, as well as disclosed specific patient populations and combination therapies, are equally suited to the DAC HYP compositions and, where applicable, the high concentration DAC formulations, described herein.

The DAC HYP compositions and formulations described herein are administered in amounts that provide therapeutic benefit. Therapeutic benefit includes, but is not limited, treatment of the underlying disorder. Therapeutic benefit may also include improving or ameliorating symptoms or side effects of a particular disease as assessed using standard diagnostic and other tests. For multiple sclerosis, various means of assessing therapeutic benefit, including, for example, the use of magnetic resonance imaging to assess brain lesions and/or assessing progression to disability are described in U.S. Pat. No. 7,258,859, incorporated herein by reference. All of these various tests can be used to assess therapeutic benefit in the context of patients suffering from multiple sclerosis.

The stable high concentration DAC formulations, whether made with DAC HYP, DAC generally or a DAC analog, are particularly useful for subcutaneous administration in the treatment of chronic diseases such as multiple sclerosis. The formulations can conveniently be administered as a single bolus subcutaneous injection or diluted for intravenous administration. The formulations can be administered subcutaneously to a patient from weekly to monthly (e.g., weekly, every two weeks, twice a month, every four weeks or monthly) in doses ranging from 75 mg to 300 mg (e.g., 75 mg, 100 mg, 125 mg, 150 mg, 175 mg, 200 mg, 225 mg, 250 mg, 275 mg or 300 mg) or ranging from 1 mg/kg to 4 mg/kg. The compositions can be provided in prefilled syringes convenient for subcutaneous use. The diluted formulations can be administered intravenously at suitable dosages at the same frequencies as for subcutaneous administration.

7. EXEMPLARY EMBODIMENTS

Various aspects and features of the inventions described herein are described further by way of the exemplary embodiments, below. It will be appreciated that while the exemplary embodiments utilize specific cell culture media, cell culture conditions, column chromatography resins and equilibration, washing and elution buffers, routine changes can be made. Moreover, while the various cell culturing methods are exemplified with a specific producer strain (clone 7A11-5H7-14-43, also referred to as Daclizumab dWCB IP072911), it is expected that other DAC or DAC analog producer strains could be used with success, with or without routine optimization. Moreover, features that are described in association with a particular embodiment (whether in the Summary above or in the Exemplary Embodiments that follow) can be deviated from without substantially affecting the desirable properties of the methods and compositions of the disclosure, and moreover that different embodiments can be combined and used in various ways together unless they are clearly mutually exclusive. Accordingly, it is to be understood that the exemplary embodiments provided below are intended to be illustrative and not limiting, and should not be construed as limiting the claims that follow these embodiments.

The manufacturing method exemplified below was used to produce a DAC HYP drug substance at 150 mg/mL. For making a DAC HYP drug substance at 100 mg/mL, small process changes are introduced:

The cell culture used to produce a DAC HYP (see Section 7.3) at 100 mg/mL does not include an antifoam emulsion, whereas the cell culture DAC HYP at 150 mg/mL uses a low concentration Dow Corning Antifoam C in the 10,000 L bioreactor to minimize foaming. The CM-650M column (see Section 7.4.5) is sanitized with a buffer of 0.5 M NaOH, 0.5 M sodium sulfate when producing a DAC HYP formulation having a final antibody concentration of 100 mg/mL; the sodium sulfate is omitted from the sanitization buffer when producing a DAC HYP formulation having a final antibody concentration of 150 mg/mL. For making DAC HYP at 100 mg/mL, a one step ultrafiltration/diafiltration (UF/DF) is used at the end of the downstream process immediately prior to addition of polysorbate 80 and dilution of the drug substance to final volume (see Section 7.4.7), whereas for making the drug substance at a concentration to 150 mg/mL, a two step UF/DF is used.

the binding affinity were identified and substituted for the human counterpart in the acceptor frameworks. In addition, atypical amino acids in the acceptor frameworks were replaced with the human consensus residues of the corresponding positions to eliminate potential immunogenicity.

Figure 4A:
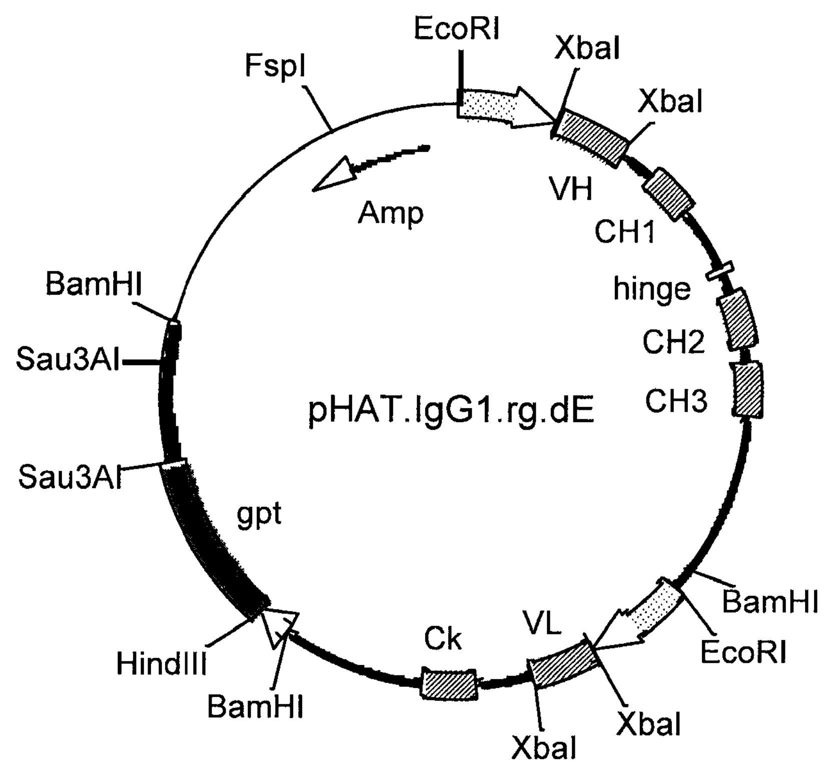
Figure 4B:
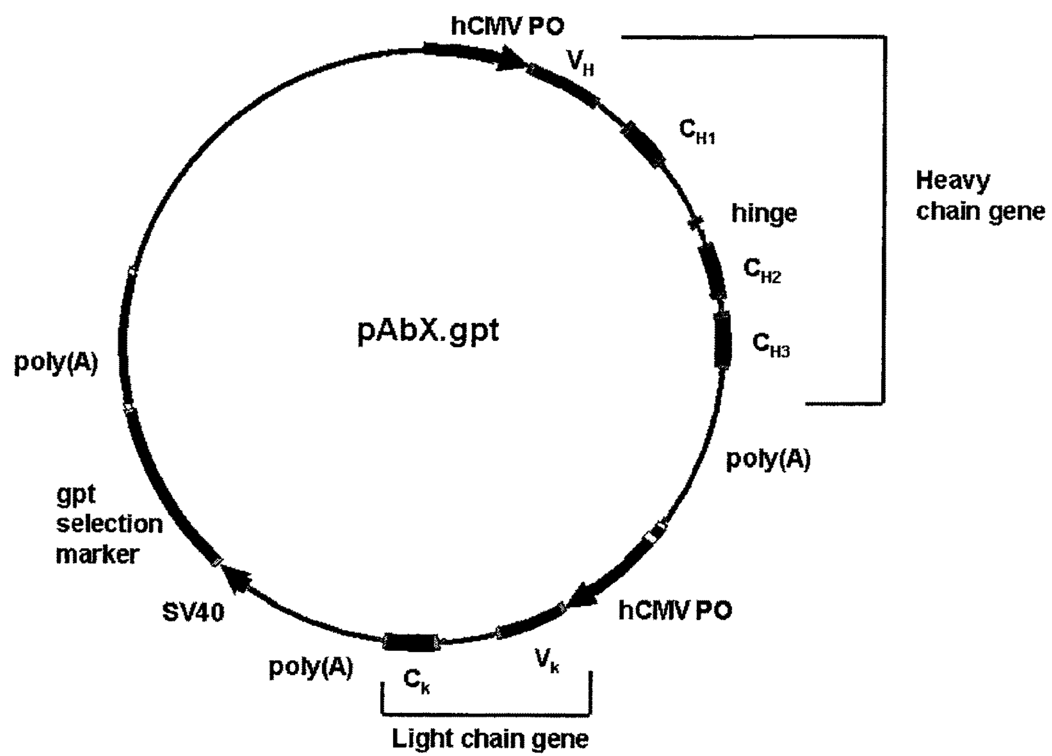

DAC HYP $V_L$ and $V_H$ genes were constructed as mini-exons by annealing and extension of overlapping oligonucleotides as described in Queen et al. (1989). For expression of DAC HYP in the $IgG_1$ form, the resultant $V_L$ and $V_H$ genes were cloned into a single expression vector, as outlined in Cole et al. (1997, J. Immunol. 159(7):3613-21) and Kostelny et al. (2001, Int. J. Cancer 93(4):556-65), to construct pHAT.IgG1.rg.dE (see FIG. 3 and FIG. 4A). Plasmid pHAT.IgG1.rg.dE contains the genes for both the $IgG_1$ heavy and kappa light chains of daclizumab, each under control of the human cytomegalovirus (CMV) promoter. The plasmid contains the *E. coli* guanine phosphoribosyl transferase (gpt) gene as a selectable marker. The genetic components in pHAT.IgG1.rg.dE are described in Table 1 below.

TABLE 1

Genetic Components of pHAT.IgG1.rg.dE

| Nucleotide Number | Restriction Sites in Vector | Description | Reference |
|---|---|---|---|
| 0001-0623 | EcoRI-XbaI | CMV IE enhancer and promoter | Boshart et al., 1985, Cell 41(2):521-30 |
| 0624-1056 | XbaI-XbaI | DAC HYP $V_H$ | |
| 1057-3852 | XbaI-BamHI | Human Cγ1 | Ellison et al., 1982, Nucleic Acids Res. 10(13):4071-79 |
| 3853-3981 | BamHI-EcoRI | Transcription termination site from human complement gene C2 | Ashfield et al., 1991, EMBO J. 10(13):4197-207 |
| 3982-4604 | EcoRI-XbaI | CMV IE enhancer and promoter | Boshart et al., 1985, Cell 41(2):521-30 |
| 4605-5001 | XbaI-XbaI | DAC HYP $V_L$ | |
| 5002-6524 | XbaI-BamHI | Human CK | Hieter et al., 1980, Cell 22(1 Pt 1):197-207. |
| 6525-6735 | BamHI-HindIII | SV40 enhancer and promoter | Reddy et al., 1978, Science 200:494-502 |
| 6736-7793 | HindIII-Sau3AI | *E. coli* gpt gene | Richardson et al., 1983, Nucleic Acids Res. 11(24):8809-16 |
| 7794-8403 | Sau3AI-Sau3AI | SV40 intron | Reddy et al., 1978, Science 200:494-502 |
| 8404-8639 | Sau3AI-BamHI | SV40 poly A | Reddy et al., 1978, Science 200:494-502 |
| 8640-10936 | BamHI-EcoRI | pBR322 region including amp gene | Sutcliffe, 1979, Cold Spring Harb Symp Quant Biol. 43 Pt 1:77-90 |

The examples below show comparative analyses among various lots of DAC HYP at 100 mg/mL and at 150 mg/mL. In several studies, batch of DAC HYP at 150 mg/mL were compared against a lot of DAC HYP 100 mg/mL manufactured at the 10,000 L scale, referred to below as Reference Standard lot RS0801.

7.1. DAC HYP Expression Construct

The hybridoma producing anti-Tac, a murine $IgG_{2a}$ monoclonal antibody, was generated by fusing the murine myeloma cell line NS-1 with spleenocytes from a mouse immunized with a human T-cell line developed from a T-cell leukemia patient (Uchiyama et al., 1981, J. Immunol. 126 (4):1393-7). Anti-Tac was selected for its reactivity with activated T-cells, but not with resting T-cells or B-cells. Anti-Tac was later shown to react with the alpha subunit of human IL-2 receptor (Leonard et al., 1982, Nature 300 (5889):267-9).

The amino acid sequences for the light and heavy chain variable regions of the murine anti-Tac were determined from the respective cDNA (Queen et al., 1989, Proc. Nat'l Acad. Sci. USA 86(24):10029-33). The binding affinity of the mouse anti-Tac was retained in the humanized form as described in Queen et al. The complementarity determining regions (CDRs) of the murine anti-Tac were first grafted onto the acceptor framework of human antibody Eu. With the aid of a three-dimensional model, key mouse framework residues critical for the conformation of the CDRs and thus The dESV40 promoter spans positions of 6536-6735 of pHAT.IgG1.rg.dE (6536-6562 is 27 residues of 72 bp enhancer A; 6566-6629 are the three 21-bp repeats. 6536-6735 are the reverse complement of 5172-1 and 1-133 in GenBank: J02400.1 (Simian Virus 40 Complete Genome)). The nucleotide sequences of DAC HYP light and heavy chain genes in the expression vector were confirmed by DNA sequencing.

7.2. DAC HYP Stable Cell Line

Mouse myeloma cell line NS0 was obtained from European Collection of Cell Cultures (ECACC catalog #85110503, Salisbury, Wiltshire, UK). A vial of these NS0 cells was thawed into DMEM supplemented with 10% FBS. Cells were maintained in a humidified incubator at 37° C. and 7.5% $CO_2$. The cells were subsequently cultured in basal medium SFM-3 supplemented with 1 mg/mL BSA. SFM-3 is a 1:1 mixture of DMEM and Ham's F-12 supplemented with 10 mg/mL insulin and 10 μg/mL transferrin. Over a period of approximately 3 months, the NS0 cells were adapted to SFM-3 without supplements, by gradually reducing the amount of FBS present in the culture medium until it was eliminated, and then finally removing BSA in a single step. The resulting host cell line was passaged 15-20 times in SFM-3 and a frozen bank was prepared.

The SFM-3 adapted cells were transfected with pHAT.IgG1.rg.dE (linearized with FspI enzyme (New England Biolabs, cat. no. R0135L, lot 43)) by electroporation.

Briefly, 30-40 μg of pHAT.IgG1.rg.dE was added to $1\times10^7$ exponentially growing adapted NS0 cells and pulsed twice at 1.5 kV, 25 μF using a Gene Pulser instrument (BioRad, Richmond, Calif.). Following electroporation, cells were plated in DMEM±10% FBS in five 96-well plates at 20,000 cells/well, a density that favored a single colony per well after mycophenolic acid ("MPA") selection. As described in Hartman et al., 2007, Biotech. & Bioeng 96(2):294-306, transfectants that had stably integrated the vector were selected in the presence of mycophenolic acid. Starting from an NS0 stable transfectant that produced a high level of DAC HYP, three successive rounds of subcloning were performed by either limited dilution cloning or fluorescence activated cell sorting (FACS) into PFBM-1 containing either 2.5% or 5% fetal bovine serum (FBS; HyClone, Logan, Utah). At each round of subcloning, one of the best producers was used for the next round of subcloning. Following the third round of subcloning, the final production cell line (7A11-5H7-14-43, also referred to as Daclizumab dWCB IP072911) was chosen. A seed bank of the final production cell line was then prepared by freezing $1\times10^7$ cells per vial in 1 mL of 90% FBS/10% DMSO (Sigma, St. Louis, Mo.).

7.3. DAC HYP Recombinant Production 7.3.1. Cell Culture and Recovery

Cells are thawed from a single cell bank vial and expanded in progressively larger volumes within T-flasks, roller bottles, spinner flasks, and bioreactors until the production scale is achieved. Upon completion of the production culture, the cell culture fluid is clarified by centrifugation and depth filtration, and transferred to a harvest hold tank. The production culture duration is approximately 10 days.

Cell culture and recovery can be carried out in a variety of different cell culture facilities using standard equipment, as is known in the art. In another example, cells are thawed from a single cell bank vial and expanded in progressively larger volumes within shaker flasks and bioreactors until the production scale is achieved. Upon completion of the production culture, the cell culture fluid is clarified by centrifugation and depth filtration, and transferred to a harvest hold tank. The production culture duration is approximately 10 days.

7.3.1.1. Inoculum Preparation

Production batches are initiated by thawing a single cell bank vial. Cells are transferred to a T-flask containing a chemically-defined medium, Protein Free Basal Medium-2 (PFBM-2). Custom Powder for making PFBM-2 can be ordered from Invitrogen by requesting Hybridoma-SFM media powder prepared without NaCl, phenol red, transferrin, and insulin, including a quantity of EDTA iron (III) sodium salt that, when reconstituted, yields a concentration of 5 mg/L, and that has quantities of the remaining components adjusted such that, when reconstituted, their concentrations are the same as reconstituted Hybridoma-SFM. Prepared PFBM-2 medium contains the following components: 8 g/L Custom Powder; 2.45 g/L sodium bicarbonate; 3.15 g/L NaCl; and 16.5 g/L D-glucose monohydrate (15 g/L glucose).

The cells are expanded by serial passage into roller bottles or spinner flasks every two days thereafter. T-flasks, roller bottles, and spinner flasks are placed in an incubator operating under a temperature set point of 37° C. under an atmosphere of 7.5% $CO_2$ for T-flasks and roller bottles and 5% $CO_2$ for spinner flasks.

The spinner flasks are supplemented with 5% $CO_2$ either by overlay into the headspace or by sparge into the culture, depending on the cell culture volume, and impeller speed is controlled at constant revolutions per minute (RPM). The target seeding density at all inoculum expansion passages is approximately $2.5\times10^5$ viable cells/mL.

Furthermore, inoculum preparation can be carried out according to methods known in the art, using a variety of standard culture vessels, volumes, and conditions. For example, production batches can be initiated by thawing a single cell bank vial. Cells can be transferred to a shaker flask containing a chemically-defined medium, Protein Free Basal Medium-2 (PFBM-2). Custom Powder for making PFBM-2 can be ordered from Invitrogen by requesting Hybridoma-SFM media powder prepared without NaCl, phenol red, transferrin, and insulin, including a quantity of EDTA iron (III) sodium salt that, when reconstituted, yields a concentration of 5 mg/L, and that has quantities of the remaining components adjusted such that, when reconstituted, their concentrations are the same as reconstituted Hybridoma-SFM. Prepared PFBM-2 medium contains the following components: 8 g/L Custom Powder; 2.45 g/L sodium bicarbonate; 3.15 g/L NaCl; and 16.5 g/L D-glucose monohydrate (15 g/L glucose). Optionally, at the bioreactor stage, cupric sulfate heptahydrate can be added, e.g., at a concentration of 0.04 mg/L.

The cells are expanded by serial passage into shaker flasks every two days thereafter. Shaker flasks are placed in an incubator operating under a temperature set point of 37° C. under an atmosphere of 7.5% $CO_2$.

The shaker flasks are agitated at constant revolutions per minute (RPM) on a shaker platform in the incubators. The target seeding density at all inoculum expansion passages is approximately $2.2\text{-}2.5\times10^5$ viable cells/mL.

Approximately 14 days following cell bank thaw, when a sufficient number of viable cells have been produced, the first of several, typically three or four, stainless steel stirred-tank seed bioreactors is inoculated. Prior to use, the seed bioreactors are cleaned-in-place, steamed-in-place, and loaded with the appropriate volume of PFBM-2 culture medium. The pH and dissolved oxygen probes are calibrated prior to the bioreactor being steamed-in-place. The first seed bioreactor is inoculated with a sufficient number of cells to target an initial cell density of $2.0\text{-}2.5\times10^5$ viable cells/mL. Sequential transfer to the larger volume (typically, 100 L to 300 L and then to the 1,000 L seed bioreactors, or 60 L to 235 L, 950 L, and 3750 L seed bioreactors) is performed following approximately two days of growth in each reactor and target initial cell densities of $2.0\text{-}2.5\times10^5$ viable cells/mL. Culture pH is maintained by addition of either $CO_2$ gas or 1 M sodium carbonate ($Na_2CO_3$) via automatic control. The target operating conditions of the seed and production bioreactors include a temperature set point of 37° C., pH 7.0 and 30% dissolved oxygen (as a percentage of air saturation). The 100 L, 300 L and 1,000 L bioreactors are agitated at 100 rpm, 80 rpm and 70 rpm, respectively. In some instances, the target operating conditions of the seed and production bioreactors include a temperature set point of 37° C., a pH of 7.0 with $CO_2$ sparge and base addition control and 30% dissolved oxygen (as a percentage of air saturation). The larger volume bioreactors can be agitated at speeds of 100 rpm, 80 rpm, 70 rpm, or 40 rpm.

7.3.2. Cell Culture Production Bioreactor

After approximately 2 days in the 1,000 L seed bioreactor, the inoculum is transferred into a stainless steel stirred-tank production bioreactor. The production bioreactor has a working volume of approximately 10,000 L. Prior to use, the bioreactor is cleaned-in-place, steamed-in-place, and loaded with approximately 4,000 L of PFBM-2 medium. The pH and dissolved oxygen probes are calibrated prior to the bioreactor being steamed-in-place.

In another example, the inoculum is grown in a 3750 L seed bioreactor before transfer to a stainless steel stirred-tank production bioreactor with a working volume of approximately 15,000 L, which is cleaned-in-place, steamed-in-place, and loaded with approximately 4,000-7,000 L of PFBM-2 medium prior to use.

The target seeding density of the production bioreactor is in the range of 2.0-2.5×$10^5$ viable cells/mL. A chemically-defined Protein Free Feed Medium concentrate (PFFM-3) (a chemically-defined concentrated feed medium made by reconstituting PFFM3 subcomponents 1 and 2, L-glutamine, D-glucose, sodium phosphate dibasic heptahydrate, L-tyrosine, folic acid, hydrochloric acid, and sodium hydroxide) is added during culture. PFFM3 contains the components shown in Table 4:

TABLE 4

| PFFM3 Medium Components | |
|---|---|
| Component | Concentration |
| PFFM3 Subcomponent 1 (amino acids) | 20.4 g/L prepared |
| PFFM3 Subcomponent 2 (vitamins and trace elements) | 4.93 g/L prepared |
| L-Glutamine | 11.0 g/L prepared |
| D-Glucose | 28.0 g/L prepared |
| L-Tyrosine, disodium salt | 1.32 g/L prepared |
| Folic Acid | 0.083 g/L prepared |
| $Na_2HPO_4$•$7H_2O$ | 1.74 g/L prepared |
| Sodium Hydroxide | Varies, pH control |
| Glacial Hydrochloric Acid | Varies, pH control |
| WFI water | |

PFFM3 Subcomponent 1 contains the components shown in Table 5 below:

TABLE 5

| PFFM3, Subcomponent 1 | | | |
|---|---|---|---|
| Medium Components | MW (g/mole) | Conc. (mg/L) | Conc. (mM) |
| L-Arginine HCl | 211. | 1,900 | 9.00E+00 |
| L-Asparagine Anhydrous | 132.1 | 1,320 | 9.99E+00 |
| L-Aspartic Acid | 133.1 | 119 | 8.94E−01 |
| L-Cysteine HCl•$H_2O$ | 176.0 | 2,030 | 1.15E+01 |
| L-Glutamic Acid | 147.1 | 510 | 3.47E+00 |
| Glycine | 75.1 | 157 | 2.09E+00 |
| L-Histidine HCl•$H_2O$ | 210.0 | 864 | 4.11E+00 |
| L-Isoleucine | 131.2 | 1,440 | 1.10E+01 |
| L-Leucine | 131.2 | 3,130 | 2.39E+01 |
| L-Lysine HCl | 183.0 | 2,160 | 1.18E+01 |
| L-Methionine | 149.2 | 1,260 | 8.45E+00 |
| L-Phenylalanine | 165.2 | 918 | 5.56E+00 |
| L-Proline | 115.1 | 806 | 7.00E+00 |
| L-Serine | 105.1 | 709 | 6.75E+00 |
| L-Threonine | 119.1 | 1,220 | 1.02E+01 |
| L-Tryptophan | 204.2 | 408 | 2.00E+00 |
| L-Valine | 117.1 | 1,450 | 1.24E+01 |

PFFM3 Subcomponent 2 contains components shown in Table 6 below:

TABLE 6

| PFFM3, Subcomponent 2 | | | |
|---|---|---|---|
| Medium Components | MW (g/mole) | Conc. (mg/L) | Conc. (mM) |
| Vitamin B-12 | 1,355.0 | 10.72 | 7.91E−03 |
| Biotin | 244.0 | 0.156 | 6.39E−04 |
| Choline Chloride | 140.0 | 140 | 1.00E+00 |
| I-Inositol | 180.0 | 197 | 1.09E+00 |
| Niacinamide | 122.0 | 31.5 | 2.58E−01 |
| Calcium Pantothenate | 477.0 | 103.1 | 2.16E−01 |
| Pyridoxine Hydrochloride | 206.0 | 0.484 | 2.35E−03 |
| Thiamine Hydrochloride | 337.0 | 99.8 | 2.96E−01 |
| Putrescine 2HCl | 161.1 | 6.66 | 4.13E−02 |
| DL-Lipoic thioctic acid | 206.0 | 4.84 | 2.35E−02 |
| Sodium Pyruvate | 110.0 | 1,716 | 1.56E+01 |
| Ethanolamine HCl | 97.54 | 76.1 | 7.80E−01 |
| β-Mercaptoethanol | 78.13 | 60.9 | 7.80E−01 |
| Linoleic Acid | 280.48 | 0.655 | 2.34E−03 |
| Pluronic F-68 | 8,350.0 | 780 | 9.34E−02 |
| Potassium Chloride | 74.55 | 432 | 5.79E+00 |
| Riboflavin | 376.0 | 3.42 | 9.09E−03 |
| Magnesium Chloride Anhyd. | 95.21 | 446 | 4.69E+00 |
| Magnesium Sulfate Anhyd. | 120.4 | 762 | 6.33E+00 |
| Sodium Selenite | 172.9 | 0.140 | 8.12E−04 |
| Cupric Sulfate•$5H_2O$ | 249.7 | 0.1069 | 4.28E−04 |
| Ferrous Sulfate•$7H_2O$ | 278.0 | 6.51 | 2.34E−02 |
| Potassium Nitrate | 101.1 | 0.593 | 5.86E−03 |
| Zinc Sulfate•$7H_2O$ | 287.5 | 15.0 | 5.23E−02 |
| Manganese Sulfate, Monohydrate | 169.01 | 0.00264 | 1.56E−05 |
| Nickelous Chloride, 6-Hydrate | 237.7 | 0.00186 | 7.81E−06 |
| Stannous Chloride $2H_2O$ | 225.63 | 0.001130 | 5.01E−06 |
| Ammonium Molybdate $4H_2O$ | 1,235.86 | 0.00193 | 1.57E−06 |
| Ammonium meta-Vanadate | 116.98 | 0.00913 | 7.80E−05 |
| Sodium meta-Silicate $9H_2O$ | 284.2 | 2.22 | 7.79E−03 |
| EDTA, Iron(III), Sodium Salt | 367.05 | 31.2 | 8.50E−02 |

The timing and amount of addition of PFFM-3 to the culture occurs as shown in Table 7 below:

TABLE 7

| Exemplary DAC HYP Bioreactor Feed Schedule | |
|---|---|
| Day | PFFM-3 Amount (% of initial mass) |
| 0 | 0 |
| 1 | 0 |
| 2 | 4-4.14 |
| 3 | 7.8-8.08 |
| 4 | 7.8-8.08 |
| 5 | 7.8-8.08 |
| 6 | 11-11.38 |
| 7 | 13-13.46 |
| 8 | 15-15.52 |
| 9 | 15-15.52 |
| 10 | 0 |

Culture pH is maintained at approximately pH 7.0, preferably between pH 7.0 and pH 7.1, by automatic control of $CO_2$ gas and 1 M sodium carbonate ($Na_2CO_3$) addition. Dissolved oxygen content is allowed to drop to approximately 30% of air saturation. An oxygen/air mixture is sparged into the culture to achieve a constant total gas flow rate and dissolved oxygen is controlled by adjusting the ratio of air to oxygen gases as needed and by increasing agitation speed after reaching a maximum oxygen to air ratio. In another example, agitation is adjusted to maintain a constant power/volume ratio. A simethicone-based antifoam emulsion is added to the bioreactor on an as needed basis based on foam level. Samples are taken periodically to test for cell density, cell viability, product concentration, glucose and lactate concentrations, dissolved $O_2$, dissolved $CO_2$, pH, and osmolality. The bioreactor culture is harvested approximately 10 days post-inoculation. Prior to harvest, the bioreactor contents are sampled as unprocessed bulk.

7.3.3. Harvest and Cell Removal

Just prior to harvest, the production bioreactor is first chilled to <15° C., then adjusted to a pH of 5.0±0.1 using 0.5 M or 1 M or 2 M citric acid, and held for a period of approximately 30-90 or 45-60 minutes to flocculate the cells and cell debris prior to transfer to the harvest vessel. The pH-adjusted harvest is then clarified by continuous centrifugation operated under predefined parameters for bowl speed and flow rate as defined in batch record documentation.

The centrate is filtered through a depth filter followed by a 0.22 μm membrane filter and collected in a pre-sterilized tank. The cell-free harvest is adjusted to an approximate pH of 6.4 using a 1-2 M Tris solution and stored at 2-8° C. for further processing. In some instances, this pH adjustment occurs within 12 hours of the original bioreactor pH adjustment to pH 5.0.

7.4. DAC HYP Purification 7.4.1. Overview

Figure 5:
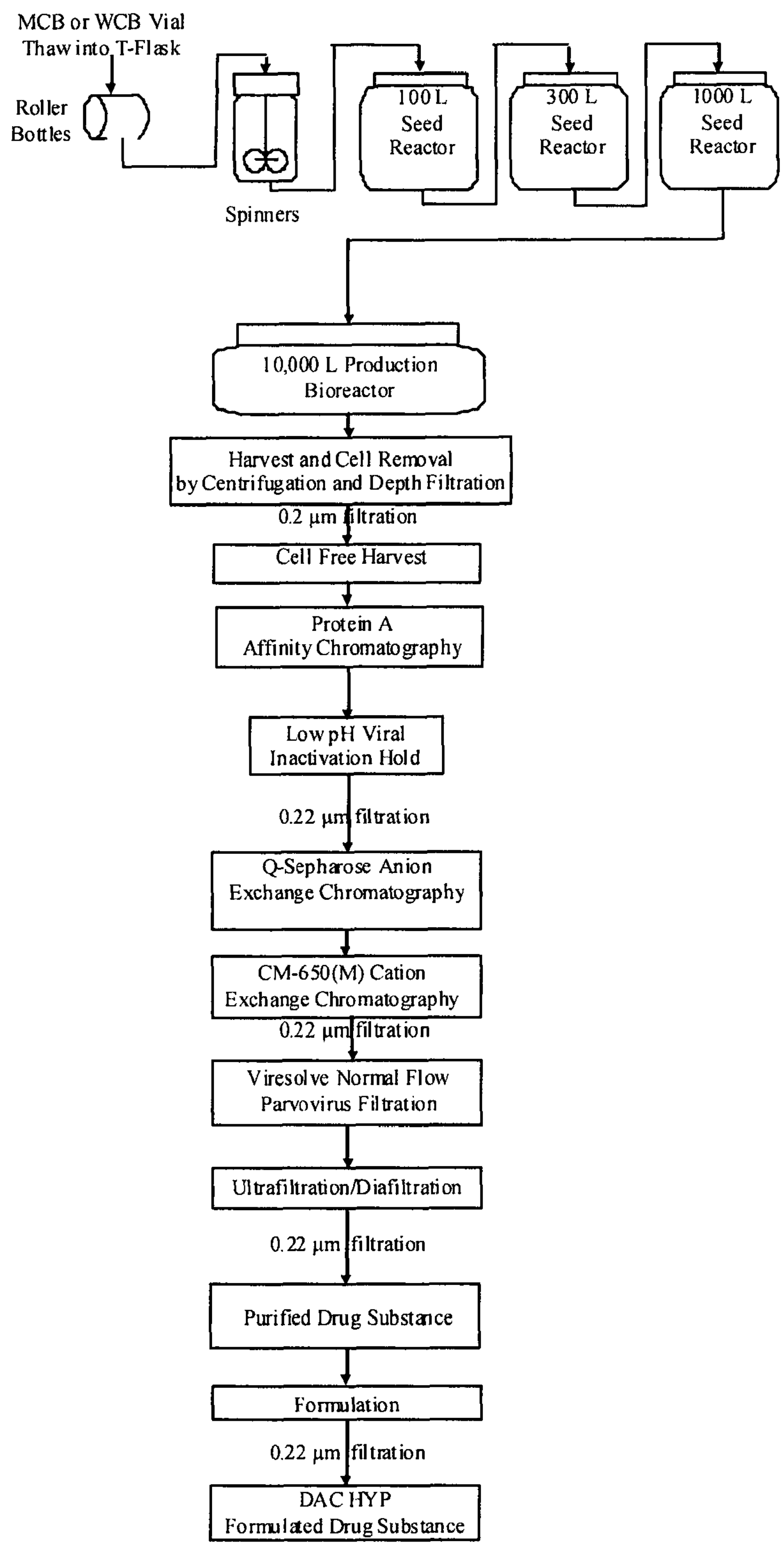

The DAC HYP purification and formulation process was designed to improve efficiency relative to the ZENAPAX production process and to ensure consistent clearance of product- and process-related impurities. The following subsections describe the purification process. The purification is based on three chromatography techniques (Protein A affinity chromatography, Q Sepharose anion exchange chromatography, and CM-650(M) cation exchange chromatography) in combination with low pH viral inactivation, viral filtration, ultrafiltration/diafiltration, and formulation steps. All of the steps take place in enclosed equipment. An outline of the purification process for DAC HYP is presented in FIG. 5 and described below.

7.4.2. Protein A Chromatography

The Protein A affinity chromatography step is the first purification step in the sequence of downstream operations. This step occurs in one or more cycles depending on the size of the column, typically two or three cycles for the column described in Table 8A (i.e., the cell-free harvest is portioned into two aliquots, and then each aliquot is loaded and eluted separately on the Protein A column). Recombinant Protein A affinity chromatography resin specifically binds IgG, separating antibody from other components of the cell culture harvest.

Following equilibration of the Protein A column with an equilibration buffer, the neutralized, cell-free harvest is passed through the column in order to bind the antibody to the column resin. The equilibration buffer is 20 mM sodium citrate, 150 mM sodium chloride, pH 7.0. The column is loaded to a capacity of no greater than 35 grams antibody (protein) per liter of the packed resin. Following loading, the column is washed with the equilibration buffer to remove the unbound and loosely bound impurities from the resin, as well as a pre-elution wash with a citrate buffer to adjust the citrate and sodium chloride concentration of the column. The citrate buffer is 10 mM sodium citrate pH 7.0. The bound antibody is then eluted from the column with a step change in pH using an elution buffer of 10 mM sodium citrate at pH 3.5. A summary of the Protein A chromatography conditions is set forth in Table 8A:

TABLE 8A

Exemplary DAC HYP Protein A chromatography parameters

| PARAMETER | SET POINT |
|---|---|
| Resin | MabSelect |
| Column bed height, cm | 10-25, typically 14 |
| Column diameter, cm | 1-120, depending on scale |
| Operation temperature | 5° C. |
| Equilibration/wash buffer | 20 mM NaCitrate, 150 mM NaCl, pH 7.0 |
| Equilibration volume, CV | 5-7 |
| Equilibration flow rate, cm/hr | 150-300 |
| Load flow rate, cm/hr | 150-300 |
| Load capacity, grams IgG/L resin | <35 |
| Wash flow rate, cm/hr | 150-300 |
| Wash volume, CV | 7 |
| Pre-Elution conditioning | Follow 7 CV wash with 2 CV of 10 mM NaCitrate, pH 7.0 and flow rate of 150-300 cm/hr |
| Elution buffer | 10 mM NaCitrate, pH 3.5 |
| Elution flow rate, cm/hr | 150-300 |
| Collection criteria | 250 mAU-250 mAU (UV detector path-length: 5.0 mm) |
| Elution buffer volume post elution, CV | 2 |
| Flow direction, equilibration, sanitization and storage | Down |
| Equilibration | 20 mM NaCitrate, 150 mM NaCl, pH 7.0 |
| Equilibration volume, CV | 2-3 |
| Equilibration flow rate, cm/hr | 150-300 |
| Sanitization buffer | 200 mM NaCitrate, 20 mM NaOH, 1% Benzyl Alcohol |
| Sanitization flow rate, cm/hr | 150 cm/hr for 1.8 CV, then hold for 30 mins. |
| Equilibration for next cycle | 5-7 CV |
| Storage buffer | 200 mM sodium citrate, 1% benzyl alcohol, pH 7.0 |
| Storage flow rate, cm/hr | 150-300 |
| Storage buffer volume, CV | 4 CV |
| Column Storage temp, ° C. | 5° C. |

Figure 6:
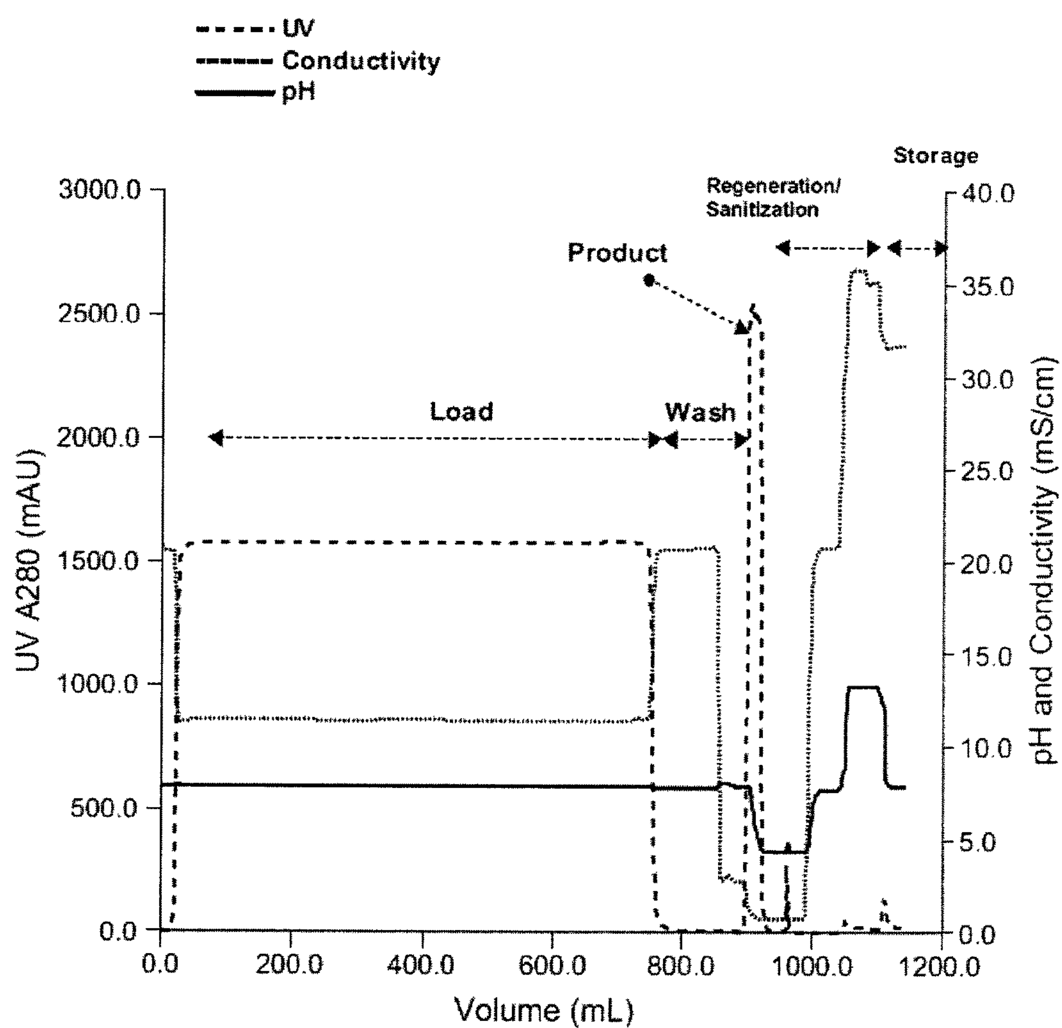

As the product elutes off the column, the absorbance of the effluent at a wavelength of 280 nm is monitored and used to guide the collection of the product fraction (see FIG. 6).

The use of a sanitization buffer containing sodium hydroxide and benzyl alcohol advantageously kills a wide range of microbial organisms while minimally affecting the quality of the protein A resin. To illustrate this, various sanitization solutions were spiked with various microorganisms and incubated over a period of time. At different intervals of incubation time, portions of the spiked sanitization solutions were neutralized and the microorganism titers were measured and compared to control. The microbicidal activities are expressed in the log reduction of the microorganisms over a period of time. Table 8B shows the reduction of microorganism titers as function of contact time with sanitization buffer 20 mM sodium hydroxide, 200 mM sodium citrate and 1% benzyl alcohol:

TABLE 8B

Reduction of microorganism titers as function of contact time with sanitization buffer 20 mM sodium hydroxide, 200 mM sodium citrate and 1% benzyl alcohol

| Organism | LRV@ 0 min | LRV@ 15 min | LRV@ 30 min | LRV@ 60 min | LRV@ 120 min |
|---|---|---|---|---|---|
| *E. coli* (Gram negative) | >5.7 | >5.7 | >5.7 | >5.7 | >5.7 |
| *S. aureus* (Gram positive) | 1.1 | >5.1 | >5.1 | >5.1 | >5.1 |
| *B. subtilis* (spore forming) (Gram negative) | 2.8 | 2.7 | 3.2 | 3.1 | 3.6 |
| *P. aeruginosa* (Gram negative) | >5.0 | >5.0 | >5.0 | >5.0 | >5.0 |

TABLE 8B-continued

| Reduction of microorganism titers as function of contact time with sanitization buffer 20 mM sodium hydroxide, 200 mM sodium citrate and 1% benzyl alcohol | | | | | |
|---|---|---|---|---|---|
| Organism | LRV@ 0 min | LRV@ 15 min | LRV@ 30 min | LRV@ 60 min | LRV@ 120 min |
| *C.albicans* (yeast) | 4.2 | >5.5 | >5.5 | >5.5 | >5.5 |
| *A. niger* (fungus) | −0.2 | 0.4 | 0.5 | 0.8 | 1.4 |

Table 8 C shows the reduction of microorganisms by different sanitization solutions:

TABLE 8C

| $Log_{10}$ Reduction of microorganisms by different solutions | | | | |
|---|---|---|---|---|
| | A | B | C | D |
| *E. coli* | >3.6 | >5.7 | | >4.0 |
| *S. aureus* | >3.6 | 6.0 | 0.5 | >4.0 |
| *Micrococcus lylae* | | 3.3 | | |
| *Bacillus* sp. (spore forming) | | | | |
| *B. subtilis* | −0.3 | 3.1 | 0.2 | 0.12 |
| *Paenibacillus glucanolyticus* | −0.01 | | | −0.03 |
| *B. cereus* | | 5.0 | | |
| *Pseudomonas* sp. | | | | |
| *P. aeruginosa* | >3.6 | | | >4.6 |
| *Stenotrophomonas altophilia* | | 6.0 | | |
| *Candida albicans* (Yeast) | 3.1 | >5.5 | 0 | >4.8 |
| *Aspergillus niger* | 0.01 | 0.8 | 0 | >4.7 |

A = 50 mM NaOH, 0.5M NaCl (60 min)
B = 20 mM NaOH, 200 mM sodium citrate, 1% benzyl alcohol (60 min)
C = 200 mM sodium citrate, 0.5% benzyl alcohol (48 hrs)
D = 2% benzyl alcohol (24 hrs)

The forgoing data shows that sanitization solutions containing benzyl alcohol and sodium hydroxide are very effective in killing a wide variety of microorganisms, including gram negative and gram positive bacteria, spore forming bacteria, yeast and fungus. After 30 minutes of typical sanitization, more than 5 $\log_{10}$ reductions were observed on *E. coli, Staphylococcus aureus, Pseudomonas aeruginosa*, and *Candida albicans*. Although the killing of fungus (*A. niger*) took longer, it is rare to have fungus infection in the cell culture fluids. The most common microorganisms isolated in biotech facility are *Bacillus, Pseudomonas* and *Staphylococcus*. These are effectively killed by the sanitization solution after 30 minutes of contact time. In comparison, sodium hydroxide or benzyl alcohol alone are not effective in killing all the microorganisms. Moreover, the sodium hydroxide sanitization solution does not kill spore forming *Bacillus*.

7.4.3. Low pH Hold for Viral Inactivation

This step is designed to inactivate low pH-sensitive endogenous virus-like particles and viruses. The Protein A eluate from each Protein A cycle is eluted into a collection tank, where 0.5 M HCl is added until a pH 3.5±0.1 is reached. The product is transferred to a hold tank where the pH is verified by another pH meter. The low pH hold step is tightly controlled at pH 3.5±0.1 or ±0.2 (e.g., pH 3.35-3.64) for 30-120 minutes, or 30-240 minutes. After 30-120 minutes hold, the viral inactivated eluate is neutralized to a pH of 7.8±0.1 or ±0.3 (e.g., pH 8.05-8.34) using 1 M Tris base, and then transferred through a 0.22 μm filter into a product pool tank. A summary of the low pH viral inactivation conditions is set forth in the Table 9:

TABLE 9

| DAC HYP low pH viral inactivation parameters | |
|---|---|
| PARAMETER | SET POINT |
| Inactivation pH | 3.5 |
| Dilution of eluate | Dilute to <13 mg/mL and above tank sample point |
| Dilution buffer | 17 mM NaCl or elution buffer |
| pH adjustment buffer | 0.5M HCl |
| Inactivation time | 120 min at 5° C. or 30 min at ambient temp. |
| Neutralization Buffer | 1M Tris |
| Post Neutralization pH Target | 7.8 measured at 25° C.* |

*Alternatively, the post-neutralization pH target can be 8.2 at 25° C..

7.4.4. Q Sepharose Anion Exchange Flow Through Chromatography

The Q Sepharose anion exchange chromatography step is used to reduce product- and process-related impurities (e.g., nucleic acids, host cell proteins, product aggregates, leached Protein A ligand, etc.) and to provide additional viral clearance capacity to the purification process. The conductivity and pH of the load are chosen in a manner such that the antibody flows through the column and negatively-charged impurities, such as host cell proteins and cellular DNA, bind to the positively-charged resin.

The anion exchange column is equilibrated with an equilibration buffer of 20 mM Tris, 20 mM sodium chloride, pH 7.8. The pH-adjusted product from the low pH hold step is loaded onto the column to a capacity of no greater than 60 grams of antibody (protein), or no greater than 30-60 grams of antibody (protein), per liter of packed resin. Following the completion of loading, unbound antibody and impurities are removed from the column with the equilibration buffer.

Figure 7:
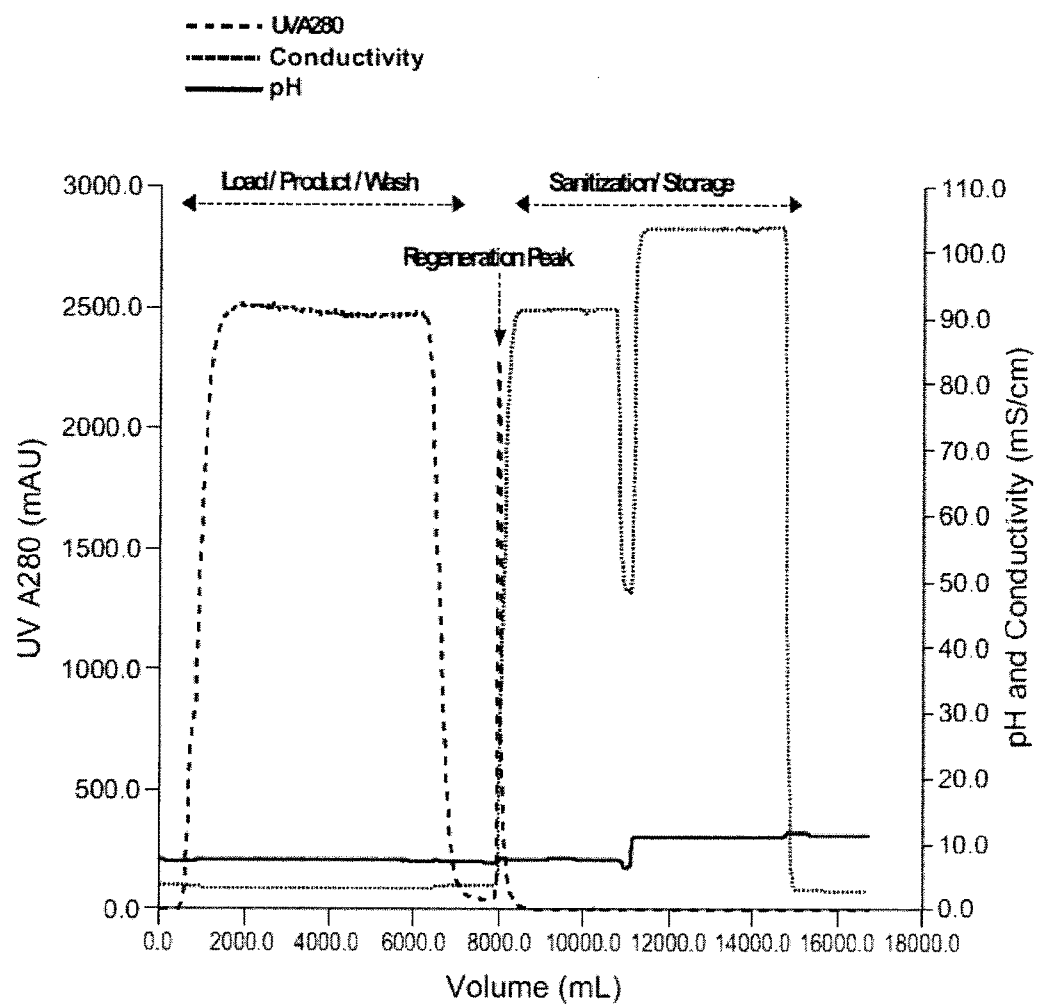

Collection of the product is guided by monitoring the absorbance of the effluent at a wavelength of 280 nm (see FIG. 7).

The sanitization flow rate is 100 cm/hr and the hold time is 60 mM.

A summary of the Q-sepharose chromatography conditions is set forth in Table 10:

TABLE 10

| DAC HYP Q-Sepharose chromatography parameters | |
|---|---|
| PARAMETER | SET POINT |
| Resin | Q Sepharose FF |
| Column bed height (cm) | 10-30, typically 19 |
| Column diameter (cm) | 1-120, depending on scale |
| Operation temperature | 5° C.-25° C. |
| Flow direction for equilibration/load/wash/regeneration/sanitization | Down |
| Equilibration/wash buffer | 20 mM Tris, 20 mM NaCl, pH 7.8 |
| Equilibration volume (CV) | 8 |
| Flow rate (cm/hr) | 100 |
| Load capacity (g/L) | <60 |
| Wash flow rate (cm/hr) | 100 |
| Collection criteria | 0.25 AU-0.25 AU (UV detector path-length: 5.0 mm) |
| Regeneration/sanitization buffer | 0.5M NaOH, 1M NaCl |
| Regeneration/sanitization volume (CV) | 1.8 |
| Regeneration/sanitization hold buffer | 0.5M NaOH, 1M NaCl |
| Regeneration/sanitization time (min) | 60 |
| Storage buffer | 12 mM NaOH |
| Storage buffer volume (CV) | 4 |
| Column storage temp. (° C.) | 5° C. |

For some uses, the storage buffer volume set point is 3 and the column storage temperature is set at 5°-25° C.

7.4.5. CM-650(M) Cation Exchange Chromatography

This chromatography step is the last step used in the process to reduce trace levels of process- and product-related impurities. In addition to reducing aggregates and cleavage fragments of the antibody, this step also reduces process-related impurities such as host cell nucleic acids and proteins, and leached Protein A.

Figure 8:
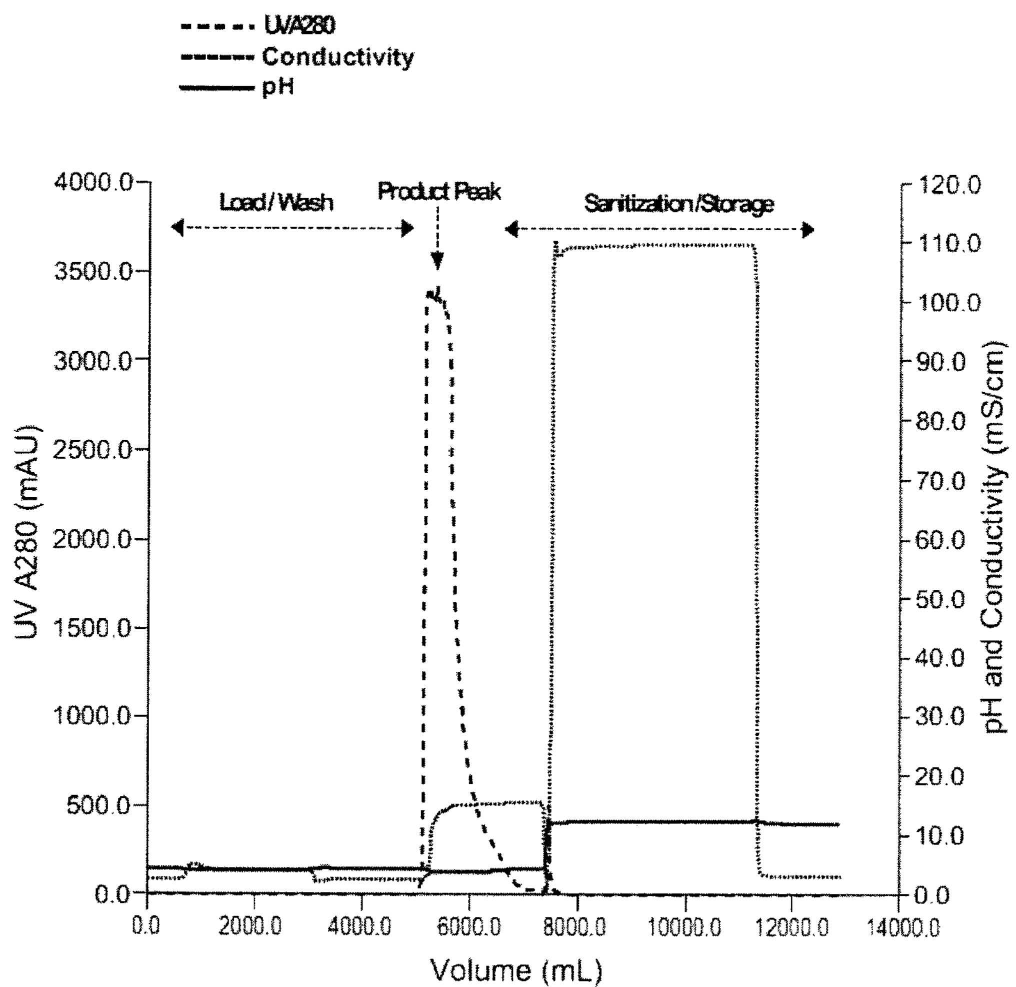

The column is equilibrated with an equilibration buffer of 20 mM sodium citrate, pH 4.5. The anion exchange eluate pool is adjusted to a pH of 4.5±0.1 or ±0.2 (e.g., 4.35-4.64) using 0.5 M citric acid and loaded onto the column to a target loading capacity of no greater than 25 or 30 grams of antibody (protein) per liter of packed resin. Following the binding step, the column is washed with the equilibration buffer to remove any unbound, or loosely-bound, impurities from the resin. The bound antibody is then eluted from the column in a step elution mode with an elution buffer of 20 mM sodium citrate, 75 mM sodium sulfate, pH 4.5. Peak collection is guided by monitoring the absorbance of the effluent at a wavelength of 280 nm (see FIG. 8).

A summary of the CM-650(M) chromatography conditions is set forth in Table 11:

TABLE 11

DAC HYP CM-650(M) chromatography parameters

| PARAMETER | SET POINT |
|---|---|
| Resin | CM650 (M) |
| Column bed height (cm) | 10-30, typically 18 |
| Column diameter (cm) | 1-140, depending on scale |
| Operation temperature | 20° C. |
| Equilibration/wash buffer | 20 mM NaCitrate, pH 4.5 |
| Equilibration volume (CV) | 5 |
| Flow rate (cm/hr) | 100 |
| Load preparation | Adjust pH of load to 4.5 with 0.5M citric acid |
| Load capacity (g/L) | ≤30 |
| Wash volume (CV) | 3 CV with equilibration buffer |
| Elution buffer | 20 mM NaCitrate, 75 mM $Na_2SO_4$, pH 4.5 |
| Cation exchange product pool collection criteria | 1.25 AU up-1.25 AU (Based on UV detector path-length of 5.0 mm) |
| IgG concentration diluted to | 8.5 |
| Dilution Buffer* | 20 mM NaCitrate, pH 4.5 |
| Regeneration/sanitization buffer | 0.5M NaOH |
| Regeneration/sanitization volume (CV) | 1.8 |
| Regeneration/sanitization hold time (min) | 60 |
| Storage buffer | 12 mM NaOH |
| Storage buffer volume (CV) | 4 |

*Optionally, dilution buffer is not used.

7.4.6. Nanofiltration

The purpose of the nanofiltration step is to provide additional viral clearance capacity to the purification process. The removal of viruses and virus-like particles at this step occurs through a size-exclusion mechanism. The pores of the filter are designed such that the antibody passes through the filter whereas the virus-like particles and viruses are retained on the upstream side of the filter.

The cation exchange eluate that has been filtered through a 0.22 μm or 0.1 μm filter is passed through a small virus-retaining nanofilter, followed by a filter flush with DAC HYP formulation buffer without polysorbate 80 (40 mM succinate, 100 mM sodium chloride, pH 6.0). The buffer flush step is applied to recover antibody that remains in the line and filter housing.

A summary of the nanofiltration parameters is set forth in Table 12:

TABLE 12

Nanofiltration parameters

| PARAMETER | SET POINT |
|---|---|
| Pre-filter | Ultipor Nylon filters |
| Virus Filter | V-Pro Magnus 2.2 or NFP |
| Pressure, psig | 20-30, typically 25 |
| WFI Flush | 100 L/ $m^2$* |
| Equilibration buffer and wash buffer post load | 40 mM sodium succinate, 100 mM NaCl, pH 6.0 |
| Equilibration (L) | 33 L/$m^2$** |
| Wash buffer volume (L) | 33 L/$m^2$† |
| Process capacity | Up to 371 L/$m^2$ |

*or >50 L/$m^2$
**or >50 L/$m^2$
†for approximately 50 L/$m^2$ 7.4.7. Ultrafiltration/Diafiltration (UF/DF)

This process step is designed to concentrate the product and exchange the buffer in the product to the DAC HYP formulation buffer without polysorbate 80. It is operated in a tangential flow mode using a 30 kDa nominal molecular weight cutoff membrane. Two ultrafiltration/diafiltration stages are used to produce 150 mg/mL formulation due to the expected product volume at the final concentration and relative hold-up volume of each UF system.

Figure 9:
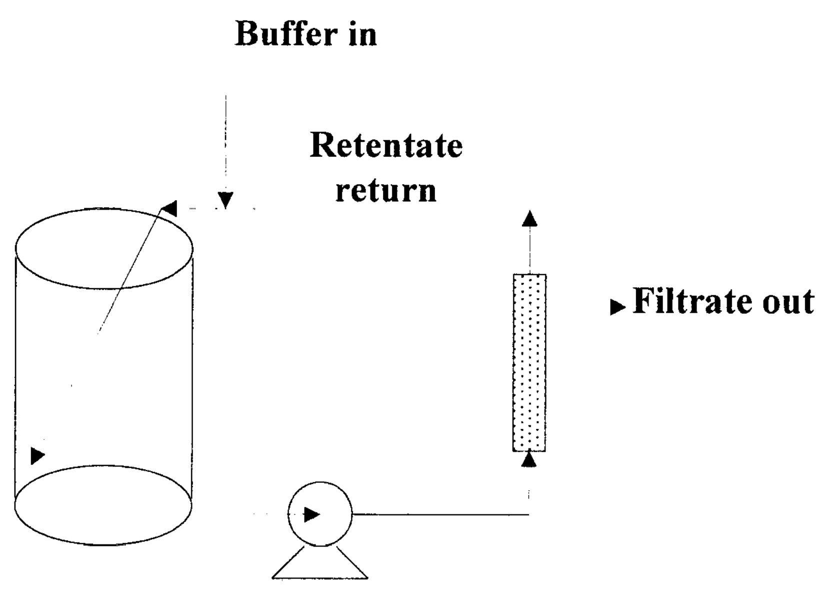

The first stage is processed using a large UF system (see FIG. 9). The nanofiltration filtrate is first concentrated to approximately 30 mg/mL and then diafiltered into exchange buffer (formulation buffer without polysorbate 80). The diafiltered antibody solution is further concentrated to approximately 100 mg/mL, then recovered at a concentration of approximately 55 mg/mL from the UF/DF system and transferred through a 0.22 μm filter. The diafiltered antibody solution can also be recovered at a concentration of approximately 20-60 mg/mL. A summary of the parameters of the first stage is set forth in Table 13:

TABLE 13

UF/DF stage 1 parameters
UF/DF Membrane: Millipore (Pellicon 2 or Pellicon 3, 30KD MWCO)

| PARAMETER | SET POINT |
|---|---|
| Membrane Loading capacity (g/m2) | ≤300 |
| Inlet pressure (psig) | 25 |
| Outlet pressure (psig) | 15 |
| Permeate pressure (psig) | Unrestricted/restricted |
| Equilibration/Diafiltration buffer | 40 mM sodium succinate, 100 mM NaCl pH 6.0 |
| Concentration during diafiltration (g/L) | 30 |

TABLE 13-continued

| UF/DF stage 1 parameters UF/DF Membrane: Millipore (Pellicon 2 or Pellicon 3, 30KD MWCO) | |
|---|---|
| PARAMETER | SET POINT |
| Diafiltration volume (exchange volumes) | 10 |
| Final concentration before product recovery (g/L) | ~100 |
| Membrane Reuse | Yes |
| Filter Flush | 40 mM succinate, 100 mM NaCl pH 6.0 |
| Sanitization Buffer (pre-use) | 0.5M NaOH* |
| Sanitization Time (mins) (pre-use) | 60** |
| Sanitization Temperature (° C.) (pre-use) | Room Temperature |
| Sanitization Flush | WFI |
| Sanitization Solution (post-use) | 0.1M NaOH |
| Sanitization Time (mins) (post-use) | 60 |
| Sanitization Temperature (° C.) (post-use) | Room Temperature |
| Storage Buffer | 0.1M NaOH |
| Product Concentration (g/L) | 70† |
| Product Storage (° C.) | 2-20, typically 20 |

*or 0.1M NaOH
**or 2 times 40 minutes
†for ranging from 20-70

The second stage is processed using a smaller UF system, but with the same 30 kDa cutoff membrane. The DAC HYP (typically 55 mg/mL) solution is concentrated to approximately 180 mg/mL, recovered from the UF system, and then transferred through a 0.22 μm filter. The UF system is rinsed with formulation buffer without polysorbate 80 and transferred through the 0.22 μm filter obtaining the purified drug substance at approximately 170 mg/mL or approximately 150-170 mg/mL. A summary of the parameters of the second stage is set forth in Table 14:

TABLE 14

| DAC HYP UF/DF stage 2 parameters UF/DF Membrane: Millipore (Pellicon 2 or Pellicon 3, 30KD MWCO) | |
|---|---|
| PARAMETER | SET POINT |
| Membrane Surface Area ($m^2$) | 0.005 to 20.5, depending on scale |
| Inlet pressure (psig) | 20 |
| Outlet pressure (psig) | Unrestricted |
| Permeate pressure (psig) | Unrestricted |
| Equilibration buffer | 40 mM sodium succinate, 100 mM NaCl pH 6.0 |
| Final concentration before product recovery (g/L) | 180 |
| Recirculation/Flush system volume (L) | 2 mL to 5 L, depending on scale |
| Recirculation/flush system buffer | 40 mM sodium succinate, 100 mM NaCl, pH 6.0 |
| Sanitization Flush | WFI |
| Sanitization Solution (post-use) | 0.1M NaOH |
| Sanitization Time (mins) (post-use) | 60* |
| Storage Buffer | 0.1M NaOH |
| 0.2 μm multimedia filter for post final concentration | 1 × 30 inch filters |

**or 2 times 40 minutes 7.5. DAC HYP Formulation

The final process step is the dilution of the purified drug substance to a final target concentration of 150 or 100 mg/L±10%, i.e., a final target concentration of 150±15 mg/mL (in the case of the 150 mg/mL formulation) or 100±10 mg/mL (in the case of the 100 mg/mL formulation) in buffer containing an appropriate concentration of polysorbate 80. The formulation is performed in stages.

For example, first, the formulation buffer without polysorbate 80 (40 mM sodium succinate, 100 mM sodium chloride, pH 6.0) is added to the purified drug substance to reach the 90% target volume of formulated drug substance. Then, a calculated amount of polysorbate 80 dilution buffer (40 mM succinate, 100 mM sodium chloride, 1% polysorbate 80, pH 6.0) is added to reach the target concentration of 0.03% (w/v) polysorbate 80 in the final formulation. Finally, the product volume is adjusted, using the formulation buffer (made of succinate and succinic acid for the 150 mg/mL formulation, and succinate and HCl for the 100 mg/mL formulation) without polysorbate 80, to achieve a final antibody concentration of 150±15 mg/mL (preferably 150±8 mg/mL). The 100 mg/mL drug product is formulated in a similar manner to a final concentration 100±10 mg/mL (preferably 100±5 mg/mL).

The formulated drug substance is filtered through a 0.22 μm filter into a BioProcess Container™ (BPC®) bag (or equivalent) which is placed inside a semi-rigid cylindrical support. The support encloses the BPC with a lid and provides a protective barrier between the flexible bag and the external environment. The formulated drug substance is stored at 2-8° C. in an access-controlled cooler for drug product fill/finish operations.

A summary of the formulation conditions is set forth in Table 15:

TABLE 15

| 150 mg/ml DAC HYP formulation conditions 0.2 μm filter for post formulation pool | |
|---|---|
| PARAMETER | SET POINT |
| Dilution buffer | 40 mM sodium succinate, 100 mM NaCl, pH 6.0 |
| Polysorbate 80 Stock Solution | 40 mM sodium succinate, 100 mM NaCl, pH 6.0, 1% (w/v) polysorbate 80 |
| Final Polysorbate 80 concentration (w/v) % | 0.03 |
| Final Daclizumab concentration (mg/mL) | 100 or 150 |
| Product Storage (° C.) | 2-8, commonly 5 |

1 mL of the drug product is filled into vials or a syringe. A summary of the components of the finished 150 mg/mL and 100 mg/mL products have the components shown in Table 16 (all quantities are nominal values):

TABLE 16

| Composition of the 150 mg/mL and 100 mg/mL DAC HYP Drug Product Formulations | | |
|---|---|---|
| Ingredient | Drug product: 150 mg/mL | Drug product: 100 mg/mL |
| DAC HYP | 150 mg | 100 mg |
| Sodium Succinate | 5.9 mg | 6.5 mg |
| Succinic Acid | 0.4 mg | Not applicable |
| Sodium Chloride | 5.8 mg | 5.8 mg |
| Polysorbate 80 | 0.3 mg | 0.3 mg |
| Hydrochloric Acid | Not applicable | As needed for adjustment to pH 6.0 |
| Sodium Hydroxide | As needed for adjustment to pH 6.0 | As needed for adjustment to pH 6.0 |
| Water for Injection | As needed for final volume | As needed for final volume |

7.6. Characterization of DAC HYP Drug Substance

DAC HYP is glycosylated at amino acid 296 of both heavy chain subunits, with the major oligosaccharide form existing as a core fucosylated biantennary structure lacking terminal galactose.

The N-terminus of DAC HYP heavy chain exists as three major forms: 1) N-terminal glutamine (predicted from the DNA sequence), 2) N-terminal pyroglutamate (from the cyclization of N-terminal glutamine), and 3) N-terminal valine, histidine and serine residues in addition to the predicted N-terminal glutamine residue (results from incomplete cleavage of the signal peptide).

The C-terminus of DAC HYP heavy chain exists with and without the C-terminal lysine residue. The major form lacks the C-terminal lysine residue, resulting in a C-terminal glycine.

DAC HYP has a calculated molecular weight of 144 kDa based on the primary amino acid composition defined by the nucleotide sequence. The corresponding molecular weight of the reduced heavy chain is 48.9 kDa and the reduced light chain is 23.2 kDa; these weights do not account for carbohydrate content or post-translational modifications.

DAC HYP binding is highly specific for CD25, which is expressed on activated but not on resting T and B lymphocytes. DAC HYP binding to CD25 on these activated cells blocks the binding of IL-2 to CD25 and subsequent formation of the high affinity IL-2 receptor complex. Consequently, IL-2-induced proliferation of the activated cells is blocked. The observed and potential therapeutic efficacy of DAC HYP is believed to rest in large part on its inhibitory effect on the proliferation of activated autoreactive T-cells. However, DAC HYP might also exert a therapeutic effect through its blocking effect on other CD25-bearing cell types such as eosinophils.

To confirm that high concentration 150 mg/ml DAC HYP formulations were suitable for clinical investigations, a comprehensive physicochemical and biological evaluation was performed to characterize and compare two batches of DAC HYP 150 mg/mL drug substance, referred to herein as Batch 1 and Batch 2 (or Batch 150-1 or Batch 150-2, respectively), to Reference Standard lot RS0801, which is from a lot of DAC HYP 100 mg/mL manufactured at the 10,000 L scale.

The results demonstrate that the DAC HYP drug product 150 mg/mL lots are of high purity, are comparable to the 100 mg/mL lots, and are suitable for use in clinical studies. A summary of these characteristics is shown in Table 17:

TABLE 17

| Purity characteristics of DAC HYP (all concentrations are nominal) | | | | |
|---|---|---|---|---|
| Category | Test | 150 mg/mL lots (2 batches) | 100 mg/mL lots (24 batches) | Useful Criteria (for 150 mg/ml) |
| Quality | Color, appearance and clarity | Colorless, clear to slightly opalescent liquid, essentially free of visible particles | Colorless, clear to slightly opalescent liquid; no visible particles | Colorless, clear to slightly opalescent liquid, essentially free of visible particles |

TABLE 17-continued

| Purity characteristics of DAC HYP (all concentrations are nominal) | | | | |
|---|---|---|---|---|
| Category | Test | 150 mg/mL lots (2 batches) | 100 mg/mL lots (24 batches) | Useful Criteria (for 150 mg/ml) |
| | pH determination | 6.0 at 25° C. | 6.0-6.1 at 25° C. | 5.8-6.2 at 25° C. |
| | Product concentration by UV spectroscopy | 143-148 mg/mL | 96.0-103 mg/mL | 135-165 mg/mL |
| | Cation Exchange Chromatography | Chromatogram consistent with reference | Not available | Chromatogram consistent with reference |
| Identity | Anti-idiotype ELISA | Identifies as daclizumab | Identifies as daclizumab | Identifies as daclizumab |
| | Cation exchange chromatography | Not applicable | Chromatogram consistent with reference | Not applicable |
| Purity | Size exclusion chromatography | 99.3% to 99.4% main peak 0.6% to 0.7% aggregate | 99.2% to 99.6% main peak 0.4% to 0.8% aggregate | ≥95% main peak ≤3% aggregate |
| | SDS-PAGE (colloidal blue stain) reduced | 97.3% purity | 95.8%-97.0% purity | ≥93% purity |
| | SDS-PAGE (silver stain) reduced and non-reduced | Sample staining consistent with reference | Sample staining consistent with reference | Sample staining consistent with reference |
| | DNA content | <0.1 pg/mg | <0.01-<0.06 pg/mg | ≤0.25 pg/mg |
| | Residual protein A | <1 ppm-1 ppm | <1 ppm | ≤30 ppm (based on weight of protein A relative to weight of antibody) |
| | Host cell protein | <1 ppm (weight basis) | <1 ppm-5 ppm (weight basis) | ≤50 ppm (based on weight of host cell protein relative to weight of antibody) |
| Potency | Binding potency | 86%-105% relative potency | 78%-129% relative potency | 70%-130% relative potency |
| | Functional potency | 95%-101% relative potency | 73%-121% relative potency | 70%-130% relative potency |
| Safety | Bacterial endotoxins | <0.01 EU/mg | <0.01 EU/mg | ≤0.751 EU/mg |
| | Bioburden | 0 CFU/100 mL | 0 CFU/10 mL 0 CFU/100 mL | ≤10 CFU/100 mL |
| Excipients | Polysorbate 80 | 0.026%-0.029% w/v | 0.027%-0.034% w/v | 0.024%-0.036% w/v |
| | Osmolality | 281-290 mOsm/Kg | 288-299 mOsm/Kg | 267-327 mOsm/Kg |

7.6.1. Color, Appearance, and Clarity

The appearance of DAC HYP drug substance is assessed by visually examining the color and clarity of the solution in direct light against a black background and white background without magnification. The solution is also evaluated for the presence of visible particles. The typical appearance of various lots of DAC HYP drug product is described in Table 17.

7.6.2. pH Determination

The pH of DAC HYP is determined in accordance with the U.S. Pharmacopeia Protocol No. (791). The pH ranges of various lots of DAC HYP drug product are summarized in Table 17.

7.6.3. Product Concentration by UV Spectroscopy

The concentration of DAC HYP is determined by UV spectroscopy. DAC HYP samples are diluted gravimetrically with buffer. The UV absorbance of each diluted sample solution is measured at 278 nm against a buffer blank. The protein concentration of the sample is calculated using the absorptivity coefficient for DAC HYP. The protein concentrations of various lots of DAC HYP drug product are summarized in Table 17.

7.6.4. N-Terminal Sequencing

DAC HYP 150 mg/mL lots were evaluated by N-terminal sequencing. The samples were analyzed using an automated Edman degradation sequencing instrument.

The expected amino acid sequence of the light chain through the first 15 residues, DIQMTQSPSTLSASV (SEQ ID NO:13), was confirmed for all samples.

The majority of heavy chain in DAC HYP is blocked by a pyroglutamate (pE) residue that will not produce an N-terminal heavy chain sequence. The next most prevalent N-terminal heavy chain sequence in DAC HYP begins with a valine, histidine, serine (VHS) sequence, resulting from the lack of processing the three terminal residues of the heavy chain signal peptide. Fourteen of the first fifteen N-terminal residues were confirmed for the VHS heavy chain sequence (VHSQVQLVQSGAEVK (SEQ ID NO:14)) in all samples. The fourth residue, glutamine, could not be confirmed due to the large amount of glutamine detected from LC in the preceding sequencing cycle. Evidence of heavy chain with N-terminal glutamine was also present in all samples. This sequence is a result of the native N-terminal heavy chain glutamine residue not undergoing cyclization to the pyroglutamate form. The N-terminal sequencing results for the 150 mg/mL lots are consistent with the sequences predicted from the heavy and light chain coding sequences. Comparable results were obtained for the 100 mg/mL lots.

7.6.5. Heavy and Light Chain Mass Analysis

The molecular masses of the heavy chain and light chain of the DAC HYP 150 mg/mL lots and Reference Standard RS0801 were evaluated by liquid chromatography mass spectrometry (LC-MS) analysis. All lots were deglycosylated with the amidase PNGaseF, reduced with dithiothreitol, alkylated with iodoacetic acid, and separated by reversed phase chromatography. Theoretical heavy and light chain masses were calculated from the protein sequence. The observed masses of the samples were within 1 Da of the calculate masses, as shown in Table 18 below:

TABLE 18

Heavy and Light Chain Mass Results

| | LC (Da) | HC (pE,-K)(Da) | HC (VHS,-K) (Da) |
|---|---|---|---|
| Theoretical Mass | 23,505 | 49,356 | 49,697 |
| RS0801 | 23,505 | 49,357 | 49,696 |
| Batch 150-1 | 23,505 | 49,357 | 49,696 |
| Batch 150-2 | 23,504 | 49,357 | 49,696 |

As described in the preceding subsection, the two most prevalent forms of DAC HYP heavy chain are known to contain an N-terminal pyroglutamate (pE) residue or a valine, histidine, serine (VHS) sequence and lack C-terminal lysine. The molecular weights obtained for the two predominant heavy chain variants and the light chain in the 150 mg/mL lots were comparable to those of Reference Standard RS0801 and consistent with the masses predicted from the protein sequences.

Together with the peptide mapping results presented in the following subsection, the heavy and light chain mass results confirm the presence of the expected light chain and heavy chain primary structures in the DAC HYP 150 mg/mL lots.

7.6.6. Peptide Mapping

DAC HYP 150 mg/mL lots and Reference Standard RS0801 (DAC HYP produced from a 100 mg/mL drug substance lot manufactured at the 10,000 L scale) were evaluated using reversed phase HPLC peptide mapping. All lots were reduced with dithiothreitol, alkylated with iodoacetic acid, and enzymatically digested with trypsin. The resulting peptides were separated by reversed phase chromatography and detected by ultraviolet absorbance at 215 nm to generate peptide maps.

To verify the primary amino acid sequence, the peptide maps of the 150 mg/mL lots were compared to that of Reference Standard RS0801. Peptides corresponding to ninety eight percent of the expected heavy and light chain residues have previously been identified by mass spectrometry in the peptide map of Reference Standard RS0801. The residues that have not been accounted for in the peptide map are single amino acids or reside in very polar dipeptides, and are not expected to be retained by the reversed phase column. Masses consistent with pyroglutamate, glutamine, and the VHS sequence at the N-terminus of the heavy chain N-terminal peptide have been identified in the reference standard. DAC HYP contains a consensus site for N-linked glycosylation in the Fc portion of the heavy chain at Asn296 and masses consistent with linked complex core biantennary oligosaccharide structures have been identified for the peptide containing the Asn296 residue.

Figure 10:
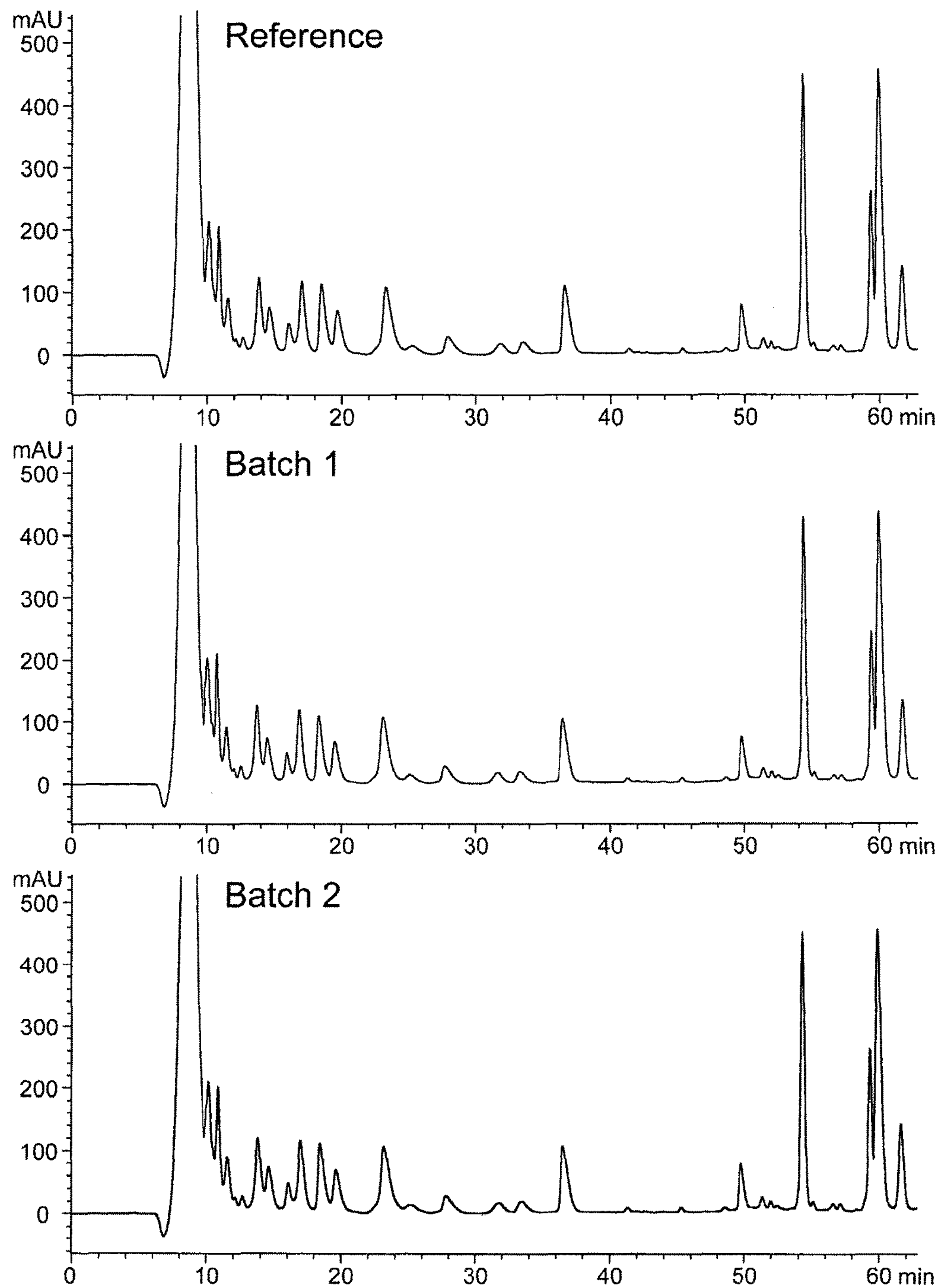
Figure 11:
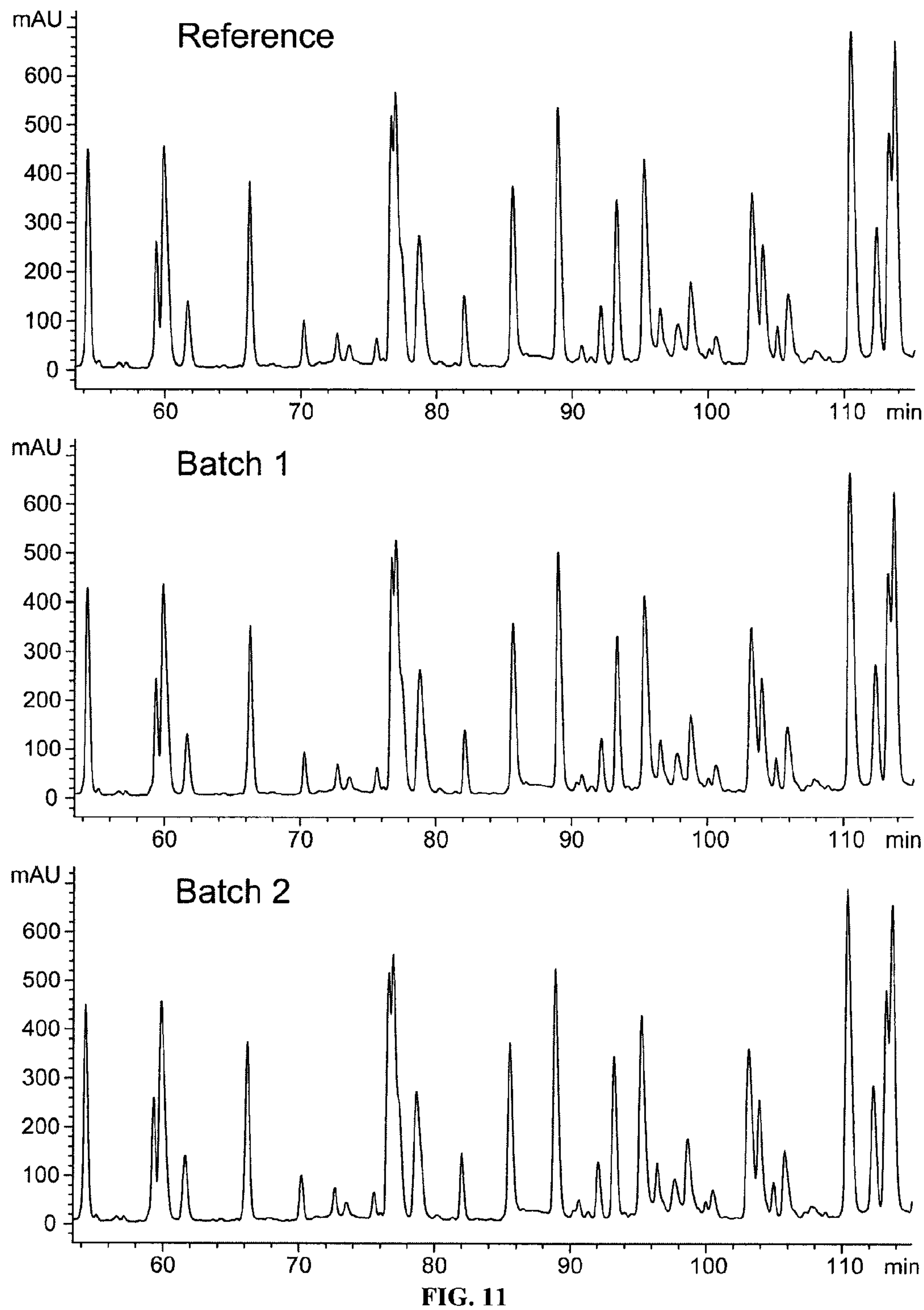
Figure 12:
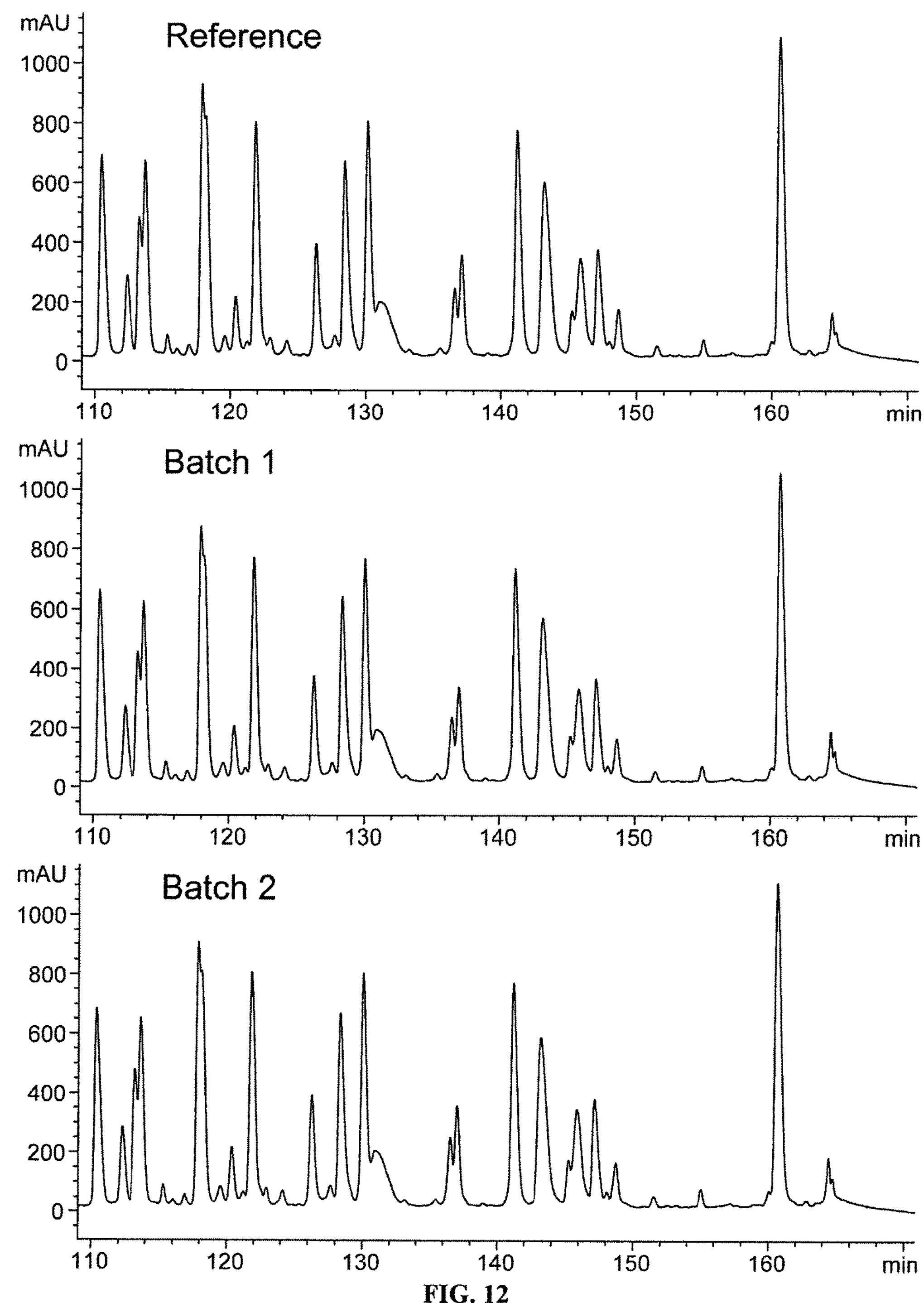

Peptide maps comparing the DAC HYP 150 mg/mL lots to Reference Standard RS0801 are shown in FIG. 10 (0 to 60 minutes), FIG. 11 (55 to 115 minutes), and FIG. 12 (110 to 170 minutes). The peptide maps of the DAC HYP 150 mg/mL lots are comparable to those of the reference standard and confirm the presence of the expected primary structure in the 150 mg/mL lots.

7.6.7. Circular Dichroism Spectroscopy

DAC HYP 150 mg/mL lots and Reference Standard RS0801 were analyzed by far ultraviolet circular dichroism spectroscopy (far-UV CD) to evaluate secondary structure. Prior to analysis samples were diluted with water to a final protein concentration of 0.2 mg/mL. Spectra were acquired from 195 to 260 nm using a 0.1 cm cell and the signal obtained was converted to molar ellipticity after buffer subtraction.

Figure 13:
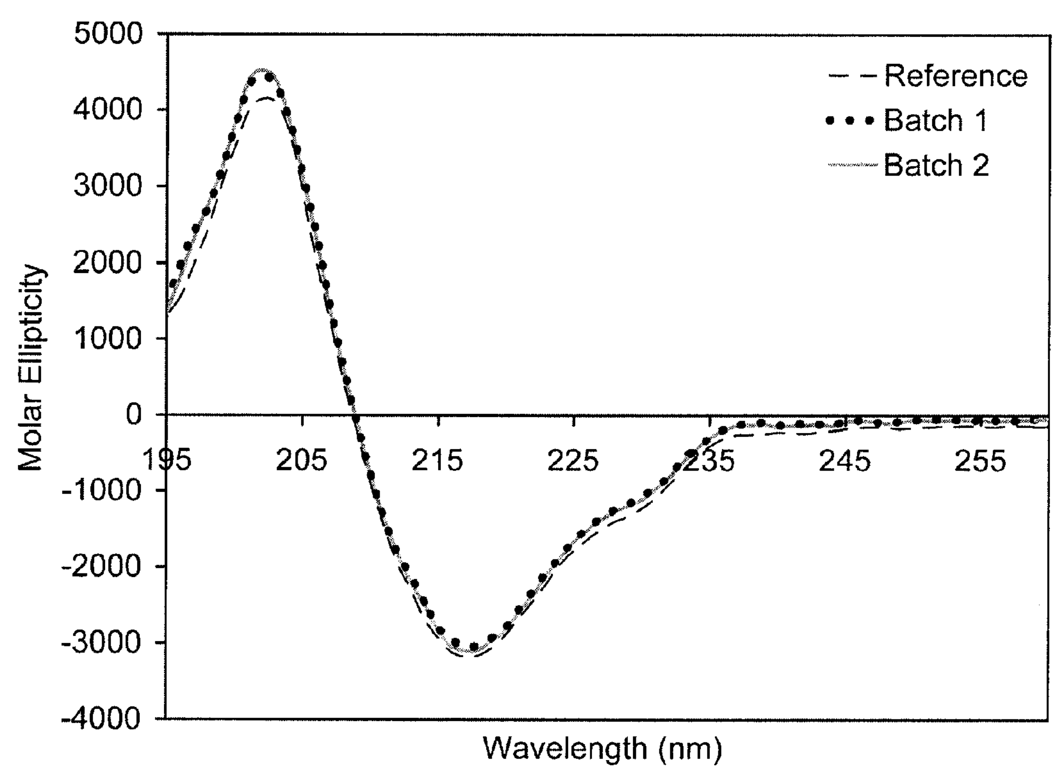

The overlaid far-UV CD spectra of DAC HYP 150 mg/mL lots Batch 1 and Batch 2 and Reference Standard RS0801 are shown in FIG. 13. The spectra of all lots show a positive band at approximately 202 nm and a negative band at approximately 217 nm. The negative band at 217 nm is characteristic of a β sheet conformation, the predominant conformation of IgG molecules. The far-UV CD spectra of the lots were similar, which is supportive of a uniform secondary structure among the DAC HYP 150 mg/mL lots and Reference Standard RS0801.

7.6.8. Ultraviolet Spectroscopy

DAC HYP 150 mg/mL lots and Reference Standard RS0801 were analyzed by ultraviolet (UV) spectroscopy to evaluate tertiary structure. Prior to analysis samples were diluted with formulation buffer (40 mM succinate, 100 mM sodium chloride, 0.03% polysorbate 80, pH 6.0) to a final protein concentration of 0.5 mg/mL. Spectra were acquired from 250 to 350 run using a 1 cm path length quartz cuvette and normalized to an absorbance of 1.0 at 280 nm.

Figure 14A:
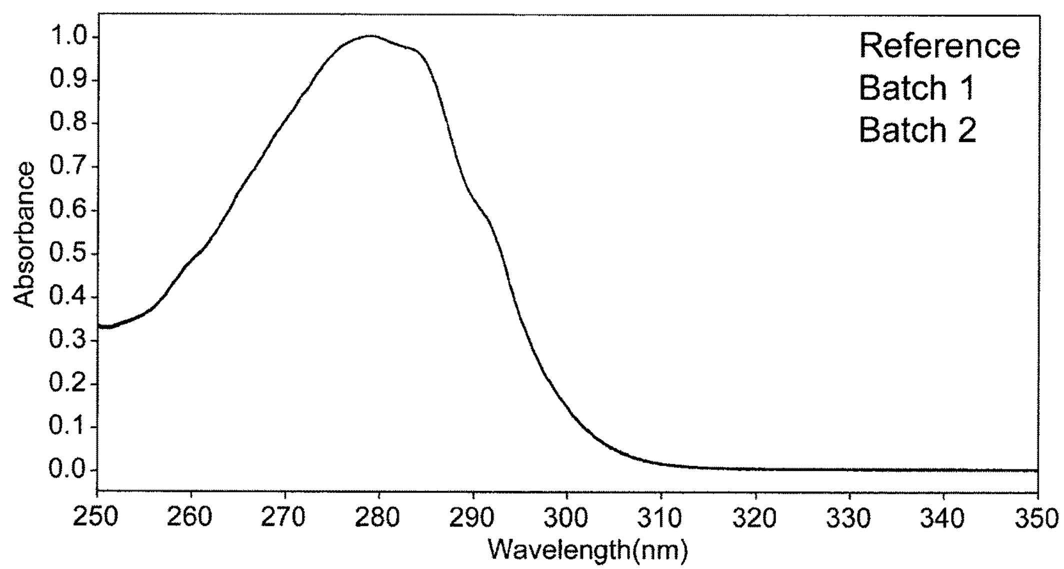
Figure 14B:
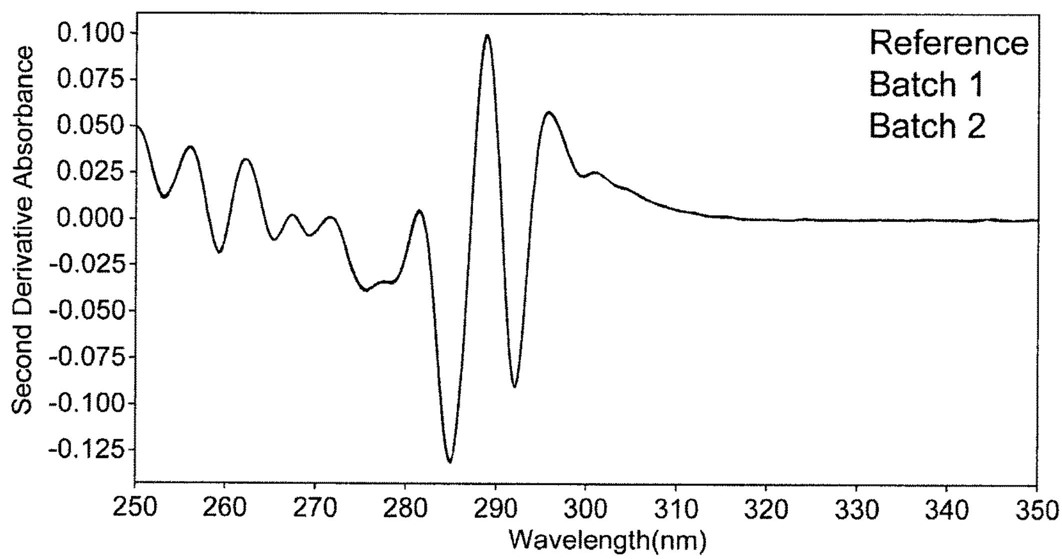

The overlaid zero-order and second derivative UV spectra (calculated from the smoothed zero-order data) are shown in FIGS. 14A and 14B, respectively. The zero-order and second derivative spectra of all lots evaluated were superimposable, which is supportive of a uniform tertiary structure among the DAC HYP 150 mg/mL lots Batch 1 and Batch 2 and Reference Standard RS0801.

7.6.9. Size Exclusion Chromatography

Size exclusion chromatography (SEC) was performed using a porous silica column with an aqueous mobile phase and ultraviolet absorbance detection at 280 nm. In particular, 15 μL test sample (20 mg/mL antibody in elution buffer) was analyzed at room temperature on a 7.8 mm×30 cm TSK G3000SW$_{xL}$ column (Tosoh Biosciences, part no. 601342) equipped with a 0.5 μm pre-column filter (Upchurch, part no. A-102X) using an isocratic gradient of elution buffer (200 mM $KPO_4$, 150 mM KCl, pH 6.9) at a flow rate of 1 mL/min.

Figure 15A:
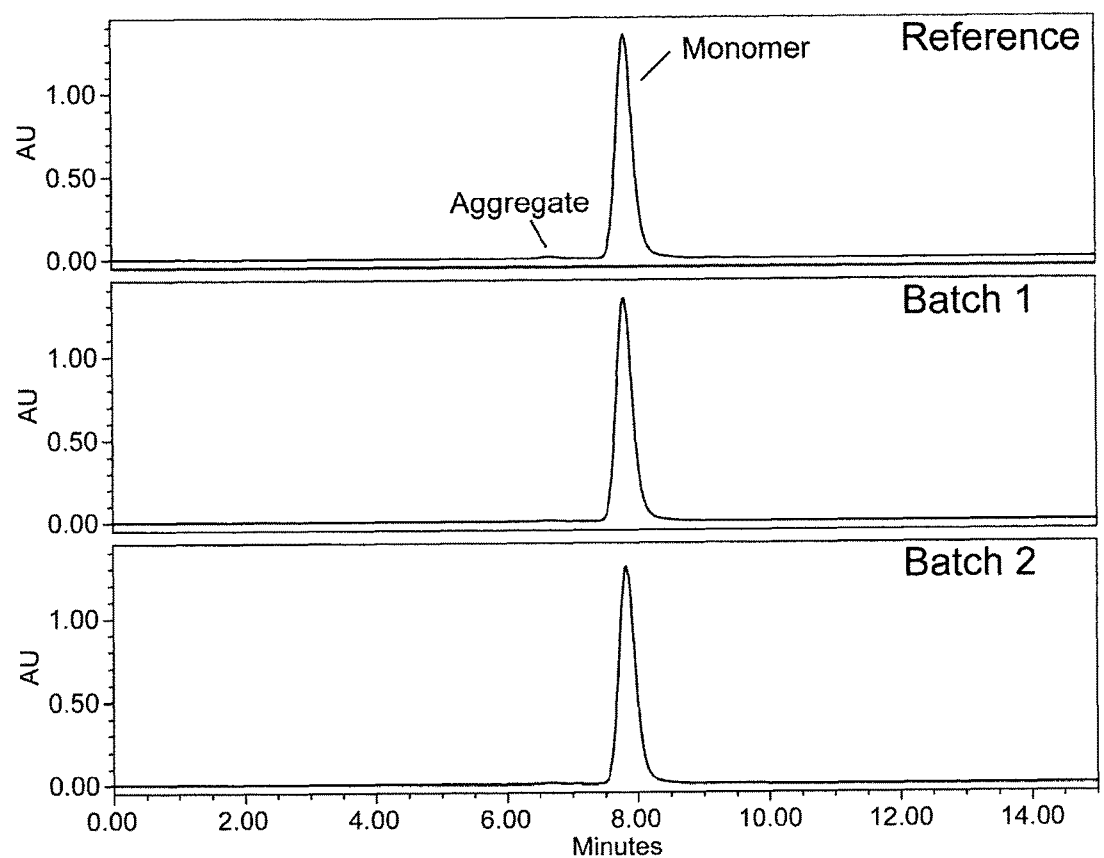
Figure 15B:
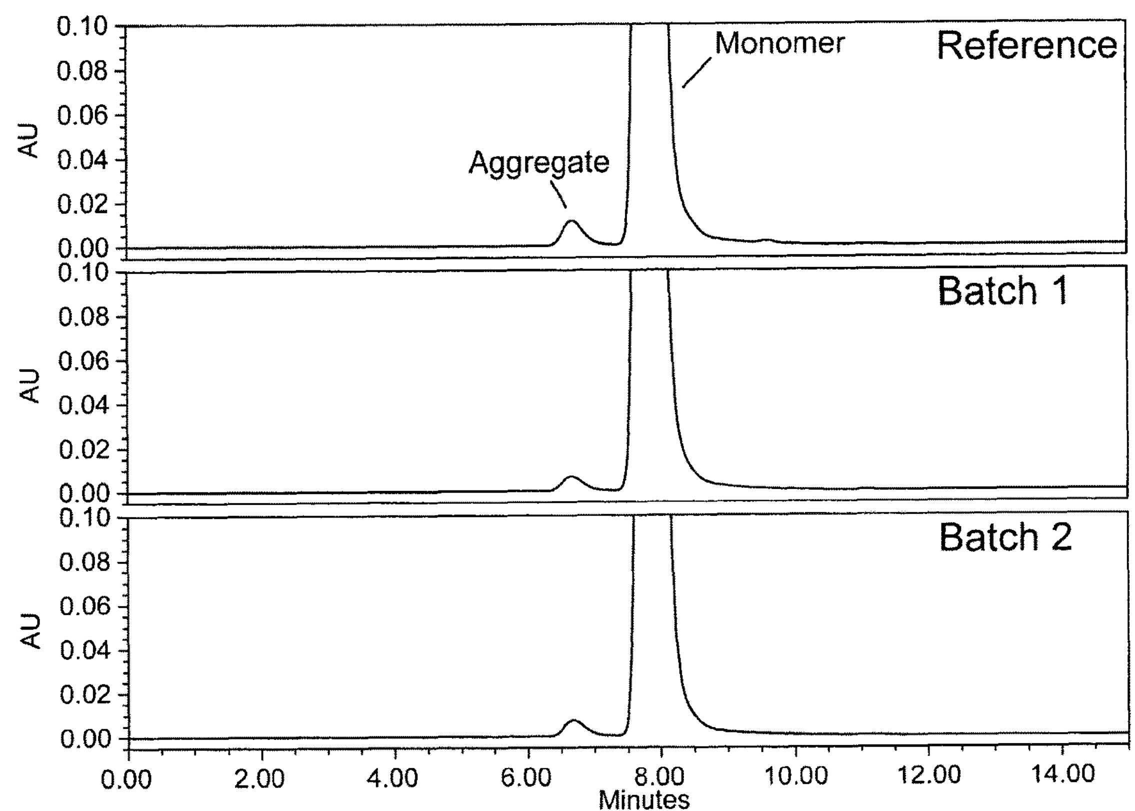

As shown in FIG. 15A (full scale) and FIG. 15B (expanded scale), the chromatographic profiles of the DAC HYP 150 mg/mL lots were comparable to that of Reference Standard RS0801. All lots exhibited the same major peak corresponding to daclizumab monomer and a minor aggregate peak. Aggregate results for DAC HYP 150 mg/mL lots were comparable to those of DAC HYP 100 mg/mL lots as shown in Table 19 below:

TABLE 19

| Percentage Aggregate Results | | |
|---|---|---|
| 100 mg/mL (n = 24 lots) | Average | 0.6 |
| | Standard Deviation | 0.1 |
| | Minimum | 0.4 |
| | Maximum | 0.8 |
| 150 mg/mL | Batch 150-1 | 0.6 |
| | Batch 150-2 | 0.7 |

The 150 mg/mL lots and Reference Standard RS0801 were analyzed using SEC with multi-angle light scattering detection (SEC-MALS) to determine the molecular weight of the aggregate peak. For all lots, the molecular weight obtained for the aggregate peak was approximately 300 kDa, which is consistent with antibody dimer.

Figure 16:
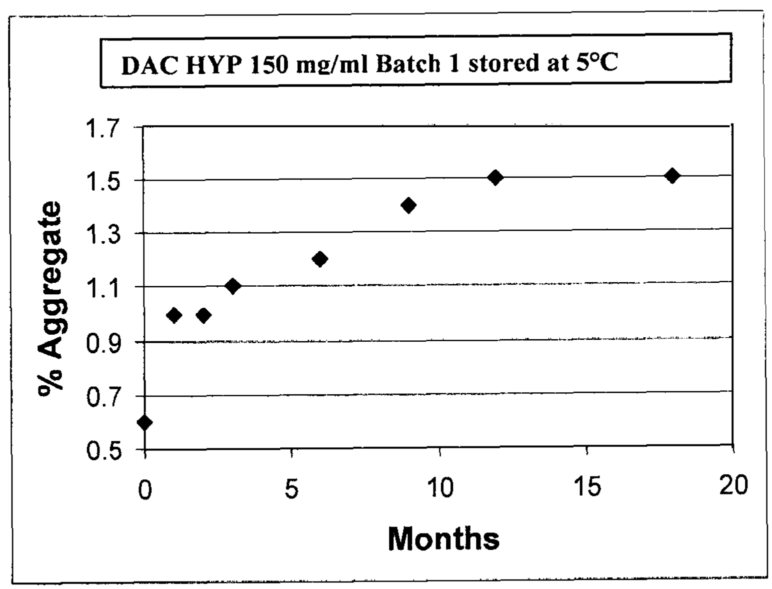
FIG. 16 is a plot of DAC HYP aggregation as a function of time.

Aggregate formation in DAC HYP was monitored over an 18-month period. The level of aggregates in the formulation rose, but the percentage of aggregates plateaued and did not exceed approximately 1.5% when stored at 5° C. for 18 months (see FIG. 16). New data with new batches indicates that approximately 1.8-1.9% aggregates may appear at 6 weeks when stored at 5° C., but for all samples tested, less than 3% aggregates formed over a period of 5 years when stored at 5° C.

7.6.10. Sedimentation Velocity Analytical Ultracentrifugation

The monomer and aggregates in DAC HYP 150 mg/mL and 100 mg/mL lots were characterized using sedimentation velocity analytical ultracentrifugation (SV-AUC). The sedimentation coefficient value and relative abundance for the monomer and each of the aggregates are presented in Tables 20 and 21 below.

TABLE 20

Sedimentation Coefficient Values for Monomer and Aggregates (in Svedbergs)

| | | Monomer | Dimer | Trimer | Tetramer |
|---|---|---|---|---|---|
| 100 mg/mL | Average | 6.14 | 8.48 | 10.6 | 12.1 |
| (n = 8 lots) | Range | 6.11-6.18 | 8.36-8.67 | 10.3-10.8 | 11.8-12.7 |
| 150 mg/mL | Batch 150-1 | 6.16 | 8.52 | 10.4 | 11.6 |
| | Batch 150-2 | 6.13 | 8.33 | 10.3 | 11.9 |

TABLE 21

Relative Abundance of Monomer, Dimer, Trimer, and Tetramer

| | | % Monomer | % Dimer | % Trimer | % Tetramer |
|---|---|---|---|---|---|
| 100 mg/mL | Average | 97.5 | 1.8 | 0.4 | 0.2 |
| (n = 8 lots) | Range | 96.7-98.5 | 1.3-2.2 | 0.2-0.7 | 0.1-0.4 |
| 150 mg/mL | Batch 150-1 | 97.6 | 1.9 | 0.4 | 0.1 |
| | Batch 150-2 | 96.9 | 2.3 | 0.5 | 0.3 |

Monomer was the major component observed in each of the lots. The sedimentation coefficient of the monomer peak was highly consistent among the lots indicating that the conformation of the monomer is comparable between the 150 mg/mL and 100 mg/mL lots. The monomer content of the 150 mg/mL lots was comparable to that of the 100 mg/mL lots.

The predominant aggregate species in each of the lots had a sedimentation coefficient consistent with antibody dimer. This is consistent with SEC-MALS results, which indicate that the SEC aggregate peak is composed primarily of antibody dimer (see preceding subsection). Low levels of two larger aggregate species that had sedimentation coefficients consistent with trimer and tetramer were also observed in each of the lots by AUC. The dimer, trimer, and tetramer content of the 150 mg/mL lots was comparable to that of the 100 mg/mL lots.

7.6.11. Quantitative Reduced SDS-PAGE

Purity was determined by SDS-PAGE using 4-20% (typically 14%) tris-glycine gels with Colloidal blue stain. Samples were analyzed under reducing conditions with a sample load of 10 μg. Purity was calculated by dividing the sum of the heavy chain and light chain band area by the total band area as measured by densitometry.

As shown in Table 22 below, the 150 mg/mL lots are of high purity and comparable to the 100 mg/mL lots:

TABLE 22

Quantitative Reduced SDS-PAGE Results

| | | % Purity |
|---|---|---|
| 100 mg/mL (n = 7 lots) | Average | 96.4 |
| | Standard Deviation | 0.5 |
| | Minimum | 95.8 |
| | Maximum | 97.0 |
| 150 mg/mL | Batch 150-1 | 97.3 |
| | Batch 150-2 | 97.3 |

7.6.12. Qualitative SDS-PAGE

Figure 17:
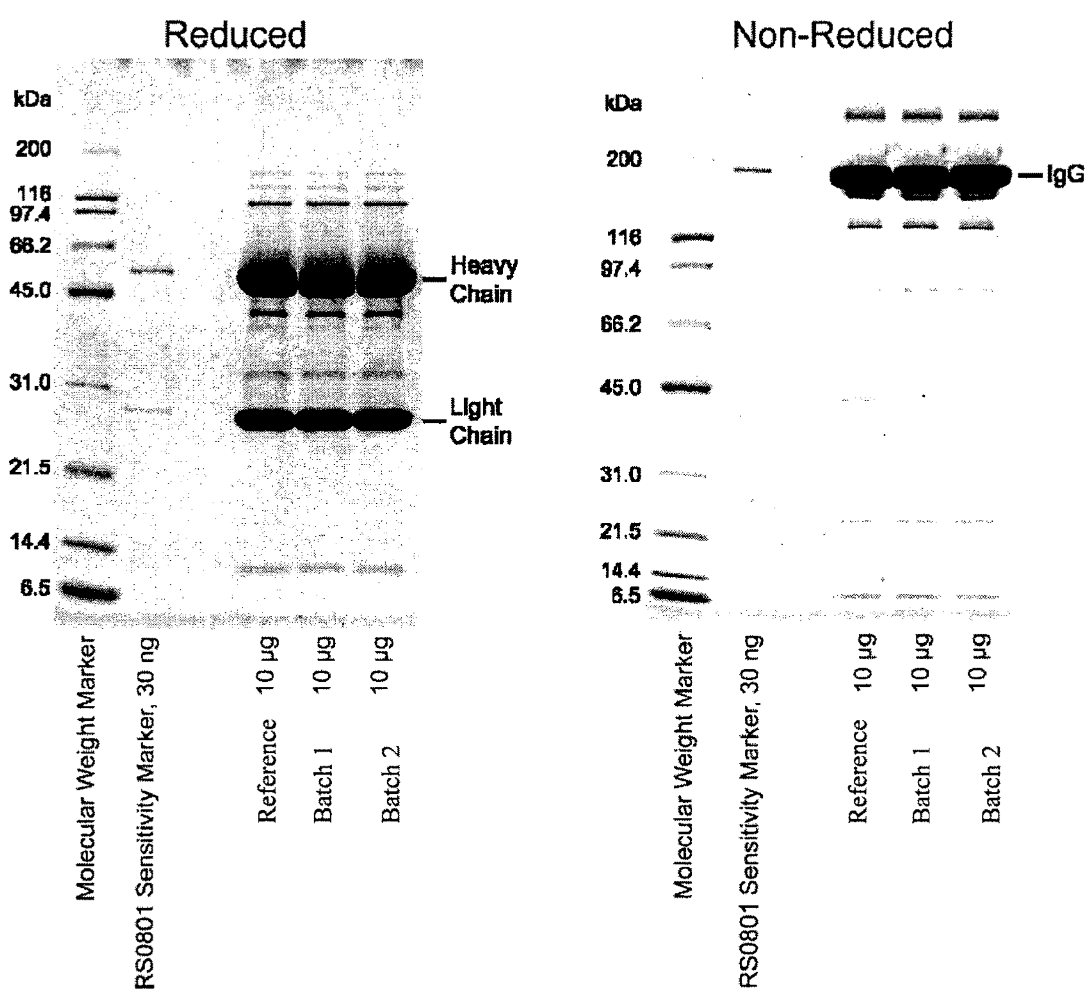
FIG. 17 shows reduced and non-reduced SDS-PAGE (left and right panels, respectively). The reference profile is a 100 mg/ml DAC HYP preparation and Batch 1 and Batch 2 correspond to 150 mg/ml DAC HYP preparations.

Purity of DAC HYP was assessed by both reduced and non-reduced gel electrophoresis. Precast 14% or 8-16% Tris-glycine gels were used for the analysis. Aliquots from the two batches of 150 mg/mL DAC HYP formulation were compared to a reference batch, as previously described. Reduced and non-reduced gels analyzing the purity of DAC HYP are shown in FIG. 17. The band pattern of the 150 mg/mL lots was comparable to that of Reference Standard RS0801, with no new bands detected in the 150 mg/mL lots.

7.6.13. Cation Exchange Chromatography

The charge isoform distribution of the DAC HYP 150 mg/mL lots and 100 mg/mL lots were evaluated using cation exchange chromatography (CEX). CEX was performed using a nonporous, carboxylate functionalized, weak cation exchange column with detection at 220 nm. 100 μL of test sample (1 mg/mL antibody dissolved in Buffer A) was resolved at room temperature on a ProPac WCX-10 column (Dionex Corporation) equipped with a ProPac WCX-10G guard column (Dionex Corporation) using the following separation gradient (column is equilibrated with Buffer A):

| Time (min.) | % Buffer A | % Buffer B | Flow Rate (mL/min) |
|---|---|---|---|
| 0.0 | 100 | 0 | 1 |
| 60.0 | 40 | 60 | 1 |
| 80.0 | 0 | 100 | 1 |
| 85.0 | 0 | 100 | 1 |
| 85.1 | 100 | 0 | 1 |
| 100.0 | 100 | 0 | 1 |

Buffer A = 15 mM sodium phosphate, pH 5.9
Buffer B = 250 mM NaCl, 15 mM sodium phosphate, pH 5

As shown in FIG. 18, the CEX chromatograms of the 150 mg/mL lots are consistent with those of Reference Standard RS0801, with no new charge isoforms detected in the 150 mg/mL lots. The five major isoforms present in the CEX chromatograms are due to heterogeneity at the heavy chain N-terminus and include: 1) two pyroglutamate residues (pE/pE); 2) one pyroglutamate residue and one glutamine residue (pE/Q); 3) one pyroglutamate residue and one VHS sequence (truncated VHS signal peptide preceding the N-terminal glutamine residue of the mature heavy chain) (pENHS); 4) one glutamine residue and one VHS sequence (Q/VHS); 5) two VHS sequences (VHS/VHS). C-terminal lysine (K) isoforms are also resolved and identified in FIG. 18. Each of the N-terminal isoforms described above may exist as different C-terminal isoforms (0, 1, or 2 K). Because of the complexity of the mixture, the C-terminal lysine isoforms are only clearly resolved and measurable for the major pE/pE and pE/VHS isoforms using the described method.

Quantitative N- and C-terminal isoform results are provided for the 150 mg/mL and 100 mg/mL lots in Tables 23 and 24, respectively, where the reported percentage is based upon the percentage of the area under the curve (AUC) of the specific peak as compared to the total AUC of all peaks:

TABLE 23

| CEX Results - N-Terminal Isoforms | | | | | | |
|---|---|---|---|---|---|---|
| | | % pE/pE | % pE/Q | % pE/VHS | % Q/VHS | % VHS/VHS |
| 100 mg/mL | Average | 38 | 11 | 40 | 7 | 5 |
| (n = 24 lots) | Standard Deviation | 2.8 | 0.8 | 2.0 | 1.1 | 3.8 |
| | Minimum | 31 | 9 | 34 | 4 | 1 |
| | Maximum | 42 | 12 | 42 | 9 | 17 |
| 150 mg/mL | Batch 150-1 | 31 | 9 | 31 | 12 | 17 |
| | Batch 150-2 | 32 | 9 | 31 | 11 | 17 |

pE/pE = Two Pyroglutamate Residues;
pE/Q = One Pyroglutamate Residue, One Glutamine Residue;
pE/VHS = One Pyroglutamate Residue, One Truncated Signal Peptide;
Q/VHS = One Glutamine Residue, One Truncated Signal Peptide; and
VHS/VHS = Two Truncated Signal Peptides.

TABLE 24

| CEX Results —C-Terminal Isoforms | | | | |
|---|---|---|---|---|
| | | % 0K | % 1K | % 2K |
| 100 mg/mL | Average | 78 | 16 | 6 |
| (n = 24 lots) | Standard Deviation | 2.5 | 1.7 | 1.0 |
| | Minimum | 69 | 14 | 5 |
| | Maximum | 80 | 22 | 10 |
| 150 mg/mL | Batch A | 73 | 19 | 8 |
| | Batch B | 74 | 19 | 8 |

0K = No C-terminal lysine residue on either heavy chain
1K = C-terminal lysine residue on one heavy chain
2K = C-terminal lysine residue on both heavy chains 7.6.14. Oligosaccharide Mapping The oligosaccharide distributions of the DAC HYP 150 mg/mL and 100 mg/mL lots were evaluated by oligosaccharide mapping. N-linked oligosaccharides were released enzymatically from heavy chain Asn296 using the amidase PNGaseF. The oligosaccharides were subsequently derivatized with a fluorescent label (in this case anthranilic acid) and separated from the antibody via a nylon membrane. The derivatized, cleaved N-linked glycans were resolved at 50° C. on a 250×4.6 mm polymeric-amine bonded Asahipak Amino $NH_2P$-504E column (5 μm particle size, Phenomenex, cat. No. CHO-2628) with fluorescent detection, using the following elution gradient (using a sample injection volume of 100 μL; column is equilibrated with 85% Buffer A/15% Buffer B):

| Time (min.) | % Buffer A | % Buffer B | Flow Rate (mL/min) |
|---|---|---|---|
| 0 | 85 | 15 | 1 |
| 2 | 85 | 15 | 1 |
| 10 | 80 | 20 | 1 |
| 60 | 55 | 45 | 1 |
| 70 | 5 | 95 | 1 |
| 75 | 5 | 95 | 1 |
| 76 | 85 | 15 | 1 |
| 90 | 85 | 15 | 1 |

Buffer A = 1% v/v tetrahydrofuran, 2% v/v acetic acid in acetonitrile
Buffer B = 1% v/v tetrahydrofuran, 5% v/v acetic acid, 3% v/v triethylamine in water Chromatograms comparing the 150 mg/mL lots to Reference Standard RS0801 are shown in FIG. 19. Oligosaccharide peaks constituting at least 1.0% of the total peak area are labeled and reported below in Table 25:

TABLE 25

| Oligosaccharide Results | | | | | |
|---|---|---|---|---|---|
| | | % G0-GlcNAc | % G0 | % Peak 3 | % G1 |
| 100 mg/mL | Average | 8.6 | 86.3 | 1.5 | 2.0 |
| 600 L (n = 22 lots) | Minimum | 6.9 | 84.6 | 1.4 | 1.5 |
| | Maximum | 10.6 | 88.2 | 1.6 | 2.3 |
| 100 mg/mL | Batch 100-A | 11.2 | 82.3 | 1.7 | 3.2 |
| 10 kL (n = 2 lots) | Batch 100-B | 9.0 | 83.7 | 1.7 | 3.7 |
| 150 mg/mL | Batch 150-1 | 7.3 | 85.6 | 1.6 | 3.8 |
| 10 kL (n = 2 lots) | Batch 150-2 | 7.2 | 85.6 | 1.6 | 3.7 |

G0-G1cNAc: Biantennary core structure with fucose attached to the N-linked N-acetyl glucosamine, one N-acetyl glucosamine on one branch of the core structure and no terminal galactose.
G0: Biantennary core structure with fucose attached to the N-linked N-acetyl glucosamine, one N-acetyl glucosamine on each branch of the core structure and no terminal galactose.
G1: Biantennary core structure with fucose attached to the N-linked N-acetyl glucosamine, one N-acetyl glucosamine on each branch of the core structure and terminal galactose on one branch of the core structure.

All lots consist primarily of G0 and G0-GlcNAc (G0 lacking GlcNAc on one arm of the biantennary structure), which is representative of the DAC HYP process. Sialylated oligosaccharides elute at approximately 68 minutes and are below 1.0% in all lots tested. The uncharacterized oligosaccharide referred to as Peak 3 was present in similar abundance in all lots tested.

7.6.15. Oxidation

DAC HYP lots were evaluated for potential methionine oxidation, by monitoring oxidized and non-oxidized tryptic peptides present in the peptide maps. The peak areas of the non-oxidized and oxidized forms of each methionine containing peptide were determined using the mass spectra extracted ion chromatograms. For each methionine residue, the percent oxidized methionine was calculated by dividing the mass spectra peak area of the oxidized peptide by the sum of the peak areas of the oxidized and non-oxidized peptides.

As shown in Table 26 below, methionine oxidation results for the 150 mg/mL lots and five 100 mg/mL lots were comparable:

TABLE 26

Oxidation Results (LC = light chain; HC = heavy chain; M = methionine)

| Lots | | Percent Oxidation | | | | | |
|---|---|---|---|---|---|---|---|
| | | LC M4 | LC M32 | HC M34 | HC M 81 | HC M251 | HC M427 |
| 100 mg/mL | Batch 100-1 | 0.8 | 0.6 | 0.5 | 0.6 | 3.8 | 1.1 |
| | Batch 100-2 | 0.9 | 0.7 | 0.6 | 0.7 | 3.7 | 1.3 |
| | Batch 100-3 | 0.8 | 0.7 | 0.5 | 0.7 | 4.0 | 1.3 |
| | Batch 100-4 | 0.8 | 0.6 | 0.4 | 0.7 | 4.8 | 1.8 |
| | Batch 100-5 | 0.6 | 0.6 | 0.3 | 0.6 | 4.6 | 1.5 |
| | Average | 0.8 | 0.7 | 0.5 | 0.7 | 4.2 | 1.4 |
| | Standard Deviation | 0.1 | 0.1 | 0.1 | 0.1 | 0.5 | 0.3 |
| | Minimum | 0.6 | 0.6 | 0.3 | 0.6 | 3.7 | 1.1 |
| | Maximum | 0.9 | 0.7 | 0.6 | 0.7 | 4.8 | 1.8 |
| 150 mg/mL | Batch 150-1 | 0.6 | 0.6 | 0.4 | 0.5 | 3.5 | 0.9 |
| | Batch 150-2 | 0.8 | 0.7 | 0.4 | 0.7 | 4.3 | 1.6 |

Heavy chain Met251 and Met427 are the most labile and exhibits the greatest degree of oxidation. Among the lots tested concurrently to evaluate comparability, oxidation levels for Met251 and Met427 did not exceed 4.8% and 1.8%, respectively.

7.6.16. Binding Potency (CD25 Binding)

DAC HYP 150 mg/mL and 100 mg/mL lots were evaluated for binding to the alpha subunit of the IL-2 receptor (CD25) via ELISA as a measure of potency as part of release testing. Microtiter plates were immobilized with soluble CD25 and incubated with varying amounts of DAC HYP. Bound DAC HYP was detected using a horseradish peroxidase-conjugated goat anti-human IgG antibody in tandem with 3,3',5,5'-tetra-methyl benzidine substrate. Resulting absorbance values were plotted against the $\log_{10}$ of DAC HYP concentration using a 4-parameter fit and percent relative potency values were generated using parallel line analysis.

Drug substance results are summarized the table below:

TABLE 27

Potency by ELISA Results

| | | Potency (% of Reference Standard) |
|---|---|---|
| 100 mg/mL (n = 24 lots) | Average | 101 |
| | Standard Deviation | 14 |
| | Minimum | 78 |
| | Maximum | 129 |
| 150 mg/mL | Batch 150-1 | 86 |
| | Batch 150-2 | 105 |

The binding potency results of the 150 mg/mL lots were comparable to those of the 100 mg/mL lots.

7.6.17. Surface Plasmon Resonance (CD25 Binding)

Surface plasmon resonance analysis was performed to determine the affinity constant ($K_D$) for the binding interaction of DAC HYP to the alpha subunit of the IL-2 receptor (CD25).

Goat anti-human IgG Fc antibody was immobilized on a chip surface to capture DAC HYP samples, after which soluble CD25 was injected at various concentrations in duplicate over captured DAC HYP using an automated method. Binding data were collected and corrected using a reference flow cell and buffer blank, and fit with BIA Evaluation software using a 1:1 Langmuir model to obtain equilibrium constants.

Results for DAC HYP 150 mg/mL lots and Reference Standard RS0801 are summarized in Table 28:

TABLE 28

Surface Plasmon Resonance Results

| Lots | Ka (1/M*s) | Kd (1/s) | KD (M) | % RS KD |
|---|---|---|---|---|
| RS0801 ("RS") | $3.3 \times 10^5$ | $1.5 \times 10^{-4}$ | $4.4 \times 10^{-10}$ | Not Applicable |
| Batch 150-1 | $3.3 \times 10^5$ | $1.5 \times 10^{-4}$ | $4.6 \times 10^{-10}$ | 96 |
| Batch 150-2 | $3.4 \times 10^5$ | $1.5 \times 10^{-4}$ | $4.4 \times 10^{-10}$ | 100 |

The association constant ($k_a$), dissociation constant ($k_d$), and affinity constant ($K_D$) values of the 150 mg/mL lots were comparable to those of Reference Standard RS0801.

7.6.18. Functional Potency

DAC HYP 150 mg/mL and 100 mg/mL lots were evaluated for functional potency as part of release testing. The functional potency assay measures the inhibition of IL-2 induced T-cell proliferation by binding of DAC HYP to the alpha subunit of the IL-2 receptor (CD25). In the presence of IL-2, varying amounts of DAC HYP were incubated with KIT-225 K6 cells (Hori et al., 1987, Blood 70:1069-1072) expressing the IL-2 receptor. Inhibition of T-cell proliferation by DAC HYP was subsequently detected using alamar blue. Resulting fluorescence values were plotted against the $\log_{10}$ of DAC HYP concentrations using a 4-parameter fit and percent relative potency values were generated using parallel line analysis.

The functional potency results are summarized in Table 29:

TABLE 29

Functional Potency Results

| | | Potency (% of Reference Standard) |
|---|---|---|
| 100 mg/mL (n = 24 lots) | Average | 98 |
| | Standard Deviation | 12 |
| | Minimum | 73 |
| | Maximum | 121 |

TABLE 29-continued

| Functional Potency Results | | |
|---|---|---|
| | | Potency (% of Reference Standard) |
| 150 mg/mL | Batch 150-1 | 101 |
| | Batch 150-2 | 95 |

The functional potency results of the 150 mg/mL lots were comparable to those of the 100 mg/mL lots.

7.6.19. Antibody Dependent Cellular Cytotoxicity

Two lots of DAC HYP 150 mg/mL formulations were evaluated relative to that of Reference Standard RS0801 100 mg/mL DAC HYP.

IL-2 receptor expressing KIT-225 K6 cells were labeled with $^{51}$Cr, and subsequently incubated with DAC HYP. Human effector cells (PBMC) were added in varying amounts to achieve different effector to target cell (KIT-225 K6) ratios. Fc receptor bearing monocytes interact with the DAC HYP Fc domain and subsequently cause target cell lysis. The degree of cytotoxicity was determined by measuring the release of $^{51}$Cr from target cells and was expressed as a percentage of maximum cell lysis.

PBMCs from multiple donors were utilized for each sample. For each donor, the percent ADCC activity of the sample was calculated relative to that of Reference Standard RS0801 based on percent cytotoxicity. ADCC results are summarized in Table 30 below:

TABLE 30

| ADCC Results | | | | | |
|---|---|---|---|---|---|
| | % Cytotoxicity (Relative to Reference Standard RS0801) | | | | |
| Lot | Donor #1 | Donor #2 | Donor #3 | Average | Standard Deviation |
| Batch 150-1 | 93 | 79 | 76 | 83 | 9 |
| Batch 150-2 | 93 | 92 | 80 | 88 | 7 |

Response curves for the 150 mg/mL lots, Reference Standard RS0801, positive and negative control antibodies and a control without antibody (for Antibody Independent Cellular Cytotoxicity or AICC) are shown in FIG. 20.

The ADCC activity of the 150 mg/mL lots was comparable to that of Reference Standard RS0801.

7.6.20. Residual Protein A

Residual Protein A may be determined by an ELISA method, where standards, sample controls, a plate blank, and test samples are diluted with a denaturing buffer and placed into a boiling water bath to dissociate Protein A and denature and precipitate daclizumab. After boiling, standards, controls, and samples are cooled, centrifuged, and added to a micro-titer plate coated with polyclonal anti-Protein A capture antibody. Residual Protein A present in the samples is then detected using a biotinylated anti-Protein A antibody in tandem with streptavidin alkaline phosphatase and P-nitrophenyl phosphate (PNPP) substrate. The plate is analyzed in a spectrophotometric plate reader and a log-log standard curve is generated, against which the concentration of Protein A is determined. Test sample results are reported in parts per million (ppm) units. Parts per million results are calculated by dividing the ng/mL Protein A result by the antibody concentration of the test sample in mg/mL.

7.6.21. DNA Content

Detection of mouse DNA is determined at a contract laboratory using a quantitative polymerase chain reaction (Q-PCR) test method. In the method, the sample is subjected to DNA extraction. The sample extract is then analyzed by Q-PCR using mouse specific primers and probe to amplify a specific fragment of a repetitive element of mouse DNA. Amplification of the DNA results in a fluorescence signal that is detected. The DNA in the sample is quantitatively measured by comparison to a standard curve generated using known amounts of mouse DNA. Results are expressed in picograms of DNA per milligram of antibody. The average DNA content in various lots of DAC HYP drug product are summarized in Table 17.

7.6.22. Host Cell Proteins (HCP)

Residual host cell proteins in the product are quantified using a commercially available kit. An affinity purified goat polyclonal antibody to NS0 cell lysate is used for both the capture and detection of NS0 HCP. The HCP standard is produced by collecting cell free harvest material from a mock production run. A standard curve is prepared using an HCP working standard and samples containing HCP are serially diluted to target the range of the standard curve. Standards, sample controls, and test samples are added to an anti-NS0 HCP polyclonal antibody coated plate. Host cell proteins are then detected with an anti-NS0 HCP polyclonal antibody conjugated to horseradish peroxidase (HRP) in tandem with 3,3',5,5'-tetra-methyl benzidine (TMB) substrate. The plate is then analyzed in a spectrophotometric plate reader and a four parameter curve fit is generated to quantitate the amount of HCP in the samples.

The results for the NS0 HCP ELISA assay are reported in parts per million (ppm) units. Parts per million results are calculated by dividing the ng/mL HCP result by the antibody concentration in mg/mL. The average HCP of various lots of DAC HYP drug product are summarized in Table 17.

7.6.23. Polysorbate 80 Concentration

Polysorbate 80 is quantitated using a spectrophotometric method that is based on the formation of a colored cobalt-thiocyanate complex with polysorbate 80. A standard curve is constructed using a series of polysorbate 80 standards. The polysorbate 80 concentration in the sample is determined from the standard curve. The ranges of polysorbate concentrations of various lots of DAC HYP drug product are summarized in Table 17.

7.6.24. Osmolality

Osmolality is measured using a vapor pressure depression osmometer. Prior to sample analysis the osmometer is calibrated using osmolality standards that bracket the expected osmolality of the sample. The osmolality ranges of various lots of DAC HYP drug product are summarized in Table 17.

7.6.25. Conclusions

The physicochemical and biological analyses conducted provide a comprehensive evaluation of DAC HYP 150 mg/mL and DAC HYP 100 mg/mL formulations. The physicochemical and biological characteristics of all lots tested to date are comparable.

For all DAC HYP lots, the first 15 amino acids of the heavy and light chains determined by N-terminal sequencing, peptide maps and molecular weight analyses were consistent with the daclizumab gene sequences.

The aggregate levels and size distribution of aggregate species in all 150 mg/mL and 100 mg/mL lots tested, as determined by SEC-MALS and SV-AUC were comparable, as were their purity as tested by gel electrophoresis.

The charge isoform distribution of the 150 mg/mL lots was similar to that of the 100 mg/mL lots, with only slight differences in the relative amounts of the pE/VHS (150 mg/mL lots=31% pE/VHS; 100 mg/mL lots=34 to 42% pE/VHS) and Q/VHS (150 mg/mL lots=11 to 12% Q/VHS; 100 mg/mL lots=4 to 9% Q/VHS) N-terminal isoforms. The characteristics of DAC HYP are as follows:

N-terminal Isoforms by CEX:

pE/pE: 31-46% pE/Q: 7-12% pENHS: 31-42%

QNHS: 3-12%

VHSNHS: 1-17%

C-terminal Isoforms by CEX:

0K: 53-80%

1K: 14-28%

2K: 5-19%

The N-linked glycan distribution of DAC HYP is as follows:

G0-GlcNAc: 7.2-14.6%

G0: 80.9-88.2%

Peak 3: 1.3-1.7%

G1: 1.4-3.8

The oxidation levels measured for DAC HYP were low.

DAC HYP is biologically active, as confirmed in ELISA and surface plasmon resonance CD25 binding experiments, as well as functional to inhibit IL-2 induced T-cell proliferation. DAC HYP is also characterized by a low level of aggregation upon storage.

7.7. DAC HYP Stability

High concentration DAC HYP formulations are stable upon storage. The following tables provide stability data for 150 mg/mL DAC HYP drug substance lots.

Table 31 below provides stability data following storage in 50 mL bags at the recommended conditions (2-8° C.). Table 32 below provides accelerated stability data storage in 50 mL bags at 23-27° C. Table 33 below provides stressed stability data.

TABLE 31

Primary Real-Time Stability of DAC HYP Drug Substance, 150 mg/mL (Batch A)

| Time Point (Months) | Color and Appearance | pH | Conc. | CEX | SEC % Main Peak | SEC % Aggregate | % Purity* | Binding Potency | Functional Potency |
|---|---|---|---|---|---|---|---|---|---|
| 0 | Pass[a] | 6.0 | 148 | Pass[b] | 99.4 | 0.6 | 97.3 | 86 | 101 |
| 1 | Pass | 6.0 | 149 | Pass | 99.0 | 1.0 | 97.0 | 90 | 94 |
| 2 | Pass | 6.0 | 149 | Pass | 99.0 | 1.0 | 96.9 | 91 | 108 |
| 3 | Pass | 6.0 | 149 | Pass | 98.9 | 1.1 | 97.3 | 102 | 104 |
| 6 | Pass | 6.0 | 149 | Pass | 98.8 | 1.2 | 97.5 | 94 | 79 |
| 9 | Pass | 6.0 | 151 | Pass | 98.5 | 1.4 | 97.3 | 107 | 110 |
| 12 | Pass | 6.0 | 152 | Pass | 98.4 | 1.5 | 95.7 | 96 | 98 |

[a]Pass criteria: Colorless, clear to slightly opalescent liquid, essentially free of visible particles.

[b]Pass criteria: Chromatogram profile consistent with reference.

*SDS-PAGE (colloidal blue stain)

TABLE 32

Primary Accelerated Stability of DAC HYP Drug Substance, 150 mg/mL (Batch A)

| Time Point (Months) | Color and Appearance | pH | Conc. | CEX | SEC % Main Peak | SEC % Aggregate | % Purity* | Binding Potency | Functional Potency |
|---|---|---|---|---|---|---|---|---|---|
| 0 | Pass[a] | 6.0 | 148 | Pass[b] | 99.4 | 0.6 | 97.3 | 86 | 101 |
| 1 | Pass | 6.0 | 150 | Pass | 98.5 | 1.4 | 97.0 | 93 | 111 |
| 2 | Pass | 6.0 | 152 | Pass | 98.3 | 1.5 | 96.0 | 110 | 105 |
| 3 | Pass | 6.0 | 153 | Pass | 98.2 | 1.6 | 96.0 | 100 | 108 |
| 6 | Pass | 6.0 | 155 | Pass | 97.7 | 1.8 | 95.2 | 94 | 109 |

[a]Pass criteria: Colorless, clear to slightly opalescent liquid, essentially free of visible particles.

[b]Pass criteria: Chromatogram profile consistent with reference.

*SDS-PAGE (colloidal blue stain)

TABLE 33

Primary Stressed Stability of DAC HYP Drug Substance, 150 mg/mL (Batch A)

| Time Point (Months) | Color and Appearance | pH | Conc. | CEX | SEC % Main Peak | SEC % Aggregate | % Purity* | Binding Potency | Functional Potency |
|---|---|---|---|---|---|---|---|---|---|
| 0 | Pass | 6.0 | 148 | Pass | 99.4 | 06 | 97.3 | 86 | 101 |
| 1 | Pass | 6.0 | 153 | Pass | 97.8 | 18 | 94.8 | 85 | 93 |
| 2 | Pass | 6.0 | 159 | Pass | 97.1 | 22 | 90.0 | 102 | 108 |

a. Pass criteria: Colorless, clear to slightly opalescent liquid, essentially free of visible particles.

b. Pass criteria: Chromatogram profile consistent with reference.

*SDS-PAGE (colloidal blue stain)

7.8. Comparison Between Different Forms of Daclizumab

Hoffman-La Roche, Inc. ("Roche") manufactured an intravenous formulation of a daclizumab marketed as ZENAPAX™ for treatment of allograft rejection that has been discontinued. DAC Penzberg is a 100 mg/ml subcutaneous formulation of daclizumab used in clinical trials by PDL BioPharma (see CHOICE study described in Section 7.9.1 below).

A comparison between the DAC HYP, ZENAPAX DAC and DAC Penzberg formulations is shown in Table 34. In the table, the formulation buffer is the buffer the DAC was diafiltered into to yield the ultimate formulation. Accordingly, the noted concentrations are nominal concentrations:

TABLE 34

DAC HYP vs. ZENAPAX DAC and DAC Penzberg

| Material | Formulation | Conc. (mg/mL) |
|---|---|---|
| ZENAPAX DAC | 67 mM sodium phosphate<br>79 mM sodium chloride<br>0.02% polysorbate 80<br>pH 6.9 | 5 |
| DAC Penzberg | 40 mM succinate | 100 |
| DAC HYP | 100 mM sodium chloride<br>0.03% polysorbate 80<br>pH 6.0 | 100 or 150 |

Various characteristics DAC HYP were compared to those of ZENAPAX DAC and DAC Penzberg.

A comparison between the glycosylation of DAC HYP vs. ZENAPAX DAC is shown in FIG. 21. The analysis of exemplary lots of the three forms of daclizumab is set forth in Table 35:

TABLE 35

Comparison of glycosylation of DAC HYP vs. ZENAPAX DAC vs. DAC Penzberg

| Source | G0 (%) | G1 (%) | G2 (%) | G0-GlcNAc |
|---|---|---|---|---|
| ZENAPAX DAC | 44 | 27 | 6 | 6 |
| DAC Penzberg | 39 | 31 | 8 | 3 |
| DAC HYP | 84 | 2 | <1 | 9 |

DAC HYP also has significantly lower levels of mannose glycosyls (e.g., Man5, Man6, Man7) and lower levels of sialylated glycosyls than ZENAPAX DAC (see, e.g., FIG. 21).

Antibody dependent cell-mediated cytotoxicity (ADCC) is an in vitro assay that can be used to assess the Fc dependent activity and the potential cytotoxic effects of antibody-target binding. Using peripheral blood mononuclear cells (PBMC) from six healthy donors as effector cells and the CD25-expressing KIT225/K6 cell line as the target cells, the ADCC activity of the various daclizumab preparations was assayed in both a variable an effector to target cell ratio format or a variable antibody concentration format.

For the variable effector to target cell ratio format, $^{51}$Cr-labeled KIT225/K6 cells (12,500 cells/well) were pre-incubated with 1 μg/mL of antibody (final concentration) for 30 minutes at 4° C. in V-bottom 96-well plates in a volume of 100 μL of ADCC Assay Medium (containing 435 mL RPMI-1640; 5.0 mL L-glutamine; 50 mL heat inactivated fetal bovine serum; 500 μl 1000× 2-mercaptoethanol; 5.0 mL of penicillin-streptomycin (100×); and 5.0 mL of HEPES (1 M stock) per 500 mL); control cells were incubated in ADCC Assay Medium in the absence of antibody for subsequent determination of antibody-independent $^{51}$Cr release.

The PBMC (effectors) were diluted serially in ADCC Assay Medium in a separate 96-well polypropylene plate, yielding cell concentrations per 100 μL of 6.25×10$^{5}$ cells, 3.13×10$^{5}$ cells, 1.56×10$^{5}$ cells, 7.81×10$^{4}$ cells, or 3.91×10$^{4}$ cells. A volume of 100 μL per well of PBMC suspension was added to the plates containing $^{51}$Cr-labeled KIT225/K6 and antibodies, yielding Effector to Target (E:T) ratios of 50:1, 25:1, 12.5:1, 6.25:1 and 3.13:1. In addition, a volume of 100 μL per well of ADCC Assay Medium alone (no effector) was added to $^{51}$Cr-labeled KIT225/K6+mAbs, to determine spontaneous release of $^{51}$Cr. The assay plates were spun at 50 RCF for 2 minutes and incubated at 37° C. in a 7.5% $CO_2$ incubator for 4 hours.

Thirty minutes before the end of the 4-hour incubation, a volume of 25 μL of 8% TritonX-100 was added to the appropriate control wells to determine maximum release of $^{51}$Cr from target cells. Upon completion of the 4-hour incubation, the plates were spun at 350 RCF for 5 minutes and a volume of 100 μL of supernatant from each well was transferred to mini-tubes. Each mini-tube was inserted into a scintillation vial and counted for 1 minute in a Beckman Gamma 5500B counter, or equivalent.

For the variable antibody concentration format, $^{51}$Cr-labeled KIT225/K6 cells (12,500 cells/well; targets) were pre-incubated with various doses of antibodies (5, 1, 0.2, 0.04, 0.008, and 0.0016 μg/mL) of mAbs (final concentration) for 30 minutes at 4° C. in V-bottom 96-well plates in a volume of 100 μL of ADCC Assay Medium. The control cells were incubated with ADCC Assay Medium alone (no mAb) for subsequent determination of antibody-independent $^{51}$Cr release.

The PBMC (effectors) were diluted serially in ADCC Assay Medium, in a separate 96-well polypropylene plate to a concentration of 3.13×10$^{5}$ cells/100 μL. A volume of 100 μL per well of PBMC suspension was added to the plates containing $^{51}$Cr-labeled KIT225/K6+mAbs, yielding an Effector to Target (E:T) ratio of 25:1. In addition, a volume of 100 μL per well of ADCC Assay Medium alone (no effector) was added to $^{51}$Cr-labeled KIT225/K6+mAbs, to determine spontaneous release of $^{51}$Cr. The assay plates were spun at 50 RCF for 2 minutes and incubated at 37° C. in a 7.5% $CO_2$ incubator for 4 hours.

Thirty minutes before the end of the 4-hour incubation, a volume of 25 μL of 8% TritonX-100 was added to the appropriate control wells to determine maximum release of $^{51}$Cr from target cells. Upon completion of the 4-hour incubation, the plates were spun at 350 RCF for 5 minutes and a volume of 100 μL of supernatant from each well was transferred to mini-tubes. Each mini-tube was inserted into a scintillation vial and counted for 1 minute in a Beckman Gamma 5500B counter, or equivalent.

The ADCC results are shown in FIG. 22A (variable effector to target cell ratio format) and FIG. 22B (variable antibody concentration format). These data show that the maximal ADCC activity achieved with DAC HYP tested at graded concentrations was approximately 30-40% lower than the activity elicited by the same concentration of ZENAPAX DAC and DAC Penzberg.

A comparison of the charge isoform profiles (corresponding to the N terminal variants) of DAC HYP vs. ZENAPAX DAC vs. DAC Penzberg is shown in FIG. 23.

7.9. DAC HYP Clinical Trials 7.9.1. CHOICE Study

The CHOICE trial was a phase 2, randomized, double-blind, placebo-controlled trial of daclizumab added to interferon beta therapy in 230 patients with relapsing MS. The trial tested two dosing regimens of 100 mg/ml DAC Penzberg (see Section 7.8 above for a description of the product) administered as a subcutaneous injection: 1 mg/kg daclizumab administered every four weeks and 2 mg/kg daclizumab administered every two weeks. Results of the study showed that the addition of daclizumab, administered at 2 mg/kg every two weeks to interferon beta therapy, significantly reduced new or enlarged gadolinium-enhancing lesions at week 24, when compared to interferon beta therapy alone.

The results of the CHOICE study are described in Wynn et al., 2010, Lancet Neurol. 9(4):381-90. Daclizumab treatment was generally well-tolerated. Common adverse events were similar in all treatment arms. Grade 3 adverse events were observed in 24 percent of DAC/IFNβ-treated patients and 14 percent of placebo/IFNβ-treated patients. The most frequent grade 3 adverse events were infections, which occurred in 7 percent of DAC/IFNβ-treated patients and 3 percent of placebo/IFNβ-treated patients. There were no opportunistic infections or deaths, and all infections resolved with standard therapies.

The CHOICE trial demonstrated that, in MS patients on a background of IFNβ-a1 therapy, daclizumab was well-tolerated and caused a dose dependent reduction in new/enlarged gadolinium-enhancing (Gd+) lesions by 72% compared to IFNβ-a1 alone. Clinical efficacy was associated with a marked expansion of immunoregulatory $CD56^{bright}$ natural killer (NK) cells.

7.9.2. SELECT Study

A randomized, double-blind, placebo-controlled dose ranging study (SELECT) was conducted to determine the safety and efficacy of two different dosage levels of DAC HYP.

Overview.

The study was conducted at 76 centers in the Czech Republic, Germany, Hungary, India, Poland, Russia, Ukraine, and the United Kingdom. The care of each patient involved a treating neurologist, a treating nurse (or study coordinator), an examining neurologist, an MRI technician, and a pharmacist (or authorized designee). A centralized Interactive Voice Response System was used for randomization across all sites. A protocol-defined interim futility analysis was performed after 150 patients completed the Week 24 visit.

Patients.

Eligibility criteria included patients 18-55 years of age with clinically definite relapsing remitting multiple sclerosis (according to 2005 McDonald criteria #1-4; see, Polman et al, 2005 *Ann Neurol* 58:840-846), a baseline Expanded Disability Status Scale (EDSS) of 0-0.50 (Kurtzke, 1983, Neurology 33(11):1444-52) and at least one MS relapse in the 12 months before randomization or one new Gd+ lesion on brain MRI performed within the 6 weeks prior to randomization, were randomized to receive either DAC HYP (150 mg or 300 mg) or placebo as a subcutaneous injection once every 4 weeks for 52 weeks. Patients with child-bearing potential needed to practice effective contraception.

Patients were excluded if they had primary-progressive, secondary-progressive, or progressive-relapsing MS, a history of malignancy, severe allergic or anaphylactic reactions or known drug hypersensitivity, or other significant medical conditions that, in the opinion of the investigator, would preclude administration of DAC HYP. Additional exclusion criteria included previous treatment with DAC HYP or ZENAPAX™, total lymphoid irradiation, cladribine, mitoxantrone, T-cell or T-cell receptor vaccination or any therapeutic mAb, except natalizumab or rituximab. At the time of randomization, patients could not have received treatment with cyclophosphamide or rituximab within the previous year; natalizumab, cyclosporine, azathioprine, methotrexate, intravenous immunoglobulin, plasmapheresis or cytapheresis within the previous 6 months; or live virus vaccine, treatment with glatiramer acetate, IFNβ, interferon-alpha, 3 months before randomization; or corticosteroids, 4-aminopyridine or related products within the previous 30 days.

Characteristics of the groups were as follows:

| | | DAC HYP | |
|---|---|---|---|
| | Placebo (n = 204) | 150 mg (n = 208) | 300 mg (n = 209) |
| **Demographics** | | | |
| Age, years, mean (SD) | 36.6 (9.0) | 35.3 (8.9) | 35.2 (8.7) |
| Gender, female, n (%) | 128 (63) | 140 (67) | 134 (64) |
| Race, White, n (%) | 197 (97) | 202 (97) | 200 (96) |
| **MS disease characteristics** | | | |
| No prior MS therapy, n (%)* | 155 (76) | 155 (75) | 162 (78) |
| Years since MS diagnosis, mean (median) | 4.1 (2.0) | 4.5 (3.0) | 3.7 (3.0) |
| Number relapses past year, mean (SD) | 1.3 (0.6) | 1.4 (0.7) | 1.3 (0.7) |
| Baseline EDSS, mean (SD) | 2.7 (1.2) | 2.8 (1.2) | 2.7 (1.2) |
| **MRI brain lesions** | | | |
| ≥1 Gd+ lesions, n (%)** | 90 (44) | 106 (51) | 74 (35) |
| No. Gd+ lesions, mean (SD) | 2 (4.5) | 2.1 (3.5) | 1.4 (3.3) |
| No. T2 hyperintense lesions, mean (SD) | 40 (32) | 45 (35) | 36 (31) |

DAC, daclizumab;
HYP, high yield process;
SD, standard deviation;
MS, multiple sclerosis;
EDSS, Expanded Disability Status Scale;
Gd+, gadolinium-enhancing.
*Patients who had not received prior MS treatment with the exception of steroids.
**Placebo n = 203,
DAC HYP 150 mg n = 206,
DAC HYP 300 mg n = 206 (all p values were >0.05 for intergroup comparison).

Endpoints.

The primary objective of this study was to determine whether DAC HYP monotherapy reduced MS relapses as defined by the annualized relapse rate (ARR) at Week 52. Relapses were defined as new or recurrent neurologic symptoms (not associated with fever or infection), lasting >24 hours, and accompanied by new neurological findings upon assessment by the examining neurologist. An Independent Neurology Evaluation Committee (INEC), consisting of three blinded MS neurologists, evaluated all suspected relapses to adjudicate whether the protocol definition of MS relapse was satisfied. Only INEC approved relapses were included in the primary analysis.

The secondary objectives were to determine whether DAC HYP was effective in reducing the number of cumulative new Gd+ lesions on brain MRI scans performed at Weeks 8, 12, 16, 20 and 24 in a subset of patients; reducing the number of new or newly-enlarging T2 hyperintense lesions at Week 52; reducing the proportion of relapsing patients between baseline and Week 52; and improving quality of life (QoL), as measured by the change from baseline in the 29-item Multiple Sclerosis Impact Scale (MSIS-29) (Hobart et al., 2001, Brain 124(Pt 5):962-73) physical impact score at Week 52. Confirmed disability progression was assessed by change in EDSS score between baseline and Week 52 (1.0-point increase in EDSS for baseline EDSS≥1.0 or 1.5 point increase for baseline EDSS=0 that was sustained for 12 weeks). EDSS evaluations were conducted every 12 weeks, and at Weeks 20, 52, 60 and 72.

Additional QoL endpoints were the subject's global assessment of well being, as assessed by the EQ-Visual Analogue Scale (EQ-VAS) (EuroQol-a new facility for the measurement of health-related quality of life, 2011, Accessed 17.11.11, at http://www.euroqol.org/); and change in the EQ-5D health survey (EuroQol-a new facility for the measurement of health-related quality of life, 2011, Accessed 17.11.11, at http://www.euroqol.org/); 12-item short form health survey SF-12 (Ware et al., 1996, Medical Care 34(3):220-33) and the MSIS-29 psychological scale at Week 52 (Hobart et al., 2001, Brain 124(Pt 5):962-73).

Additional MRI endpoints were the number of Gd+ lesions at Week 52, the volume of total and new or newly enlarging T2 hyperintense lesions at Weeks 24 and 52, the volume of total and new T1 hypointense lesions "black holes" (defined as lesions that were iso/hypointense to gray matter and that did not enhance after gadolinium administration) at Weeks 24 and 52, and the percentage change in whole brain volume assessed by the SIENA method (Smith et al., 2001, J Comput Assist Tomogr 25(3):466-75).

Lymphocyte subsets were measured at multiple time points using a validated FACS assay. $CD56^{bright}$ NK cells were defined as $CD3^{-}CD16^{+}/CD56^{bright}$ lymphocytes. Immunogenicity to DAC HYP was assessed using a standard ELISA to screen for anti-drug antibodies and a cellular assay was then used to test for neutralizing antibodies on all positive samples.

Statistical Analyses.

A sample size of approximately 600 patients was selected to have 90% power to detect a 50% reduction in the ARR between a DAC HYP treatment group and the placebo group, estimated from simulations assuming a negative binomial distribution with a 10% drop out rate, a 5% type 1 error rate and a two sided test. The ARR in the placebo group was assumed to be 0.476, based on recently completed trials in RRMS subjects. All reported p-values are two-tailed.

The primary analysis evaluated differences in the ARR between each DAC HYP group versus placebo. Relapses that occurred after rescue treatment with alternative MS medication were censored. The difference was evaluated using a negative binomial regression model adjusting for the number of relapses in the year before study entry, baseline EDSS (EDSS≤0.5 versus EDSS>2.5) and baseline age (≤35 versus>35 years). Secondary analyses tested for treatment differences using negative binomial regression (number of new Gd+ lesions between weeks 8 and 24; number of new or newly enlarging T2 hyperintense lesions), a Cox proportional hazards model (time to first relapse, time to disease progression), and an analysis of variance model (change in EDSS, volume of new or newly enlarging T2 lesions, volume of new T1 hypointense lesions, QoL) and a proportional odds model (number of new Gd+ lesions at Week 52). The proportion of patients who were relapse-free was estimated from the Kaplan-Meier survival curve distribution.

For the cumulative number of new Gd+ lesions between Weeks 8 and 24, if a patient missed 1 or 2 consecutive scans, or all scans, the last non-baseline observation was carried forward, or the mean number of lesions within each treatment group was used, respectively. For other MRI endpoints, missing data was imputed using the mean within the treatment group. For MSIS-29, if the patient was missing <10 items, the mean of the non missing items was used to impute the score. For patients missing ≥10 items and for other QoL measures, a random slope and intercept model was used to estimate missing data.

Statistical testing for efficacy endpoints utilized separate comparisons of the DAC HYP 300 mg group versus placebo and the DAC HYP 150 mg group versus placebo. A sequential closed testing procedure was used to control the overall Type I error rate due to multiple comparisons.

Efficacy analyses were evaluated in the intent-to-treat (ITT) population which included all patients who underwent randomization. However, 21 patients from a single study center were prospectively excluded from the ITT population prior to study completion due to evidence of incorrect dosing at the center, which was identified prior to study completion (all patients at the center were receiving active treatment). In a sensitivity analysis, all primary and secondary efficacy analyses were repeated using all randomized patients. All safety analyses were based on the safety population, which was defined as all patients who received at least one dose of study medication and who had at least one post randomization assessment.

A preplanned futility analysis was performed after 150 subjects completed the Week 24 visit, to provide an opportunity to stop if the hypothesized effects of DAC HYP were not evident. Since efficacy may change over the duration of the study there was no plan to stop the study early for evidence of superiority at the time of the futility analysis. Futility was assessed by estimating separately the conditional power for both the cumulative number of new Gd+ lesions between weeks 8 and 24 and the ARR endpoint for each dose group. The Safety Monitoring Committee reviewed the data at the time of the analysis and based on the overall consistency of the data and the assessment of risk benefit recommended to continue the study.

Summary Results.

Eligible participants were randomized from Feb. 15, 2008 to May 14, 2010. Baseline characteristics were similar across the three treatment groups, although there was a trend for patients in the DAC HYP 150 mg group to have more T2 and Gd+T1 lesions than those in the DAC HYP 300 mg group. Across all randomized patients, a total of 577 (93%) completed the treatment period with similar proportions of DAC HYP and placebo-treated patients completing the study.

Detailed Results. Clinical Efficacy.

The ARR at 52 weeks (primary endpoint) was lower for patients randomized to DAC HYP 150 mg (0.21) or 300 mg (0.23), compared with placebo (0.46; Table 36), representing a 54% reduction versus placebo with DAC HYP 150 mg (95% CI, 31% to 69%, p<0.0001), and a 50% reduction versus placebo for DAC HYP 300 mg (95% CI, 26% to 66%, p=0.0002; Table 36). Over 52 weeks, the proportion of relapsing patients was reduced in the DAC HYP 150 mg (19%) and 300 mg (20%) groups relapsed versus 36% in the placebo group (p<0.001 for both comparisons) (Table 36). Compared with placebo, the risk of 3-month sustained disability progression at Week 52 was reduced by 57% (Hazard ratio=0.43; 95% CI, 0.21 to 0.88; p=0.021) in the DAC HYP 150 mg and by 43% (Hazard ratio=0.57; 95% CI, 0.30 to 1.09; p=0.091) in the DAC HYP 300 mg group.

A relative 4.0 improvement in the MSIS-29 physical score at Week 52 was observed for DAC HYP 150 mg versus placebo with a less marked change in the DAC HYP 300 mg patients, (p<0.0008 and p=0.1284 vs. placebo, respectively; Table 36). Similar improvements on other measures of health-related quality of life including measures of both physical and psychological function and overall health were also observed (Table 36).

TABLE 36

Clinical and MRI End Points by Treatment Group

| | Placebo (n = 196) | DAC HYP 150 mg (n = 201) | DAC HYP 300 mg (n = 203) | P Value DAC HYP 150 mg vs. Placebo | P Value DAC HYP 300 mg vs. Placebo |
|---|---|---|---|---|---|
| Clinical | | | | | |
| Number of Relapses | | | | | |
| 0 | 127 (65) | 163 (81) | 163 (80) | | |
| 1 | 52 (27) | 33 (16) | 33 (16) | | |
| 2 | 15 (8) | 5 (2) | 5 (2) | | |
| 3 | 2 (1) | 0 | 1 (<1) | | |
| ≥3 | 0 | 0 | 0 | <0.0001 | 0.0002 |
| ARR over 52 weeks (95% CI) | 0.46 (0.37-0.57) | 0.21 (0.16-0.29) | 0.23 (0.17-0.31) | | |
| Rate ratio (95% CI)* | | 0.46 (0.32-0.67) | 0.50 (0.35-0.72) | <0.0001 | 0.0002 |
| % patients who relapsed at 52 weeks | 36 | 19 | 20 | | |
| Hazard ratio (95% CI)† | | 0.45 (0.30-0.67) | 0.50 (0.35-0.72) | <0.0001 | 0.0003 |
| Disability progression at 3-months, % | 13.3 | 5.9 | 7.8 | | |
| Rate ratio (95% CI)†† | | 0.43 (0.21-0.88) | 0.57 (0.30-1.09) | 0.021 | 0.0905 |
| Mean change EDSS from baseline to wk 52 | 0.09 | −0.08 | 0.05 | 0.0102 | 0.4874 |
| MRI | | | | | |
| New Gd+ lesions between Weeks 8-24 | | | | | |
| # patients with data¶ | 104 | 101 | 102 | | |
| Mean no. (95% CI)‖ | 4.8 (3.6-6.4) | 1.5 (1.1-2.0) | 1.0 (0.7-1.5) | <0.0001 | <0.0001 |
| % reduction versus placebo (95% CI) | | 69 (52.4-80.4) | 78 (66-86.4) | | |
| New Gd+ lesions at Week 52 | | | | | |
| No. of patients with data | 195 | 199 | 200 | | |
| Mean no. | 1.4 | 0.3 | 0.2 | <0.0001 | <0.0001 |
| Odds Ratio (95% CI) | | 0.15 (0.09-0.25) | 0.12 (0.07-0.20) | <0.0001 | <0.0001 |
| New/newly enlarging T2 hyperintense lesions at Week 52 | | | | | |
| # patients | 195 | 199 | 200 | | |
| Mean no. (95% CI)** | 8.1 (6.7-9.9) | 2.4 (2.0-3.0) | 1.7 (1.4-2.2) | <0.0001 | <0.0001 |
| % reduction versus placebo, (95% CI) | | 70 (59.4-77.9) | 79 (71.3-84.2) | | |
| Percentage change from baseline in volume T2 hyperintense lesions at Week 52 | | | | | |
| # patients | 193 | 198 | 197 | | |
| Mean (SD)** | 27.3 (107.8) | −11.1 (12.1) | −12.5 (12.5) | <0.0001 | <0.0001 |
| Percentage change from baseline in volume of new T1 hyperintense lesions at Week 52 | | | | | |
| # patients | 195 | 199 | 200 | | |
| Mean (SD)** | 218.7 (400.2) | 116.7 (276.6) | 54.8 (153.1) | <0.0001 | <0.0001 |
| Percentage mean change in whole brain volume to Week 24 | | | | | |
| # patients | 194 | 198 | 200 | | |
| Mean (SD)∞ | −0.32 (0.729) | −0.41 (0.769) | −0.31 (0.678) | 0.0635 | 0.6261 |
| Percentage mean change in whole brain volume Week 24 to Week 52 | | | | | |
| # patients | 194 | 198 | 200 | | |
| Mean (SD)∞ | −0.74 (0.90) | −0.79 (0.83) | −0.70 (0.91) | 0.3263 | 0.4117 |
| Quality of life | | | | | |
| MSIS-29, change from baseline to Week 52,mean (SD)§ | | | | | |
| Physical Impact Score‡ | 3.0 (13.5) | −1.0 (11.8) | 1.4 (13.5) | 0.0008 | 0.1284 |
| Psychological Impact Score | 0.6 (14.4) | −1.8 (15.8) | −0.5 (15.3) | 0.0683 | 0.4338 |
| EQ-Visual Analogue Scale, change from baseline to Week 52, mean (SD)§ | −1.8 (13.2) | 2.9 (13.3) | 1.0 (12.8) | <0.0001 | 0.0149 |
| EQ-5D Summary Health Index, change from baseline to Week 52, mean (SD)§ | −0.04 (0.20) | 0.01 (0.18) | −0.02 (0.20) | 0.0091 | 0.3538 |
| SF-12, change from baseline to Week 52, mean (SD)§ | | | | | |
| Physical component | −0.4 (7.0) | 1.2 (7.3) | 0.5 (7.3) | 0.0116 | 0.1018 |
| Mental component | −1.4 (9.2) | 0.7 (9.6) | −0.1 (8.6) | 0.0118 | 0.2342 |

ARR, annualized relapse rate;

MSIS, Multiple Sclerosis Impact Scale;

Gd+, gadolinium-enhancing.

*P values estimated from a negative binomial regression model adjusted for number of relapses in 1-year period prior to study entry, baseline EDSS (≤2.5 vs. >2.5), and age (≤35 vs. >35).

†P value estimated from Cox-proportional hazards model adjusting for number of relapses in 1-year prior to entry, baseline EDSS, and age.

‡Lower scores indicate improvement.

§P value calculated using analysis of covariance for difference between treatment groups, controlling for baseline score.

¶MRI substudy, N = 307 (placebo, n = 104; DAC HYP 150 mg, n = 101; DAC HYP 300 mg, n = 102).

‖P value estimated from a negative binomial model adjusted for the baseline number of Gd+ lesions.

**P value estimated from a negative binomial model adjusted for the baseline number of T2 lesions.

††P value estimated from Cox-proportional hazards model adjusting for baseline EDSS and age.

ΔP value estimated from an analysis of covariance model adjusted for baseline EDSS.

‡‡P value estimated from a proportional odds model adjusted for the baseline number of Gd+ lesions.

∞P-value based on analysis of covariance on ranked data adjusted for baseline normalized brain volume.

MRI.

DAC HYP reduced new MS lesion activity, as defined by MRI, in both the entire study population and a subset with monthly MRIs performed between weeks 8 to 24 (Table 36). In contrast to the clinical endpoints, the point estimates of efficacy were marginally stronger in the 300 mg dose group compared to the 150 mg dose group even after adjustment for the potential baseline imbalances. Longitudinal analysis demonstrated that Gd+ lesion activity was higher in the 150 mg dose group compared to the 300 mg dose group in the first few months of treatment but was similar by week 52. (Table 36). Sensitivity analyses that included the 21 patients from the one excluded study site yielded similar results for all efficacy analyses.

Safety.

Adverse events (AEs) occurred in a similar proportion of patients in the DAC HYP 150 mg (73%), DAC HYP 300 mg (76%) and placebo (79%) groups (Table 37). Serious AEs, occurred in 26% of the placebo, 15% in the DAC HYP 150 mg and 17% in the DAC HYP 300 mg groups. Excluding MS relapses, SAEs occurred in 6%, 7% and 9% of patients in each group (Table 37). AEs that occurred in >5% of DAC HYP patients are shown in Table 37. The incidence of serious infections was 2% in DAC HYP-treated patients versus 0% in placebo. Among the 7 patients who had a serious infection while dosing was ongoing, 1 discontinued treatment due to the serious infection and 6 restarted treatment after the infection resolved. The incidence of cutaneous events was 18% in the DAC HYP 150 mg, 22% in the DAC HYP 300 mg, and 13% in the placebo groups (Table 37). Serious cutaneous events occurred in 1% of DAC HYP-treated patients. One DAC HYP-treated patient who was recovering from a serious rash died due to a complication of a psoas abscess. At autopsy, a psoas abscess, which had been previously undiagnosed, was found to involve a mesenteric artery and had resulted in local thrombosis and acute ischemic colitis. Five malignancies occurred during the trial: two cases of cervical carcinoma (1 each in the placebo and DAC HYP 150 mg group); one case of thyroid neoplasm in the DAC HYP 150 mg group was a non-serious thyroid nodule; and two cases of melanoma in the DAC HYP 300 mg group. The cases of melanoma were treated with local excision without reported recurrence.

TABLE 37

Adverse Events Summary

| | Placebo (n = 204) | DAC HYP 150 mg (n = 208) | DAC HYP 300 mg (n = 209) |
|---|---|---|---|
| Adverse event summary | | | |
| Any adverse event, n (%) | 161 (79) | 151 (73) | 159 (76) |
| Any serious adverse event, n (%) | 53 (26) | 32 (15) | 36 (17) |
| Any serious adverse event excluding MS relapse, n (%) | 12 (6) | 15 (7) | 19 (9) |
| Death, n | 0 | 1* | 0 |
| Common Adverse Events that Occurred in ≥5% of DAC HYP Patients During Treatment | | | |
| MS Relapse, n (%) | 76 (37) | 43 (21) | 41 (20) |
| Nasopharyngitis, n (%) | 31 (15) | 30 (14) | 29 (14) |
| Upper respiratory tract infection, n (%) | 14 (7) | 18 (9) | 21 (10) |
| Headache, n (%) | 20 (10) | 18 (9) | 20 (10) |
| Pharyngitis, n (%) | 8 (4) | 13 (6) | 13 (6) |
| Adverse events of interest | | | |
| Infections, n (%) | 89 (44) | 104 (50) | 112 (53) |
| Serious Infections, n (%) | 0 | 6 (3) | 3 (1) |
| Cutaneous events, n (%) | 27 (13) | 38 (18) | 45 (22) |
| Injection-site reaction, erthyma, | 3 (1) | 4 (2) | 4 (2) |
| Severe cutaneous events, n (%) | 0 | 2 (<1) | 2 (1) |
| Malignancy, n (%) | 1 (<1) | 2 (<1) | 2 (<1) |
| Incidence of ALT Abnormalities | | | |
| 1-3× ULN, n (%) | 64 (31) | 54 (26) | 62 (30) |
| 3-5× ULN, n (%) | 6 (3) | 7 (3) | 6 (3) |
| >5× ULN, n (%) | 1 (<1) | 9 (4) | 8 (4) |

ULN, upper limit of normal; ALT, alanine aminotransferase

Laboratory Findings.

Patients treated with DAC HYP had an increase in total NK cell count (cells/mm$^3$) compared with placebo at Week 52 (median: 42.0 (150 mg DAC HYP); 46.5 (300 mg DAC HYP); vs −4.5 placebo; p=<0.001). The increase in total NK cell numbers was related to a selective increase in CD56$^{bright}$ NK cells from a median of 7.77 at baseline to 44.84 at end of treatment. In contrast, there were only marginal changes in CD56$^{dim}$ NK cells (median changes from 122.68 to 123.70). Expansion of CD56$^{bright}$ NK cells was apparent at the first post-baseline time point (Week 4) in both DAC HYP arms versus placebo (p<0.0001). CD56$^{bright}$ NK cells expanded from a median of 0.6% of lymphocytes at baseline to 2.8% at Week 52. In contrast, patients treated with DAC HYP had a modest decrease in B-cell and total lymphocyte counts (Table 38). Both CD4$^+$ and CD8$^+$ T-cell counts decreased by approximately 7-10% at Week 52 in DAC HYP-treated patients and the CD4$^+$/CD8$^+$ ratio remained constant during treatment.

TABLE 38

| Changes in Lymphocyte Cell Counts Over 52 Weeks | | | |
|---|---|---|---|
| | | DAC HYP | |
| | Placebo (n = 179) | 150 m g(n = 184) | 300 mg (n = 186) |
| Total lymphocytes, mean cells/mm$^3$ (SD) | | | |
| Baseline | 1420.9 (450.3) | 1444.1 (441.9) | 1395.7 (471.4) |
| Week 24 | 1455.7 (468.7) | 1380.9 (426.4) | 1314.7 (366.3) |
| % Change Week 24 | 4.81 (29.48) | −1.30 (27.60) | −1.2 (29.01) |
| Week 52 | 1397.2 (414.4) | 1332.5 (398.4) | 1286.2 (446.8) |
| % Change Week 52 | 1.89 (26.60) | −3.63 (27.95) | −3.69 (27.74) |
| B cells, mean cells/mm$^3$ (SD) | | | |
| Baseline | 174.4 (91.9) | 175.5 (89.8) | 167.2 (89.6) |
| Week 24 | 187.4 (110.3) | 169.4 (107.2) | 150.9 (94.9) |
| % Change Week 24 | 17.77 (69.77) | −1.19 (42.49) | −3.35 (53.29) |
| Week 52 | 177.2 (81.2) | 157.2 (92.9) | 141.0 (76.9) |
| % Change Week 52 | 12.57 (47.25) | −4.25 (43.67) | −11.26 (38.15) |
| NK cells, mean cells/mm$^3$ (SD) | | | |
| Baseline | 163.4 (76.7) | 166.2 (110.9) | 175.0 (95.7) |
| Week 24 | 169.0 (80.3) | 199.3 (106.6) | 205.1 (87.9) |
| % Change Week 24 | 9.50 (44.88) | 32.71 (56.55) | 33.03 (65.13) |
| Week 52 | 158.3 (82.7) | 213.0 (113.9) | 223.5 (117.9) |
| % Change Week 52 | 2.77 (43.07) | 48.14 (82.09) | 50.5 (84.1) |
| CD4+ cells, mean cells/mm$^3$ (SD) | | | |
| Baseline | 686.9 (248.3) | 698.8 (241.3) | 664.4 (261.0) |
| Week 24 | 692.8 (235.3) | 646.2 (216.2) | 606.5 (222.8) |
| % Change Week 24 | 3.87 (26.72) | −4.42 (27.20) | −4.66 (28.24) |
| Week 52 | 682.9 (219.6) | 612.8 (202.6) | 581.7 (259.8) |
| % Change Week 52 | 2.77 (26.45) | −6.95 (30.33) | −8.94 (29.97) |
| CD8+ cells, mean cells/mm$^3$ (SD) | | | |
| Baseline | 355.3 (156.2) | 361.4 (146.4) | 353.4 (165.8) |
| Week 24 | 363.9 (176.8) | 328.0 (139.6) | 309.5 (133.4) |
| % Change Week 24 | 4.11 (40.70) | −4.73 (30.67) | −6.49 (30.23) |
| Week 52 | 344.9 (160.9) | 315.7 (139.6) | 295.7 (151.0) |
| % Change Week 52 | 3.05 (44.60) | −9.12 (30.96) | −9.83 (33.94) |
| CD4/CD8 ratio | | | |
| Baseline | 2.2 (0.9) | 2.1 (0.9) | 2.1 (09) |
| Week 24 | 2.2 (0.9) | 2.2 (0.9) | 2.2 (1.0) |
| % Change Week 24 | 4.23 (25.38) | 2.87 (18.55) | 4.07 (19.85) |
| Week 52 | 2.3 (1.0) | 2.2 (0.9) | 2.2 (0.9) |
| % Change Week 52 | 6.36 (30.00) | 4.57 (18.77) | 4.47 (20.63) |

SD, standard deviation; NK, natural killer.

Liver function test (LFT) abnormalities were above 5×ULN, occurred in 4% of DAC- and <1% of placebo-treated patients. These abnormalities typically occurred late in the treatment period (median onset+day 308) and resolved with a median time of 62 days. Of the 17 DAC HYP-treated patients with elevations of >5×ULN, 6 continued or resumed treatment with DAC HYP for at least 6 months after resolution, all without recurrence during this period. In 2 patients, LFT elevations were associated with infections (one case of hepatitis B and one case of cytomegalovirus infection).

Immunogenicity.

At week 24, neutralizing antibodies to DAC HYP were detected in 6 (2%) DAC HYP-treated patients (5 patients in the 150 mg dose group and 1 subject in the 300 mg dose group). In some patients these antibodies were transient, and at week 52 neutralizing antibodies to DAC HYP were present in only 1 subject from each DAC HYP dose group.

Conclusion.

Antagonism of CD25 with monthly, subcutaneous DAC HYP monotherapy demonstrated robust and clinically meaningful effects over 1 year on MS disease activity, e.g., as measured by reduction in relapse rate, new MRI defined lesion activity and disability progression in a predominantly treatment naïve population of MS patients.

8. SPECIFIC EMBODIMENTS, INCORPORATION BY REFERENCE

Various aspects of the present disclosure are described in the embodiments set forth in the following numbered paragraphs.

1. A modified NS0 cell that has been adapted to grow in serum- and cholesterol-free media and that is engineered to express a recombinant protein, said cell being capable of achieving a volumetric productivity exceeding 100 mg/L/day recombinant protein in a culture of 100 L in a 10-day fed-batch process when grown in serum- and cholesterol-free media.

2. The modified NS0 cell of embodiment 1 which is capable of achieving a volumetric productivity exceeding 100 mg/L/day recombinant protein in a culture of 1,000 L in a 10-day fed-batch process when grown in media free of cholesterol and animal-derived components.

3. The modified NS0 cell of embodiment 1 which is capable of achieving a volumetric productivity exceeding 100 mg/L/ day recombinant protein in a culture of 16,000 L in a 10-day fed-batch process when grown in media free of cholesterol and animal-derived components.

4. The modified NS0 cell of any one of embodiments 1-3 to which a feed medium is added according to the following schedule, where the volume added represents the percentage of the initial cell culture volume:

| Day | Volume added |
|---|---|
| 0 | 0 |
| 1 | 0 |
| 2 | 4 |
| 3 | 7.8 |
| 4 | 7.8 |
| 5 | 7.8 |
| 6 | 11 |
| 7 | 13 |
| 8 | 15 |
| 9 | 15 |
| 10 | 0 |

5. The modified NS0 cell of embodiment 1 that is capable of achieving a volumetric productivity exceeding 200 mg/L/day recombinant protein in a culture of at least 100 L in a 13-day fed-batch process.

6. The modified NS0 cell of embodiment 5 which is capable of achieving a volumetric productivity exceeding 200 mg/L/day recombinant protein in a culture of 1,000 L in a 13-day fed-batch process when grown in cholesterol-free media.

7. The modified NS0 cell of embodiment 5 which is capable of achieving a volumetric productivity exceeding 100 mg/L/day recombinant protein in a culture of 16,000 L in a 10-day fed-batch process when grown in serum- and cholesterol-free media.

8. The modified NS0 cell of embodiment 1 which is stably transfected with a nucleic acid useful for expressing an anti-CD25 monoclonal antibody.

9. The modified NS0 cell of embodiment 8 in which the anti-CD25 monoclonal antibody comprises a VL chain corresponding in sequence to positions 21-233 of SEQ ID NO:2 and a VH chain corresponding in sequence to positions 20 to 465 of SEQ ID NO:4.

10. The modified NS0 cell of embodiment 1 which was transformed with vector pAbX.gpt.

11. The modified NS0 cell of embodiment 1 which was transformed with vector pHAT.IgG1.rg.dE.

12. The modified NS0 cell of embodiment 1 which is designated as clone 7A11-5H7-14-43.

13. A method of producing a recombinant protein, comprising culturing the modified NS0 cell of any one of embodiments 1-12.

14. The method of embodiment 13, wherein the modified NS0 cell is cultured under conditions that result in the production of at least 100 mg/L/day recombinant protein in a 100 L, 1,000 L or 16,000 L culture in a 10-day fed-batch process, or at least 200 mg/L/day recombinant protein in a 100 L, 1,000 L or 16,000 L culture in a 13-day fed-batch process.

15. The method of embodiment 13 or embodiment 14, wherein the modified NS0 cell is cultured in the absence of serum and cholesterol.

16. The method of embodiment 15 wherein the modified NS0 cell is cultured in the absence of tropolone and hydrocortisone.

17. The method of embodiment 13 or embodiment 14, wherein the modified NS0 cell is cultured in a basal and/or feed medium containing 10-35 g/L glucose.

18. The method of embodiment 17, wherein the modified NS0 cell is cultured in a basal medium containing 15 g/L glucose and/or a feed medium containing 28 g/L glucose.

19. The method of embodiment 18, wherein the basal medium is composed of the components of PFBM2±10%.

20. The method of embodiment 18, wherein the feed medium is composed of the components of PFFM3±10%.

21. The method of embodiment 19 or embodiment 20, wherein the cell is cultured in basal medium for 1-3 days, and then in feed medium for 10-13 days.

22. The method of embodiment 18, wherein the feed medium is added according to the schedule outlined in Table 7±10%.

23. A vector useful for recombinantly expressing a protein of interest, comprising a weak promoter driving expression of a selectable marker operable in mammalian cells and a strong promoter driving expression of a protein of interest.

24. The vector of embodiment 23, wherein the protein of interest is a therapeutic antibody.

25. The vector of embodiment 24, wherein the therapeutic antibody is an anti-CD25 antibody.

26. The vector of embodiment 25, wherein the anti-CD25 antibody comprises the CDRs of daclizumab.

27. The vector of embodiment 26, wherein the anti-CD25 antibody is daclizumab.

28. A method for obtaining a mammalian host cell that has a high volumetric productivity of a protein of interest, comprising transfecting the cell with the vector of any one of embodiments 23-27, and selecting a cell that is capable of producing at least 100 mg/L/day protein of interest in a 100 L, 1,000 L or 16,000 L culture in a 10-day fed-batch process or at least 200 mg/L/day recombinant protein in a 100 L, 1,000 L or 16,000 L culture in a 13-day fed-batch process.

29. A composition comprising daclizumab, where the daclizumab is characterized by the presence of a pE/Q heavy chain N-linked isoform and/or a Q/VHS heavy chain N-terminal isoform.

30. The composition of embodiment 29 in which the pE/Q heavy chain N-terminal isoform constitutes approximately 6-15% of the daclizumab.

31. The composition of embodiment 29 in which the pE/Q heavy chain N-terminal isoform constitutes approximately 7-12% of the daclizumab.

32. The composition of any one of embodiments 29-31 in which the Q/VHS heavy chain N-terminal isoform constitutes approximately 1-15% of the daclizumab.

33. The composition of embodiment 32 in which the Q/VHS heavy chain N-terminal isoform constitutes approximately 3-12% of the daclizumab.

34. The composition of embodiment 29 in which the heavy chain of daclizumab exists in the following N-terminal isoforms:

| Isoform | Prevalence |
|---|---|
| pE/pE | 25%-50% |
| pE/Q | 6%-15% |
| pE/VHS | 25%-48% |
| Q/VHS | 1%-15% |
| VHS/VHS | 0.5%-25% |

35. The composition of embodiment 29 in which the heavy chain of daclizumab exists in the following N-terminal isoforms:

| Isoform | Prevalence |
|---|---|
| pE/pE | 31-46% |
| pE/Q | 7%-12% |
| pE/VHS | 31%-42% |
| Q/VHS | 3%-12% |
| VHS/VHS | 2%-17% |

36. The composition of embodiment 29, where the daclizumab is characterized by a cation exchange chromatography isoform profile substantially similar to that of FIG. 18.

37. The composition of embodiment 29, where the daclizumab is DAC HYP.

38. A composition comprising daclizumab, where the daclizumab is characterized by an N-linked glycosylation HPLC profile containing two main peaks, one corresponding to oligosaccharide G0 GlcNAc and one corresponding to oligosaccharide G0, where the combined AUC of these two peaks constitutes about 88-99.5% of the total AUC of all peaks.

39. The composition of embodiment 38, in which the AUC of the G0 GlcNAc peak constitutes about 5-18% of the total AUC of all peaks and the AUC of the G0 peak constitutes about 75-92% of the total AUC of all peaks.

40. The composition of embodiment 39, in which the AUC of the G0-GlcNAc peak constitutes about 6-16% of the total AUC of all peaks and the AUC of the G0 peak constitutes about 78-90% of the total AUC of all peaks.

41. The composition of any one of embodiments 38-40 in which the N-linked glycosylation profile has less than about 3% of Man5.

42. The composition of embodiment 41 in which the N-linked glycosylation profile has less than about 0.5% G2, Man6 and/or Man7.

43. The composition of embodiment 38, in which the N-linked glycosylation profile contains a third peak corresponding to sialylated oligosaccharides, and the AUC of the sialylated oligosaccharide peak constitutes 1% or less of the total AUC of all peaks.

44. The composition of embodiment 38, in which the N-linked glycosylation profile contains a third peak corresponding to oligosaccharide G1, and the AUC of the G1 peak constitutes about 1-5% of the total AUC of all peaks.

45. The composition of embodiment 44, in which the AUC of the G1 peak constitutes about 1-2% of the total AUC of all peaks.

46. The composition of embodiment 38, in which the daclizumab has an N-linked glycosylation HPLC profile substantially similar to that of FIG. 19 or to that of the lower panel of FIG. 21.

47. The composition of embodiment 38, in which the daclizumab is DAC HYP.

48. A composition comprising daclizumab which exhibits less than 35% ADCC average cytotoxicity as measured in an in vitro cellular assay using effector cells from at least 3 healthy donors and Kit 225 K6 cells as target cells, at a daclizumab concentration of 1 μg/mL and an effector to target cell ratio of about 25:1.

49. The composition of embodiment 48 wherein the daclizumab exhibits 10% to 30% ADCC average cytotoxicity in said assay.

50. The composition of embodiment 48 or embodiment 49 wherein said assay uses effector cells from at least 6 healthy donors.

51. The composition of embodiment 48 or embodiment 49 wherein said assay uses effector cells from at least 10 healthy donors.

52. The composition of any one of embodiments 48-51, in which the daclizumab is DAC HYP.

53. A composition useful for making a daclizumab drug formulation, comprising about 150-190 mg/mL daclizumab and quantities of excipients such that dilution of the composition with a dilution buffer yields a diluted composition that contains about 85-165 mg/mL daclizumab and has an osmolality in the range of about 267-327 mOsm/kg and a pH in the range of about pH 5.8-6.2 at 25° C., and in which at least about 95% of the daclizumab is in monomer form, as measured by size exclusion chromatography.

54. The composition of embodiment 53 which contains quantities of excipients such that when diluted with a dilution buffer the diluted composition contains about 85-115 mg/mL daclizumab.

55. The composition of embodiment 53 which contains quantities of excipients such that when diluted with a dilution buffer the diluted composition contains about 150±15 mg/mL daclizumab.

56. A composition comprising about 4 to 15 mg/mL daclizumab, where 0.1% or less of the daclizumab is in aggregate form.

57. The composition of embodiment 56 which is obtained by purifying a daclizumab composition comprising about 4 to 15 mg/mL daclizimab, where up to 2.5% of the daclizumab is in aggregate form, via column chromatography on a weak cation exchange resin.

58. The composition of embodiment 57, where the weak cation exchange resin is CM-650M.

59. The composition of embodiment 58, where the CM-650M resin is equilibrated with an equilibration buffer containing about 20 mM sodium citrate, pH 4.4-4.6, and the daclizumab is eluted with an elution buffer containing about 20 mM sodium citrate and about 75 mM sodium sulfate, pH 4.4-4.6.

60. The composition of embodiment 59, where the chromatography is carried out in a cylindrical column using a resin bed having a height of about 10-30 cm or about 17-19 cm, and the daclizumab is eluted at a temperature in the range of about 4-22° C. or about 18-22° C., and a flow rate in the range of about 50-200 cm/hr or about 90-110 cm/hr.

61. A composition suitable for administration to humans, comprising about 85-165 mg/mL daclizumab; and about 0.02-0.04% (w/v) polysorbate 80, where the composition has an osmolality in the range of about 267-327 mOsm/kg and a pH in the range of about pH 5.8-6.2 at 25° C., and at least about 95% of the daclizumab is in monomer form, as measured by size exclusion chromatography.

62. The composition of embodiment 61, in which at least about 99% of the daclizumab is in monomer form, as measured by size exclusion chromatography.

63. The composition of embodiment 61 which comprises about 85-115 mg/mL daclizumab.

64. The composition of embodiment 63, which consists essentially of about 100 mg/mL daclizumab, about 40 mM sodium succinate, about 100 mM sodium chloride, and about 0.03% (w/v) polysorbate 80, and has a pH of about 6.0 at 25° C.

65. The composition of embodiment 61 which comprises about 135-165 mg/mL daclizumab.

66. The composition of embodiment 65, which consists essentially of about 150 mg/mL daclizumab, about 40 mM sodium succinate, about 100 mM sodium chloride, and about 0.03% (w/v) polysorbate 80, and has a pH of about 6.0 at 25° C.

67. The composition of embodiment 65 which is obtained by a process comprising the steps of concentrating a daclizumab composition comprising about 4 to 15 mg/mL daclizumab via ultrafiltration in a suitable buffer to achieve a daclizumab concentration in the range of about 85-180 mg/mL and optionally diluting the concentrated composition with a dilution buffer.

68. A pharmaceutical composition suitable for subcutaneous administration comprising about 85-165 mg/mL daclizumab, where the percentage of daclizumab in aggregate form does not exceed about 3% following storage for a period of about 12 months at a temperature in the range of about 2-8° C.

69. The pharmaceutical composition of embodiment 68 which comprises about 85-115 mg/mL daclizumab.

70. The pharmaceutical composition of embodiment 68 which comprises about 135-165 mg/mL daclizumab.

71. The pharmaceutical composition of embodiment 69 or embodiment 70 in which the percentage of daclizumab in aggregate form does not exceed about 2% following storage for a period of about 12 months at a temperature in the range of about 2-8° C.

72. The pharmaceutical composition of embodiment 69 or embodiment 70 in which the percentage of daclizumab in aggregate form does not exceed about 3% following storage for a period of about 18 months at a temperature in the range of about 2-8° C.

73. A process for harvesting a recombinant protein from a cell culture, comprising the steps of:

adjusting the pH of a cell culture that expresses and secretes a recombinant protein to a pH in the range of about pH 4.5-5.5;

(ii) incubating the pH-adjusted cell culture for about 30-90 minutes at a temperature in the range of about 4 to 15° C.; and (iii) centrifuging the incubated pH-adjusted cell culture to remove cell debris.

74. A process for producing a purified daclizumab composition, comprising the steps of:

(i) adsorbing daclizumab from a crude daclizumab preparation onto affinity chromatography resin;

(ii) washing the affinity chromatography resin with a wash buffer to remove contaminants;

(iii) eluting the adsorbed daclizumab with an elution buffer;

(iv) inactivating viruses in the eluate by adjusting the pH to a pH in the range of about pH 3-4 and incubating the pH-adjusted eluate at specified temperature for a period of time sufficient to inactivate viruses;

(v) neutralizing the virus-inactivated eluate to a pH in the range of about pH 7.7-7.9 (measured at 25° C.);

(vi) flowing the neutralized eluate across a strong anion exchange chromatography resin;

(vii) adsorbing the daclizumab of the eluate of step (vi) onto a weak cation exchange chromatography resin; and (viii) eluting the adsorbed daclizumab from the weak cation exchange chromatography resin.

75. The process of embodiment 74 in which the crude daclizumab preparation is harvested from a cell culture.

76. The process of embodiment 74 in which the crude daclizumab preparation is obtained by culturing host cell 7A11-5H7-14-43 under conditions in which daclizumab is secreted into the culture medium and harvesting the secreted daclizumab.

77. The process of embodiment 76 in which the daclizumab is harvested using the method of embodiment 73.

78. The process of embodiment 74, which further comprises the steps of:

(ix) filtering the eluted daclizumab composition of step (viii) to remove viruses; and (x) concentrating the filtered solution via ultrafiltration to yield a purified, daclizumab composition comprising about 85-180 mg/mL daclizumab.

79. The process of embodiment 78, which further comprises the step of diluting the purified daclizumab composition with a dilution buffer so as to obtain a composition comprising about 85-165 mg/mL daclizumab; and about 0.02-0.04% (w/v) polysorbate 80, where the composition has an osmolality in the range of about 267-327 mOsm/kg and a pH in the range of about pH 5.8-6.2 at 25° C., and at least about 95% of the daclizumab is in monomer form, as measured by size exclusion chromatography.

80. The process of embodiment 79, wherein the composition obtained has less than 50 ppm of host cell proteins from a recombinant source of daclizumab, less than 10 ppm of protein A, and no more than 3% of the daclizumab in the composition is in aggregate form.

81. Basal medium PFBM2.

82. Feed medium PFFM3.

83. A daclizumab composition, which is obtained by a process comprising the step of culturing a host cell according to any one of embodiments 1-12 under conditions in which daclizumab is secreted into the culture medium.

84. The daclizumab composition of embodiment 83, in which the process further comprises the step of isolating the secreted daclizumab from the cell culture medium.

85. A buffer useful for sanitizing a protein A affinity chromatography resin, comprising about 100-500 mM sodium citrate, about 10-30 mM NaOH and about 0.5-3% (v/v) benzyl alcohol.

86. A method of sanitizing a protein A affinity chromatography column, comprising washing the column with the sanitization buffer of embodiment 85 at a flow rate and for a period of time sufficient to sanitize the column.

87. The method of embodiment 86, in which the column is washed with approximately 1.8 column volumes of sanitization buffer at a flow rate of about 150 cm/hr, the washed column incubated without flow for a period of about 30-45 min., and then equilibrated with an equilibration buffer.

88. The method of embodiment 87, in which the equilibration buffer comprises about 20 mM sodium citrate and 150 mM NaCl, and has a pH of about pH 7 (at 25° C.).

89. A method of treating a patient suffering from multiple sclerosis, comprising administering to the patient an amount of a DAC HYP composition sufficient to provide therapeutic benefit.

90. The method of embodiment 89 in which the DAC HYP composition is administered intravenously.

91. The method of embodiment 90 in which the DAC HYP composition is administered in amount corresponding to about 0.8-0.9 mg/kg DAC HYP.

92. The method of embodiment 91 in which the DAC HYP composition is administered in an amount corresponding to about 1 mg/kg DAC HYP.

93. The method of any one of embodiments 89-92 in which the DAC HYP is administered once per week for a period of at least 6 weeks, at least 12 weeks, at least 24 weeks.

94. The method of any one of embodiments 89-93 in which the DAC HYP is administered as monotherapy.

95. The method of embodiment 94 in which the patient has either failed to respond to prior treatment with interferon-beta or has discontinued prior treatment with interferon-beta.

96. The method of any one of embodiments 89-93 in which the DAC HYP is administered adjunctively to interferon-beta.

97. The method of embodiment 89 in which the DAC HYP composition is administered subcutaneously.

98. The method of embodiment 97 in which the DAC HYP composition is administered in an amount corresponding to about 1 mg/kg DAC HYP.

99. The method of embodiment 98 in which the DAC HYP composition is administered once every two weeks.

100. The method of embodiment 99 in which the DAC HYP composition is administered for a total of about 24 weeks.

101. The method of embodiment 97 in which the DAC HYP composition is administered in an amount corresponding to about 2 mg/kg DAC HYP.

102. The method of embodiment 101 in which the DAC HYP composition is administered once every 4 weeks.

103. The method of embodiment 102 in which the DAC HYP composition is administered for a total of about 24 weeks.

104. The method of embodiment 103, in which the DAC HYP composition is administered in an amount corresponding to 75 mg to 300 mg DAC HYP.

105. The method of embodiment 104 in which the DAC HYP composition is administered in an amount corresponding to 150 mg.

106. The method of embodiment 104 in which the DAC HYP composition is administered in an amount corresponding to 300 mg.

107. The method of any one of embodiments 103-106 wherein the DAC HYP composition is administered once every 4 weeks.

108. The method of embodiment 107 wherein the DAC HYP composition is administered for a total of at least 48 weeks.

109. The method of any one of embodiments 103-108 in which the DAC HYP is administered as monotherapy.

110. The method of embodiment 109 in which the patient has either failed to respond to prior treatment with interferon-beta or has discontinued prior treatment with interferon-beta.

111. The method of any one of embodiments 103-108 in which the DAC HYP is administered adjunctively to interferon-beta.

112. A recombinant daclizumab, from a cell culture, obtained or obtainable by a process comprising the steps of:

- (i) adjusting the pH of a cell culture that expresses and secretes a recombinant protein to a pH in the range of about pH 4.5-5.5;
- (ii) incubating the pH-adjusted cell culture for about 30-90 minutes at a temperature in the range of about 4 to 15° C.; and
- (iii) centrifuging the incubated pH-adjusted cell culture to remove cell debris.

113. A purified daclizumab composition, obtained or obtainable by a process comprising the steps of:

- (i) adsorbing daclizumab from a crude daclizumab preparation onto affinity chromatography resin;
- (ii) washing the affinity chromatography resin with a wash buffer to remove contaminants;
- (iii) eluting the adsorbed daclizumab with an elution buffer;
- (iv) inactivating viruses in the eluate by adjusting the pH to a pH in the range of about pH 3-4 and incubating the pH-adjusted eluate at specified temperature for a period of time sufficient to inactivate viruses;
- (v) neutralizing the virus-inactivated eluate to a pH in the range of about pH 7.7-7.9 (measured at 25° C.);
- (vi) flowing the neutralized eluate across a strong anion exchange chromatography resin;
- (vii) adsorbing the daclizumab of the eluate of step (vi) onto a weak cation exchange chromatography resin; and
- (viii) eluting the adsorbed daclizumab from the weak cation exchange chromatography resin.

114. A purified daclizumab composition, obtained or obtainable by the process of any one of embodiments 74-80.

Deposit of strain: A strain of NS0 cells adapted to grow in serum-free and cholesterol-free medium that has been stably transfected with vector pHAT.IgG1.rg.dE and which can be used to produce DAC HYP, clone 7A11-5H7-14-43, also referred to as Daclizumab dWCB IP072911, was deposited with the American Type Tissue Collection ("ATCC") at 10801 University Blvd., Manassas, Va. 20510-209, U.S.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating a patient suffering from multiple sclerosis, comprising administering to the patient an amount of a daclizumab composition sufficient to provide therapeutic benefit, wherein the daclizumab has two or more of the following:

(a) an N-terminal isoform with one pyroglutamate residue and one glutamine residue that comprises 3%-17% of the total daclizumab:

(b) an N-linked oligosaccharide profile comprising two main peaks and a minor peak, wherein one of the two main peaks is GO-GlcNAc glycoform present in about 5% to about 20% of the AUC, the other main peak is GO glycoform present in about 70% to about 99.2% of the AUC, and the minor peak is G1 glycoform present in 1% to 9% of the AUC when determined according to the method described in Section 7.6.14, (c) <3% aggregates when formulated at a concentration of about 150 mg/mL.

2. The method of claim 1 in which the daclizumab composition is administered:

(a) subcutaneously;

(b) in an amount corresponding to about 1 mg/kg daclizumab, once every two weeks or in an amount corresponding to about 2 mg/kg daclizumab, once every month;

(c) for a total of about 24 weeks; or (d) according to any combination of (a)-(c).

3. The method of claim 2, in which the daclizumab composition is administered in an amount corresponding to 75 mg to 300 mg daclizumab, or 150 mg, or 300 mg.

4. The method of claim 3 wherein the daclizumab composition is administered subcutaneously in an amount corresponding to 150 mg daclizumab once every month.

5. The method of claim 3 in which the daclizumab is administered as monotherapy, in which the patient has either failed to respond to prior treatment with interferon-beta or has discontinued prior treatment with interferon-beta.

6. The method of claim 3 in which the daclizumab is administered adjunctively to interferon-beta.

7. The method of claim 1 in which the daclizumab has an N-linked glycosylation profile determined according to the method described in Section 7.6.14, in which the total AUC of the peaks in the profile corresponding to non-fucosylated mannose glycosyls is less than about 6% of the total AUC of all peaks in the profile.

8. The method of claim 4 which is administered for a total of at least 48 weeks.

* * * * *